(12) United States Patent
Hallahan et al.

(10) Patent No.: US 7,306,925 B2
(45) Date of Patent: *Dec. 11, 2007

(54) PHAGE ANTIBODIES TO RADIATION-INDUCIBLE NEOANTIGENS

(75) Inventors: Dennis E. Hallahan, Nashville, TN (US); Raymond Mernaugh, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 380 days.

This patent is subject to a terminal disclaimer.

(21) Appl. No.: 10/689,006

(22) Filed: Oct. 20, 2003

(65) Prior Publication Data

US 2004/0191249 A1    Sep. 30, 2004

Related U.S. Application Data

(63) Continuation-in-part of application No. 10/259,087, filed on Sep. 27, 2002, and a continuation-in-part of application No. 09/914,605, filed on Nov. 9, 2001, now Pat. No. 7,049,140.

(51) Int. Cl.
    *C12Q 1/68* (2006.01)
(52) U.S. Cl. .................. 435/7.2; 435/235.1; 435/6
(58) Field of Classification Search ............ None
    See application file for complete search history.

(56) References Cited

U.S. PATENT DOCUMENTS

| | | | |
|---|---|---|---|
| 4,515,165 A | 5/1985 | Carroll | |
| 4,619,823 A | 10/1986 | Yokoyama et al. | 424/1.1 |
| 4,670,386 A | 6/1987 | Sugaar | |
| 5,093,104 A | 3/1992 | Kaminsky | 424/1.1 |
| 5,292,524 A | 3/1994 | Male et al. | |
| 5,328,840 A | 7/1994 | Coller | |
| 5,334,369 A | 8/1994 | Halushka et al. | |
| 5,382,680 A | 1/1995 | Abraham et al. | |
| 5,516,881 A | 5/1996 | Lee et al. | |
| 5,693,627 A | 12/1997 | Schieven | |
| 5,759,542 A | 6/1998 | Gurewich | |
| 2003/0130190 A1* | 7/2003 | Hallahan et al. | 514/12 |

FOREIGN PATENT DOCUMENTS

| | | |
|---|---|---|
| DE | 2621311 | 11/1976 |
| EP | 229718 | 1/1987 |
| WO | WO8605693 | 10/1986 |
| WO | WO9306835 | 4/1993 |
| WO | WO93/14791 | 8/1993 |
| WO | WO9320229 | 10/1993 |
| WO | WO9533496 | 12/1995 |
| WO | WO9625947 | 8/1996 |

OTHER PUBLICATIONS

International Preliminary Examination Report for corresponding PCT Appl. No. PCT/US04/34719 dated Oct. 12, 2005.

U.S. Appl. No. 10/259,086, filed Jul. 10, 2003, Hallahan et al.

International Search Report for corresponding PCT Appl. No. PCT/US04/34719 dated Jan. 26, 2005.

Arap et al., Cancer Treatment by Targeted Drug Delivery to Tumor Vasculature in a Mouse Model, *Science* 279:377-380 (Jan. 16, 1998).

Bird et al., Single-Chain Antigen-Binding Proteins, *Science* 242:423-426 (Oct. 21, 1988).

Edmonds, Antibody-Targeted Chemotherapy with Mylotarg Shows Promise for Many Adults with Deadly Form of Leukemia, *American Society of Clinical Oncology Meeting in New Orleans* (May 21, 2000).

Ellerby et al, Anti-cancer activity of targeted pro-apoptotic peptides, *Nature Medicine* 5(9):1032-1038 (Sep. 1999).

Fox and Harris, Markers of tumor angiogenesis: clinical applications in prognosis and anti-angiogenic therapy, *Investigational New Drugs* 15:15-28 (1997).

Hallahan et al., Spatial and temporal control of gene therapy using ionizing radiation, *Nat Med.* 1(8):786-791 (Aug. 1995) (ABSTRACT).

Hallahan, Radiation-Mediated Gene Expression in the Pathogenesis of the Clinical Radiation Response, *Semin Radiat Oncol.* 6(4):250-267 (Oct. 1996) (ABSTRACT).

Hallahan et al., Radiation-Mediated Control of Drug Delivery, *Am J. Clin Onocol.* 24(5):473-480 (Oct. 2001) (ABSTRACT).

Hallahan et al., X-ray-induced P-selectin localization to the lumen of tumor blood vessels, *Cancer Res.* 58(2):5216-5220 (Nov. 15, 1998) (ABSTRACT).

Hellström et al., Immunoconjugates and immunotoxins for therapy of solid tumors, *Cancer Chemother Pharmacol.* 38(Suppl.):S35-S36 (1996).

Huston et al., Protein engineering of antibody binding sites: Recovery of specific activity in an anti-digoxin single-chain Fv analogue produced in *Escherichia coli*, *Proc. Natl. Acad. Sci. USA* 85:5879-5883 (Aug. 1988).

Llovet et al., Arterial embolisation or chemoembolisation versus symptomatic treatment in patients with unresectable hepatocellular carcinoma: a randomized controlled trial, *The Lancet* 359:1734-1739 (May 18, 2002).

Martin et al., Targeted Retroviral Infection of Tumor Cells by Receptor Cooperation, *J. of Virology* 77(4):2753-2756 (Feb. 2003).

Molema et al., Tumor Vascular Endothelium: Barrier or Target in Tumor Directed Drug Delivery and Immunotherapy, *Pharmaceutical Research* 14(1):2-10 (1997).

(Continued)

*Primary Examiner*—James Ketter
(74) *Attorney, Agent, or Firm*—Jenkins, Wilson, Taylor & Hunt, P.A.

(57) ABSTRACT

A method for identifying a molecule that binds an irradiated tumor in a subject and molecules identified thereby. The method includes the steps of: (a) exposing a tumor to ionizing radiation; (b) administering to a subject a library of diverse molecules; and (c) isolating from the tumor one or more molecules of the library of diverse molecules, whereby a molecule that binds an irradiated tumor is identified. Also provided are therapeutic and diagnostic methods using targeting ligands that bind an irradiated tumor.

24 Claims, 5 Drawing Sheets

OTHER PUBLICATIONS

O'Brien et al., Antibody Phage Display: Methods and Protocols, *E-STREAMS* 5(12):401 (Dec. 2002) (www.e-streams.com/es0512/es0512_2216.html).

Pastan, Targeted therapy of cancer with recombinant immunotoxins, *Biochimica et Biophysica Acta* 1333:C1-C6 (1997).

Mechanism of Action, www.herceptin.com/herceptin/physician/j_profile/mechanism.htm Genentech, 3 pages (Aug. 6, 2003).

Mechanism of Action: Targeted Therapy Provides a Unique Profile of Efficacy, www.rituxan.com/rituxan/professional/e_product_info/mode_of_action.htm, 3 pages (Aug. 8, 2003).

Campath® Fact Sheet, www.campath.com/medpros/factsheet.html, 3 pages, (Aug. 8, 2003).

Package Insert, HUMIRA™ (adalimumab), *Abbott Laboratories* www.fda.gov/cber/label/adalabb123102LB.htm, 13 pages (Aug. 8, 2003).

Zevalin, First in Radioimmunotherapy: Mechanism of action www.zevalin.com/html/HealthcareProfessionals/ProductInformation/productInform . . . , 1 page (Aug. 8, 2003).

Hirata et al., Artificial Metastases and Decrease of Fibrinolysis in the Nude Mouse Lung After Hemithoracic Irradiation, *Clin. Expl. Metastasis*, 2(4), p. 311-319, (1984).

Hirata, Fate of Intravenously Injected Human Tumor Cells in the Lung of Nude Mice Following Whole-Body X-Irradiation, *Invasion Metastasis*, p. 61-70, (1985).

Stratton et al., Imaging Arterial Thrombosis: Comparison of Technetium-99m-Labeled Monoclonal Antifibrin Antibodies and Indium-111-Platelets, *J. Nucl. Med.*, p. 1731-1737, (1994).

Weichselbaum et al., Gene Therapy Targeted by Radiation Preferentially Radiosensitizes Tumor Cells, *Cancer Research*, p. 4266-4269, (Aug. 15, 1994).

\* cited by examiner

PHAGE ANTIBODIES TO RADIATION-INDUCIBLE NEOANTIGENS

CROSS REFERENCE TO RELATED APPLICATIONS

This application is a continuation-in-part of U.S. patent application Ser. No. 09/914,605, filed Nov. 9, 2001 now U.S. Pat. No. 7,049,140, and Ser. No. 10/259,087, filed Sep. 27, 2002, each of which is herein incorporated by reference in its entirety.

GRANT STATEMENT

This work was supported by grants CA58508, CA68485, CA70937, CA88076, CA89674, CA89888, and CA90949 from the U.S. National Institutes of Health. Thus, the U.S. government has certain rights in the presently disclosed subject matter.

TECHNICAL FIELD

The presently disclosed subject matter generally relates to antibodies that bind to radiation-inducible targets. More particularly, the presently disclosed subject matter provides a method for screening a plurality of phage-displayed antibodies for an ability to bind to a radiation-inducible neoantigen present on a cell. Also provided are compositions comprising scFv antibodies that bind to radiation-inducible targets.

Table of Abbreviations

| | |
|---|---|
| 6xHis | an epitope tag consisting of six consecutive histidine residues |
| AR | autoradiography |
| CAM | cell adhesion molecule |
| CDR | complementarity-determining region |
| CEA | carcinoembryonic antigen |
| CPM | counts per minute |
| CT | computerized tomography |
| DiI | 1,1'-Dioctadecyl-3,3,3',3'-tetramethylindocarbocyanine perchlorate |
| DOPE | dioleoylphosphatidylethanolanime |
| DTPA | diethylenetriamine pentaacetate |
| DWI | diffusion-weighted imaging |
| EDC | 1-Ethyl-3-(3-dimethylaminopropyl)-carbodiimide |
| EDTA | ethylenediamine tetraacetic acid |
| Fc | immunoglobulin constant region |
| FMAT | fluorometric microvolume assay technology |
| FITC | fluorescein isothiocyanate |
| fMRI | functional MR imaging |
| GBq | gigabecquerels |
| GEE | Generalized Estimating Equation |
| GM-CSF | granulocyte-macrophage colony stimulating factor |
| GP | glycoprotein |
| Gy | Grays |
| HCL | hydrochloric acid |
| HLA | human leukocyte antigen |
| HMPAO | hexamethylpropylene amine oxime |
| HNSCC | head and neck squamous cell carcinoma |
| HRP | horseradish peroxidase |
| HPLC | high performance liquid chromatography |
| HSPs | high scoring sequence pairs |
| HUVEC | human umbilical vein endothelial cells |
| IFN | interferon |
| IL | interleukin |
| IP | imaging plate |
| IPX | Internet Packet eXchange |
| LUER | low energy high resolution |
| M | molar |
| MALDI-MS | matrix-assisted laser desorption/ionization coupled mass spectrometry |
| MBq | megabecquerels |
| µCi | microcuries |
| mCi | millicuries |
| NM | nuclear magnetic |
| MRI | magnetic resonance imaging |
| MRS | proton magnetic resonance spectroscopy |
| MS | mass spectrometry |
| MTI | magnetization transfer imaging (MTI), |
| Ni-NTA | nickel-nitrilotriacetic acid |
| OD | optical density |
| PBS | phosphate-buffered saline |
| PCR | Polymerase Chain Reaction |
| PEG | polyethylene glycol |
| PET | positron emission spectroscopy |
| PFU | plaque forming unit |
| REML | restricted/residual maximum likelihood |
| ROI | region(s) of interest |
| SAS | Statistical Analysis System |
| scFv | single chain fragment variable |
| SDS | sodium dodecyl sulfate |
| SHNH | succinimidyl 6-hydrazinium nicotinate hydrochloride |
| SPDP | N-succinimidyl 3-(2-pyridylthio)propionate |
| SPECT | single photon emission computed tomography |
| SQUID | superconducting quantum interference device |
| T/B | tumor-to-background ratio |
| TFA | trifluoroacetic acid |
| TNF | tumor necrosis factor |
| TUNEL | terminal deoxynucleotidyl transferase-mediated nick end labeling |
| $V_H$ | heavy chain variable region of an antibody or antibody fragment |
| $V_L$ | light chain variable region of an antibody or antibody fragment |

Amino Acid Abbreviations, Codes, and Functionally Equivalent Codons

| Amino Acid | 3-Letter | 1-Letter | Codons |
|---|---|---|---|
| Alanine | Ala | A | GCA GCC GCG GCU |
| Arginine | Arg | R | AGA AGG CGA CGC CGG CGU |
| Asparagine | Asn | N | AAC AAU |
| Aspartic Acid | Asp | D | GAC GAU |
| Cysteine | Cys | C | UGC UGU |
| Glutamic acid | Glu | E | GAA GAG |
| Glutamine | Gln | Q | CAA CAG |
| Glycine | Gly | G | GGA GGC GGG GGU |
| Histidine | His | H | CAC CAU |
| Isoleucine | Ile | I | AUA AUC AUU |
| Leucine | Leu | L | UUA UUG CUA CUC CUG CUU |
| Lysine | Lys | K | AAA AAG |
| Methionine | Met | M | AUG |
| Phenylalanine | Phe | F | UUC UUU |
| Proline | Pro | P | CCA CCC CCG CCU |
| Serine | Ser | S | ACG AGU UCA UCC UCG UCU |
| Threonine | Thr | T | ACA ACC ACG ACU |
| Tryptophan | Trp | W | UGG |
| Tyrosine | Tyr | Y | UAC UAU |
| Valine | Val | V | GUA GUC GUG GUU |

BACKGROUND ART

Tumor-specific drug delivery has the potential to minimize toxicity to normal tissues and improve the bioavailability of therapeutic agents to tumor cells (Hallahan et al., 1995b; Arap et al., 1998). Targeting ligands include antibodies and peptides that accumulate in tumors by specific binding to target molecules present on tumor vasculature, endothelial cells associated with tumor vasculature, and tumor cells. Effective target molecules are generally cell surface receptors or other molecules present at the exterior of tumor cells such that they are accessible to targeting ligands (Hallahan et al., 2001a).

Existing site-specific drug delivery systems include ligands that recognize a tumor marker such as Her2/neu (v-erb-b2 avian erythroblastic leukemia viral oncogene homologue 2), CEA (carcinoembryonic antigen; Ito et al., 1991), and breast cancer antigens (Manome et al., 1994; Kirpotin et al., 1997; Becerril et al., 1999). See also PCT International Publication No. WO 98/10795. In an effort to identify ligands that are capable of targeting to multiple tumor types, targeting ligands have been developed that bind to target molecules present on tumor vasculature (Baillie et al., 1995; Pasqualini & Ruoslahti, 1996; Arap et al., 1998; Burg et al., 1999; Ellerby et al., 1999).

Despite these advances, current methods for targeted drug delivery are hindered by targeting ligands that also bind normal tissues and/or a lack of targeting ligands that bind multiple tumor types. Ideally, a targeting molecule should display specific targeting in the absence of substantial binding to normal tissues, and a capacity for targeting to a variety of tumor types and stages. Thus, there exists a long-felt need in the art for methods to achieve site-specific, tumoral delivery of therapeutic and/or diagnostic agents.

To meet this need, the presently disclosed subject matter provides a method for identifying ligands that bind to irradiated tumors. Such ligands are useful for x-ray guided drug delivery, among other applications.

SUMMARY

The presently disclosed subject matter provides methods and compositions that can be used to target radiation-inducible neoantigens. In one embodiment, a radiation-inducible neoantigen is selected from the group consisting of P-selectin, E-selectin, Endoglin, $\alpha_{2b}\beta_3$ integrin, and $\alpha_v\beta_3$ integrin.

The presently disclosed subject matter also provides a method for screening a plurality of phage-displayed antibodies for an ability to bind to a radiation-inducible neoantigen present on a cell. In one embodiment, the method comprises (a) contacting the cell with a first solution, the first solution comprising the plurality of phage-displayed antibodies; (b) isolating a second solution, the second solution comprising those phage-displayed antibodies that do not bind to the cell; (c) removing any phage-displayed antibodies bound to the cell; (d) treating the cell with radiation, wherein the treating results in a radiation-inducible neoantigen being present on the cell; (e) contacting the cell with the second solution; and (f) detecting binding of a phage-displayed antibody to the radiation-inducible neoantigen on the cell.

The methods and compositions of the presently disclosed subject matter employ or comprise antibodies or antibody fragments. In one embodiment, an antibody or antibody fragment is a single chain fragment variable (scFv) antibody. In another embodiment, an antibody or antibody fragment is a human Fab antibody. Thus, in representative embodiments, the methods and compositions of the presently disclosed subject matter employ or comprise scFv antibodies or human Fab antibodies.

In one embodiment, the phage-displayed antibody is humanized. In another embodiment, the phage-displayed antibody is encoded by a nucleic acid encoding an scFv antibody having an amino acid sequence selected from the group consisting of SEQ ID NOs: 18, 20, 22, and 24, or by a nucleic acid sequence that is selected from the group consisting of SEQ ID NOs: 17, 19, 21, and 23. In another embodiment, the phage-displayed antibody has an amino acid sequence that is selected from the group consisting of SEQ ID NOs: 18, 20, 22, and 24. In still another embodiment, the phage-displayed antibody further comprises an epitope tag. In one embodiment, the epitope tag is selected from the group consisting of a c-myc tag and a histidine tag.

The present method can be used to screen for phage-displayed antibodies that bind to radiation-inducible neoantigens present on any cell. In one embodiment, the cell is selected from the group consisting of a tumor cell and a vascular endothelial cell. In one embodiment, the vascular endothelial cell is present within tumor microvasculature. In one embodiment, the radiation-inducible neoantigen is selected from the group consisting of P-selectin, E-selectin, Endoglin, $\alpha_{2b}\beta_3$ integrin, and $\alpha_v\beta_3$ integrin.

In one embodiment of the present method, the detecting step is accomplished using a technique selected from the group consisting of ELISA, BIACORE, Western blotting, immunohistochemistry, fluorometric microvolume assay technology, mass spectroscopy, MALDI-MS, and MALDI-TOF.

The presently disclosed subject matter also provides a method of targeting a therapeutic agent to a target tissue. In one embodiment, the method comprises (a) providing an immunoconjugate composition comprising a therapeutic agent and an antibody or antibody fragment, wherein the antibody or antibody fragment is capable of binding to a radiation-inducible neoantigen; (b) irradiating the target tissue to induce expression of the radiation-inducible neoantigen in the target tissue; and (c) contacting the irradiated target tissue with the immunoconjugate composition under conditions sufficient for binding of the antibody or antibody fragment to the radiation-inducible neoantigen, whereby the therapeutic agent is targeted to the target tissue. In one embodiment, the target tissue is a tumor or tumor vasculature. In another embodiment, the target tissue is present within a subject. In one embodiment, the subject is a mammal.

The presently disclosed subject matter also provides a method for suppressing the growth of a tumor in a subject. In one embodiment, the method comprises (a) exposing the tumor to radiation, whereby a radiation-inducible neoantigen is expressed; and (b) administering to the subject bearing the tumor an effective amount of an immunoconjugate composition, the immunoconjugate composition comprising a therapeutic agent and an antibody or antibody fragment that binds to a radiation-inducible neoantigen, whereby growth of the tumor is suppressed.

The present method can be used to suppress the growth of any tumor in any subject. In one embodiment, the tumor is selected from the group consisting of benign intracranial meningiomas, arteriovenous malformation, angioma, macular degeneration, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, solid tumors, solid tumor metastases, angiofibromas, retrolental fibroplasia, hemangiomas, Karposi's sarcoma, head and neck carcinomas, and combinations thereof. In one embodiment, the subject is a mammal.

The presently disclosed subject matter also provides a single chain fragment variable (scFv) antibody isolated by the disclosed methods.

The presently disclosed subject matter also provides immunoconjugate compositions for use in the disclosed methods. In one embodiment, the immunoconjugate composition comprises an antibody or antibody fragment that binds to a radiation-inducible neoantigen. In another embodiment, the immunoconjugate composition comprises a liposome or a nanoparticle. In one embodiment, the nanoparticle further comprises a fluorescent label.

In one embodiment, the immunoconjugate composition is polyvalent. In this embodiment, the immunoconjugate composition comprises a plurality of single chain fragment variable (scFv) antibodies, the plurality comprising at least two single chain fragment variable (scFv) antibodies that bind to different epitopes. In this embodiment, the plurality of single chain fragment variable (scFv) antibodies comprises at least one scFv antibody that binds to an antigen present on a tumor cell and at least one scFv antibody that binds to an antigen present on a vascular endothelial cell.

In another embodiment of the presently disclosed subject matter, the immunoconjugate composition further comprises a therapeutic agent. In one embodiment, the therapeutic agent is selected from the group consisting of a virus, a radionuclide, a cytotoxin, a therapeutic gene, and a chemotherapeutic agent.

In another embodiment of the present immunoconjugate composition, the single chain fragment variable (scFv) antibody is humanized. In another embodiment, the single chain fragment variable (scFv) antibody is encoded by a nucleic acid encoding an scFv antibody having an amino acid sequence selected from the group consisting of SEQ ID NOs: 18, 20, 22, and 24, or by a nucleic acid molecule comprising a nucleic acid sequence selected from the group consisting of SEQ ID NOs: 17, 19, 21, and 23. In still another embodiment, the single chain fragment variable (scFv) antibody comprises an amino acid sequence selected from the group consisting of SEQ ID NOs: 18, 20, 22, and 24. In one embodiment, the immunoconjugate composition is provided in a pharmaceutically acceptable carrier.

In another embodiment, the immunoconjugate composition further comprises a detectable label. In one embodiment, the detectable label is detectable in vivo. In this embodiment, the detectable label comprises a label that can be detected using magnetic resonance imaging, scintigraphic imaging, ultrasound, or fluorescence. In one embodiment, the label that can be detected using scintigraphic imaging comprises a radionuclide label. In this embodiment, the radionuclide label comprises $^{131}$I or $^{99m}$Tc.

The presently disclosed subject matter also provides a polyvalent immunoconjugate composition, the polyvalent immunoconjugate composition comprising a plurality of single chain fragment variable (scFv) antibodies, wherein the plurality of single chain fragment variable (scFv) antibodies bind to a plurality of different epitopes, and wherein at least one of the epitopes is present on a radiation-inducible neoantigen. In one embodiment, at least one of the plurality of different epitopes is present on a vascular endothelial cell.

The presently disclosed subject matter also provides a method for prioritizing the binding of a plurality of antibodies or antibody fragments to a target tissue in a subject. In one embodiment, the method comprises (a) providing a plurality of antibodies or antibody fragments that bind to the target, wherein the plurality of antibodies or antibody fragments comprise at least two different antibodies or antibody fragments that bind a radiation-inducible neoantigen within the target tissue, and wherein the at least two different antibodies or antibody fragments are distinguishable from each other; (b) irradiating the target tissue, whereby the radiation-inducible neoantigens are expressed within the target tissue; (c) administering the plurality of antibodies or antibody fragments to the subject under conditions sufficient to allow the plurality of antibodies or antibody fragments to bind to the radiation-inducible neoantigens in the target tissue; (d) isolating a portion of the target tissue from the subject, wherein the portion comprises the radiation-inducible neoantigens to which the plurality of antibodies or antibody fragments bind; (e) identifying the at least two different antibodies or antibody fragments in the portion of the target tissue; (f) comparing a relative selectivity and an affinity for the radiation-inducible neoantigens of the at least two different antibodies or antibody fragments identified in step (e) in the irradiated target tissue; and (g) assigning a priority to the at least two different antibodies or antibody fragments based on the comparing of step (f). In one embodiment, the subject is a mammal. In one embodiment, the target tissue is a tumor or tumor vasculature. In one embodiment, the antibodies or antibody fragments are single chain fragment variable (scFv) antibodies. In one embodiment, the single chain fragment variable (scFv) antibodies are humanized. In one embodiment of the present method, the at least two different antibodies or antibody fragments that bind to at least two different radiation-inducible neoantigens are distinguishable from each other based upon differences in molecular weight.

In another embodiment of the present method, the at least two different antibodies or antibody fragments that bind to at least two different radiation-inducible neoantigens within the target tissue each further comprises a different detectable label, such that the antibodies or antibody fragments that bind to different radiation-inducible neoantigens can be distinguished from each other. In one embodiment, the different detectable labels are fluorescent labels, and each fluorescent label has a different excitation or emission spectrum, such that the different antibodies can be distinguished from each other.

In another embodiment of the present method, the administering is by intravenous injection or intratumoral injection. In another embodiment, the portion of the target tissue from the subject is a tumor biopsy. In still another embodiment, the detecting is by mass spectroscopy.

The presently disclosed subject matter also provides methods of detecting a tumor in a subject. In one embodiment, the method comprises (a) exposing a suspected tumor to ionizing radiation; (b) administering to the subject an immunoconjugate composition, wherein the immunoconjugate composition comprises an antibody or antibody fragment that binds to a radiation-inducible neoantigen and a detectable label; and (c) detecting the detectable label, whereby a tumor is diagnosed. In another embodiment, the method comprises (a) exposing a suspected tumor to ionizing radiation; (b) removing a portion of the suspected tumor; (c) contacting an immunoconjugate composition with the suspected tumor in vitro, wherein the immunoconjugate composition comprises an antibody or antibody fragment that binds to a radiation-inducible neoantigen and a detectable label; and (d) detecting the detectable label, whereby a tumor is diagnosed.

Accordingly, it is an object of the presently disclosed subject matter to provide a method for screening a plurality of antibodies or antibody fragments for an ability to bind to a radiation-inducible neoantigen present on a cell. This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following description and non-limiting Examples.

BRIEF DESCRIPTION OF THE FIGURES

In FIG. 4A, a representative E-tagged scFv specific for an antigen (in one embodiment, a radiation-inducible neoantigen) is depicted. The presence of the E-tag allows the E-tagged scFv antibody to be affinity purified by using an anti-E-tag monoclonal antibody conjugated to a solid support (for example, a bead). The scFv depicted in this Figure also has its cognate antigen bound to it, which would allow the affinity purification of both the scFv and the antigen.

FIG. 4B depicts mass spectrophotometric analyses of lysates of an antibody (G12) immunoprecipitated with the beads depicted in FIG. 4A. The precipitated antibodies were placed directly onto MALDI plates and separated by mass spectroscopy. Shown are the spectra from negative control cells with no antibody (left panel) and an antibody precipitated by monoclonal Anti-E antibody beads (right panel).

BRIEF DESCRIPTION OF THE SEQUENCE LISTING

Figure 1:
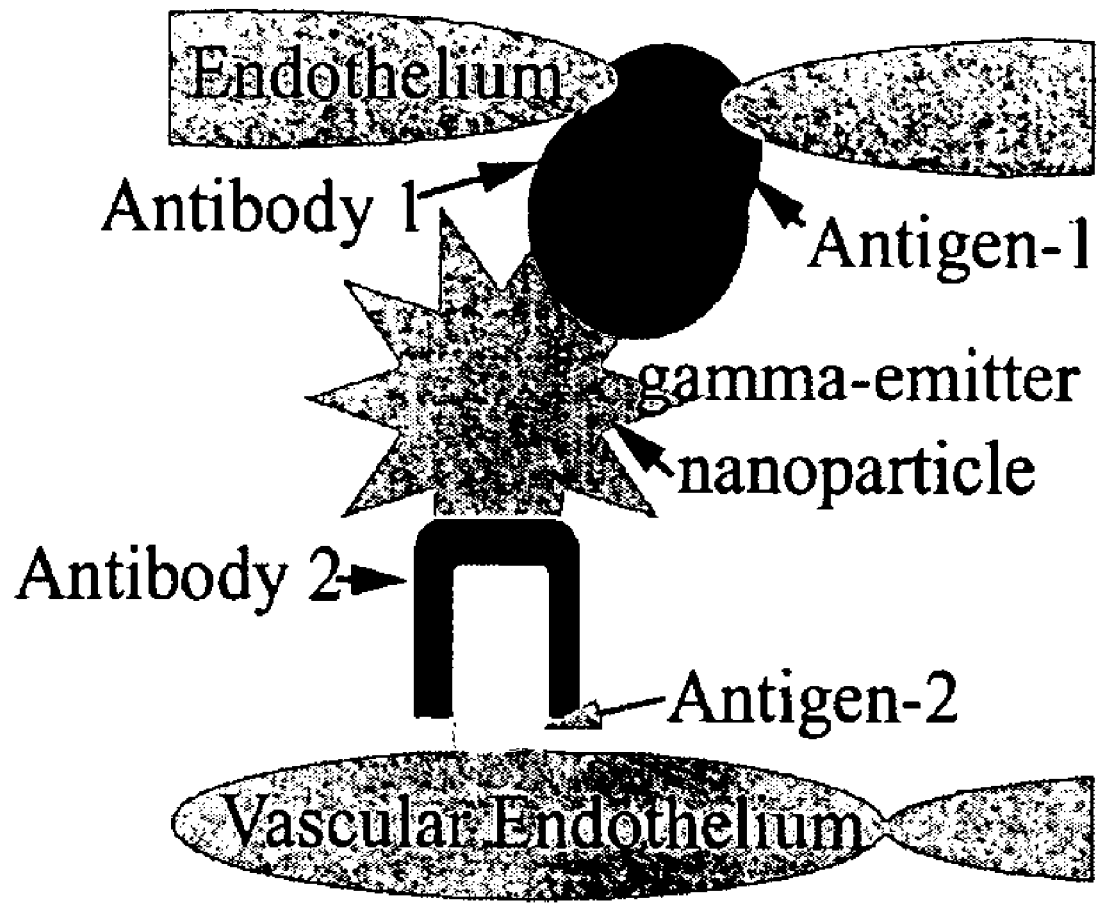
FIG. 1 depicts a polyvalent immunoconjugate. In this Figure, the polyvalent immunoconjugate consists of a nanoparticle to which two antibodies (Antibody 1 and Antibody 2) and one therapeutic agent (in this case, a gamma emitter) are complexed.

SEQ ID NOs: 1-13 are the amino acid sequences of representative peptide ligands that bind to radiation-inducible neoantigens.

SEQ ID NOs: 14 and 15 are the nucleotide sequences of PCR primers that are used to amplify the nucleic acids encoding recombinant phage.

SEQ ID NO: 16 is the amino acid sequence of a peptide that binds to the radiation-inducible neoantigen, $\alpha_{2b}\beta_3$ integrin.

SEQ ID NOs: 17-24 are the nucleic acid and amino acid sequences of representative scFv antibodies that bind to radiation-inducible neoantigens. Among SEQ ID NOs: 17-24, the odd numbered sequences are nucleic acid sequences, and the even numbered sequences are the amino acid sequences that are encoded by the immediately previous SEQ ID NO. Thus, SEQ ID NO: 18 is the amino acid sequence of the scFv antibody encoded by SEQ ID NO: 17; SEQ ID NO: 20 is the amino acid sequence of the scFv antibody encoded by SEQ ID NO: 19; etc.

SEQ ID NO: 25 is the amino acid sequence of the E tag epitope tag.

SEQ ID NOs: 26-34 are the amino acid sequences of peptides that are used in binding assays targeting the radiation-inducible neoantigen $\alpha_{2b}\beta_3$ integrin. SEQ ID NOs: 26-30 are the amino acid sequences of certain derivatives of SEQ ID NO: 16. SEQ ID NOs: 31-34 are the amino acid sequences of control peptides. These SEQ ID NOs. are summarized below:

| SEQ ID NO: | AMINO ACID SEQUENCE |
|---|---|
| 26 | HHLGGAKQAGDV-SGSGS |
| 27 | SGSGS-HHLGGAKQAGDVC |
| 28 | HHLGGAKQAGDV-SGSGS-YYYYY |
| 29 | HHLGGAKQAGDV-SGSGSC |
| 30 | HHLGGAKQAGDV-SGSGSK |
| 31 | SGSGS |
| 32 | SGSGS-YYYYY |
| 33 | SGSGSGSSGSGSSGSGS-YYYYY |
| 34 | SGSGSSGSGSGS-SGSGS |

DETAILED DESCRIPTION

I. Definitions

All technical and scientific terms used herein, unless otherwise defined below, are intended to have the same meaning as commonly understood by one of ordinary skill in the art; references to techniques employed herein are intended to refer to the techniques as commonly understood in the art, including variations on those techniques or substitutions of equivalent techniques which would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" mean "one or more" when used in this application, including the claims.

As used herein, unless specifically indicated otherwise, the word "or" is used in the "inclusive" sense of "and/or" and not the "exclusive" sense of "either/or".

The term "ligand" as used herein refers to a molecule or other chemical entity having a capacity for binding to a target. A ligand can comprise a peptide, an oligomer, a nucleic acid (e.g., an aptamer), a small molecule (e.g., a chemical compound), an antibody or fragment thereof, a nucleic acid-protein fusion, and/or any other affinity agent.

The term "small molecule" as used herein refers to a compound, for example an organic compound, with a molecular weight in one example of less than about 1,000 daltons, in another example less than about 750 daltons, in another example less than about 600 daltons, and in yet another example less than about 500 daltons. A small molecule also has a computed log octanol-water partition coefficient that in one example is in the range of about −4 to about +14, and in another example is in the range of about −2 to about +7.5.

The term "control tissue" as used herein refers to a site suspected to substantially lack binding and/or accumulation of an administered ligand. For example, in accordance with the methods of the presently disclosed subject matter, control tissues include, but are not limited to a non-irradiated tumor, a non-cancerous tissue, and vascular endothelium that is either non-irradiated or not associated with a tumor.

The term "target tissue" as used herein refers to an intended site for accumulation of a ligand following administration to a subject. For example, the methods of the presently disclosed subject matter employ a target tissue comprising an irradiated tumor or the vasculature associated with an irradiated tumor.

The terms "target" or "target molecule" as used herein each refer to any substance that is specifically bound by a ligand. Thus, the term "target molecule" encompasses macromolecules including, but not limited to proteins, nucleic acids, carbohydrates, lipids, and complexes or combinations thereof.

As used herein, the terms "radiation-inducible target", "radiation-inducible tumor target", and "radiation-inducible neoantigen" are used interchangeably and refer to a target molecule associated with a target tissue (for example, a tumor) for which the expression, localization, or ligand-binding capacity is induced by radiation. Such a target molecule can comprise a molecule at the surface of a tumor cell, within a tumor cell, or in the extracellular matrix surrounding a tumor cell. Alternatively, a target molecule can comprise a molecule present at the surface of or within a vascular endothelial cell, or at the surface of or within a blood component such as a platelet or a leukocyte. Radiation-inducible neoantigens include, but are not limited to P-selectin, E-selectin, Endoglin, $\alpha_{2b}\beta_3$ integrin, and $\alpha_v\beta_3$ integrin.

The term "induce", as used herein to refer to changes resulting from radiation exposure, encompasses activation of gene transcription or regulated release of proteins from cellular storage reservoirs to cell surfaces. Alternatively, induction can refer to a process of conformational change, also called activation, such as that displayed by the glycoprotein IIb/IIIa integrin receptor upon radiation exposure (Staba et al., 2000; Hallahan et al., 2001a). See also U.S. Pat. No. 6,159,443.

The terms "targeting" or "homing", as used herein to describe the in vivo activity of a ligand following administration to a subject, refer to the preferential movement and/or accumulation of a ligand in a target tissue as compared to a control tissue.

The terms "selective targeting" of "selective homing" as used herein each refer to a preferential localization of a ligand that results in an amount of ligand in a target tissue that is in one example about 2-fold greater than an amount of ligand in a control tissue, in another example about 5-fold or greater, and in yet another example about 10-fold or greater. The terms "selective targeting" and "selective homing" also refer to binding or accumulation of a ligand in a target tissue concomitant with an absence of targeting to a control tissue, in one embodiment the absence of targeting to all control tissues.

The term "absence of targeting" is used herein to describe substantially no binding or accumulation of a ligand in all control tissues where an amount of ligand would be expected to be detectable, if present.

The terms "targeting ligand", "targeting molecule", "homing ligand", and "homing molecule" as used herein each refer to a ligand that displays targeting activity. In one embodiment, a targeting ligand displays selective targeting. In another embodiment, a targeting ligand comprises a phage-displayed antibody (for example, a phage-displayed scFv antibody or a phage-displayed antibody fragment such as an Fab antibody).

The term "binding" refers to an affinity between two molecules, for example, a ligand and a target molecule. As used herein, the term "binding" refers to a specific binding of one molecule for another in a mixture of molecules. The binding of a ligand to a target molecule can be considered specific if the binding affinity is about $1\times10^4$ M$^{-1}$ to about $1\times10^6$ M$^{-1}$ or greater. Thus, the binding of an antibody to an antigen can be thought of as having at least two components: an affinity, which refers to the strength at which the antibody binds an antigen, and a specificity, which refers to the level of cross-reactivity an antibody displays between closely related antigens.

The phrase "specifically (or selectively) binds", when referring to the binding capacity of a ligand, refers to a binding reaction which is determinative of the presence of the protein in a heterogeneous population of proteins and other biological materials. The phrase "specifically binds" also refers to selective targeting, as defined herein above.

The phases "substantially lack binding" or "substantially no binding", as used herein to describe binding of a ligand in a control tissue, refers to a level of binding that encompasses non-specific or background binding, but does not include specific binding.

The term "tumor" as used herein refers to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, head and neck (e.g. head and neck squamous cell carcinomas; HNSCC) and meninges (e.g., astrocytomas, gliomas, glioblastomas, retinoblastomas, neuromas, neuroblastomas, Schwannomas and meningiomas). The term "tumor" also encompasses solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas.

The term "subject" as used herein refers to any invertebrate or vertebrate species. The methods of the presently disclosed subject matter are particularly useful in the treatment and diagnosis of warm-blooded vertebrates. Thus, the presently disclosed subject matter concerns mammals and birds. More particularly contemplated is the treatment and/or diagnosis of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, contemplated is the treatment of livestock, including, but not limited to, domesticated swine (pigs and hogs), ruminants, horses, poultry, and the like.

The term "about", as used herein when referring to a measurable value such as an amount of weight, time, dose (e.g. radiation dose), etc. is meant to encompass variations of in one example ±20% or ±10%, in another example ±5%, in another example ±1%, and in yet another example ±0.1% from the specified amount, as such variations are appropriate to perform the disclosed methods.

II. X-Ray Guided Drug Delivery

Ionizing radiation induces proteins in tumor vascular endothelium through transcriptional induction and/or post-translational modification of cell adhesion molecules such as integrins (Hallahan et al., 1995a; Hallahan et al., 1996; Hallahan et al., 1998; Hallahan & Virudachalam, 1999). For example, radiation induces activation of the integrin $\alpha_{2b}\beta_3$, also called the fibrinogen receptor, on platelets. Radiation also induces the translocation of P-selectin from storage reservoirs in vascular endothelium to the vascular lumen. The induced molecules can serve as binding sites for targeting ligands, for example, scFv antibodies.

Several radiation-inducible molecules within tumor blood vessels have been identified and characterized including, but not limited to P-selectin, E-selectin, Endoglin, $\alpha_{2b}\beta_3$ integrin, and $\alpha_v\beta_3$ integrin. $^{131}$I-labeled fibrinogen binds specifically to tumors following exposure to ionizing radiation (U.S. Pat. No. 6,159,443). Peptides within fibrinogen that bind to the radiation-inducible $\alpha_{2b}\beta_3$ integrin include HHLGGAKQAGDV (SEQ ID NO: 16) and the RGD peptide (Hallahan et al., 2001a).

The presently disclosed subject matter includes a study of the targeting activity of ligands that bind to radiation-inducible neoantigens (for example, ligands that bind to P-selectin or the $\alpha_{2b}\beta_3$ integrin) in tumor-bearing subjects. Example 1 describes x-ray-guided drug delivery in animal models using ligand-conjugated liposomes and microspheres. Clinical trials using a radiolabeled $\alpha_{2b}\beta_3$ ligand support the feasibility of x-ray-guided drug delivery in humans, as described in Example 2. See also Hallahan et al., 2001a.

III. Identification of Ligands that Bind Irradiated Tumors

Approaches for optimizing peptide binding affinity and specificity have included modification of peptide conformation and addition of flanking amino acids to extend the minimal binding motif. For example, amino acids C-terminal to the RGD sequence are differentially conserved in RGD-containing ligands, and this variation correlates with differences in binding specificity (Cheng et al., 1994; Koivunen et al., 1994). Similarly, cyclization of a prototype RGD peptide to restrict its conformational flexibility improved interaction of the peptide with the vitronectin receptor, yet nearly abolished interaction with the fibronectin receptor (Pierschbacher & Ruoslahti, 1987).

Despite conservation of binding motifs among ligands that bind irradiated tumors and recognition of factors that can influence ligand binding, design of peptide sequences for improved targeting activity is yet unpredictable. Approaches for identifying such peptides have therefore relied on high volume screening methods to select effective motifs from peptide libraries (Koivunen et al., 1993; Healy et al., 1995). However, the utility of in vitro-selected peptides is unpredictable in so far as peptide-binding properties are not consistently recapitulated in vivo. To obviate these challenges, the presently disclosed subject matter provides a method for in vivo selection of targeting ligands, described further herein below.

Using the in vivo selection method disclosed herein, novel targeting ligands were identified that can be used for x-ray-guided drug delivery. Representative peptide ligands are set forth as SEQ ID NOs: 1-13. Representative scFv antibody ligands are set forth as SEQ ID NOs: 18, 20, 22, and 24 (encoded by SEQ ID NOs: 17, 19, 21, and 23). The novel ligands display improved specificity of binding to irradiated tumors and are effective for targeting using low dose irradiation. The disclosed targeting ligands also offer benefits including moderate cost of preparation and ease of handling.

III.A. Libraries

As used herein, the term "library" means a collection of molecules. A library can contain a few or a large number of different molecules, varying from at least two molecules to several billion molecules or more. A molecule can comprise a naturally occurring molecule, or a synthetic molecule that is not found in nature. Optionally, a plurality of different libraries can be employed simultaneously for in vivo screening.

Representative libraries include but are not limited to a peptide library (U.S. Pat. Nos. 6,156,511, 6,107,059, 5,922,545, and 5,223,409), an oligomer library (U.S. Pat. Nos. 5,650,489 and 5,858,670), an aptamer library (U.S. Pat. Nos. 6,180,348 and 5,756,291), a small molecule library (U.S. Pat. Nos. 6,168,912 and 5,738,996), a library of antibodies or antibody fragments (for example, an scFv library or an Fab antibody library; U.S. Pat. Nos. 6,174,708, 6,057,098, 5,922,254, 5,840,479, 5,780,225, 5,702,892, and 5,667,988), a library of nucleic acid-protein fusions (U.S. Pat. No. 6,214,553), and a library of any other affinity agent that can potentially bind to an irradiated tumor (e.g., U.S. Pat. Nos. 5,948,635, 5,747,334, and 5,498,538). In one embodiment, a library is a phage-displayed antibody library. In another embodiment, a library is a phage-displayed scFv library. In another embodiment, a library is a phage-displayed Fab library. In still another embodiment, a library is a soluble scFv antibody library.

The molecules of a library can be produced in vitro, or they can be synthesized in vivo, for example by expression of a molecule in vivo. Also, the molecules of a library can be displayed on any relevant support, for example, on bacterial pili (Lu et al., 1995) or on phage (Smith, 1985).

A library can comprise a random collection of molecules. Alternatively, a library can comprise a collection of molecules having a bias for a particular sequence, structure, conformation, or in the case of an antibody library, can be biased in favor of antibodies that bind to a particular antigen or antigens (for example, a radiation-inducible neoantigen). See e.g., U.S. Pat. Nos. 5,264,563 and 5,824,483. Methods for preparing libraries containing diverse populations of various types of molecules are known in the art, for example as described in U.S. Patents cited herein above. Numerous libraries are also commercially available.

III.A.1. Peptide Libraries

In one embodiment, a peptide library comprises peptides comprising three or more amino acids, in another example at least five, six, seven, or eight amino acids, in another example up to 50 amino acids or 100 amino acids, and in yet another example up to about 200 to 300 amino acids.

The peptides can be linear, branched, or cyclic, and can include non-peptidyl moieties. The peptides can comprise naturally occurring amino acids, synthetic amino acids, genetically encoded amino acids, non-genetically encoded amino acids, and combinations thereof.

A biased peptide library can also be used, a biased library comprising peptides wherein one or more (but not all) residues of the peptides are constant. For example, an internal residue can be constant, so that the peptide sequence is represented as:

$(XAA_1)_m$-$(AA)_1$-$(XAA_2)_n$ where $XAA_1$ and $XAA_2$ are any amino acid, or any amino acid except cysteine, wherein $XAA_1$ and $XAA_2$ are the same or different amino acids, m and n indicate a number XAA residues, wherein m and n are independently chosen from the range of 2 residues to 20 residues in one embodiment, and from the range of 4 residues to 9 residues in another embodiment, and AA is the same amino acid for all peptides in the library. In one example, AA is located at or near the center of the peptide. More specifically, in one example m and n are not different by more than 2 residues; in another example m and n are equal.

In one embodiment, a library is employed in which AA is tryptophan, proline, or tyrosine. In another embodiment, AA is phenylalanine, histidine, arginine, aspartate, leucine, or isoleucine. In another embodiment, AA is asparagine, serine, alanine, or methionine. In still another embodiment, AA is cysteine or glycine.

A biased library used for in vivo screening also includes a library comprising molecules previously selected by in vitro screening methods. See Example 8.

In one embodiment of the presently disclosed subject matter, the method for in vivo screening is performed using a phage peptide library. Phage display is a method to discover peptide ligands while minimizing and optimizing the structure and function of proteins. Phage are used as a scaffold to display recombinant libraries of peptides and provide a vehicle to recover and amplify the peptides that bind to putative receptor molecules in vivo. In vivo phage selection simultaneously provides positive and subtractive screens based on the spatial separation of normal tissues and tumors. Phage that specifically bind the vasculature of normal tissues are removed while specific phage that bind target molecules present in irradiated tumors are enriched through serial rounds of bioscreening.

The T7 phage has an icosahedral capsid made of 415 proteins encoded by gene 10 during its lytic phase. The T7 phage display system has the capacity to display peptides up to 15 amino acids in size at a high copy number (415 per phage). Unlike filamentous phage display systems, peptides displayed on the surface of T7 phage are not capable of peptide secretion. T7 phage also replicate more rapidly and are extremely robust when compared to other phage. The stability allows for bioscreening selection procedures that require persistent phage infectivity. Accordingly, the use of T7-based phage display is an aspect of one embodiment of the presently disclosed subject matter. Example 4 describes a representative method for preparation of a T7 phage peptide library that can be used to perform the in vivo screening methods disclosed herein.

A phage peptide library to be used in accordance with the screening methods of the presently disclosed subject matter can also be constructed in a filamentous phage, for example M13 or an M13-derived phage. In one embodiment, the encoded antibodies are displayed at the exterior surface of the phage, for example by fusion to the product of M13 gene III. Methods for preparing M13 libraries can be found in Sambrook & Russell, 2001, among other places.

III.A.2. Phage Antibody Libraries

In one embodiment, a ligand that binds to a radiation-inducible neoantigen is an antibody, or a fragment thereof. To identify antibodies and fragments thereof that bind to radiation-inducible neoantigens, libraries can be screened using the methods disclosed herein. Libraries that can be screened using the disclosed methods include, but are not limited to libraries of phage-displayed antibodies and antibody fragments, and libraries of soluble antibodies and antibody fragments.

"Fv" is the minimum antibody fragment that contains a complete antigen recognition and binding site. In a two-chain Fv species, this region consists of a dimer of one heavy and one light chain variable domain in tight, non-covalent association. In a single-chain Fv species (scFv), one heavy and one light chain variable domain can be covalently linked by a flexible peptide linker such that the light and heavy chains can associate in a "dimeric" structure analogous to that in a two-chain Fv species. It is in this configuration that the three complementarity-determining regions (CDRs) of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv, see Pluckthun, 1994.

The term "antibodies and fragments thereof", and grammatical variations thereof, refers to immunoglobulin molecules and immunologically active portions of immunoglobulin molecules; i.e., molecules that contain an antigen-binding site that specifically bind an antigen. As such, the term refers to immunoglobulin proteins, or functional portions thereof, including polyclonal antibodies, monoclonal antibodies, chimeric antibodies, hybrid antibodies, single chain antibodies (e.g., a single chain antibody represented in a phage library), mutagenized antibodies, humanized antibodies, and antibody fragments that comprise an antigen binding site (e.g., Fab and Fv antibody fragments). Thus, "antibodies and fragments thereof" include, but are not limited to monoclonal, chimeric, recombinant, synthetic, semi-synthetic, or chemically modified intact antibodies having for example Fv, Fab, scFv, or F(ab)₂ fragments.

The immunoglobulin molecules of the presently disclosed subject matter can be of any type (e.g., IgG, IgE, IgM, IgD, IgA and IgY), class (e.g., IgG1, IgG2, IgG3, IgG4, IgA1 and IgA2), or subclass of immunoglobulin molecule. In one embodiment, the antibodies are human antigen-binding antibody fragments of the presently disclosed subject matter and include, but are not limited to, Fab, Fab' and F(ab')₂, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, can comprise the variable region(s) alone or in combination with the entirety or a portion of the following: hinge region, CH1, CH2, and CH3 domains. Also included in the presently disclosed subject matter are antigen-binding fragments comprising any combination of variable region(s) with a hinge region, CH1, CH2, and CH3 domains.

The antibodies and fragments thereof of the presently disclosed subject matter can be from any animal origin including birds and mammals. For example, the antibodies can be human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598.

In another embodiment of the presently disclosed subject matter, an antibody library (for example, a library of scFv antibodies) can be used to perform the disclosed screening methods. In this embodiment, a ligand that binds to an irradiated tumor is an antibody or a fragment thereof that binds a radiation-inducible neoantigen. Antibodies that bind radiation-inducible neoantigens can be identified by screening a phage antibody library, as described in Examples 8 and 16. Such a library can be constructed, for example, in M13 or an M13-derived phage. See e.g., U.S. Pat. Nos. 6,593,081; 6,225,447; 5,580,717; and 5,702,892, all incorporated by reference herein.

Phage-displayed recombinant antibodies are genetically cloned and expressed on the tip of the M13 bacteriophage (McCafferty et al., 1990). M13 phage infects *E. coli* that carry an F' episome (plasmid) and constantly produce and secrete intact M13 virus particles without lysing the host cell. The components of the M13 phage include phage DNA, coat proteins, gene III attachment proteins, and other proteins that are fused to the phage proteins. There are 3-5 copies of the gene III attachment proteins located on the exterior of the phage that are responsible for phage attachment to receptors on *E. coli* cells.

In one embodiment, M13 phage-displayed recombinant antibodies can be created by linking DNA from antibody-producing B lymphocytes to the phage gene III DNA using the pCANTAB vector (see Example 8). The proteins encoded by the antibody in gene III DNA are fused to one another to produce an antibody-gene III fusion protein. A bacteriophage carrying the gene fusion will simultaneously contain the antibody DNA and express an antibody molecule on the gene III protein.

A representative, non-limiting approach to obtain and characterize antigen-specific recombinant antibodies or antibody fragments (for example, scFv antibodies or human Fab antibodies) is as follows. Phage antibody selections can be performed using antigens immobilized on solid supports or biotinylated antigens and streptavidin magnetic beads. An aliquot of a phage antibody library can be applied to the antigen. Nonspecific phage antibodies are thereafter washed off of the antigen, and phage that encode bound antibodies can be eluted and used to infect *E. coli*. Infected *E. coli* can be plated and rescued with helper phage to produce an antigen-enriched phage antibody library. The antigen-enriched library (i.e., a library pre-selected for binding to a particular antigen of interest) can be used in a second round of selection for binding to the antigen. Subsequent rounds of selection on antigen and helper phage rescue can be used until the desired antigen-specific antibodies are obtained. Colonies stemming for phage antibody selections can be picked from agar plates manually or by using a colony picker (for example, the QPix2 Colony Picker from Genetix USA Inc., Boston, Mass., United States of America). Picked colonies can then transferred to appropriate vessels, for example microwell plates, and can be used to produce soluble recombinant antibodies. See e.g. Example 8.

Phage-displayed recombinant antibodies have several advantages over polyclonal antibodies or hybridoma-derived monoclonal antibodies. Phage-displayed antibodies can be generated within 8 days. Recombinant antibody clones can be easily selected by panning a population of phage-displayed antibodies against immobilized antigen (McCafferty et al., 1990). The antibody protein and antibody DNA are simultaneously contained in one phage particle (Better et al., 1988). Liters of phage-displayed recombinant antibodies can be produced inexpensively from bacterial culture supernatant and the phage antibodies can be used directly in immunoassays without purification. Phage display technology makes possible the direct isolation of monovalent scFv antibodies. The small size of scFv antibodies makes it the antibody format of choice for tumor penetration and rapid clearance from the blood (Adams et al., 1995; Adams, 1998; Yokota et al., 1992). The human phage antibody library can be used to develop antibodies suitable for clinical trials. These human scFv antibodies have entered clinical trials (Hoogenboom & Winter, 1992). The human phage antibody library can be used to develop antibodies suitable for clinical trials]. Anti-melanoma antibodies have been developed using these phage libraries (Cai & Garen, 1995), as well as antibodies to antigens found in ovarian carcinoma (Figini et al., 1998).

Using a phage-displayed approach for the production of antibodies, scFv antibody clones that bind to a radiation-inducible target are identified as disclosed herein. Fv regions are sequenced and bivalent functional reagents are designed and tested, for example using an assay as disclosed herein. Thus, an exemplary, but non-limiting, source for an antibody, or derivative or fragment thereof, is a recombinant phage-displayed antibody library.

The recombinant phage can comprise antibody encoding nucleic acids isolated from any suitable vertebrate species, including in alternative embodiments mammalian species such as human, mouse, and rat. Thus, in one embodiment the recombinant phage encode an antibody wherein both the variable and constant regions are encoded by nucleic acids isolated from the same species (for example, human, mouse, or rat). In another embodiment, the recombinant phage encode chimeric antibodies, wherein the phrase "chimeric antibodies" (and grammatical variations thereof) refers to antibodies having variable and constant domain regions that are derived from different species. For example, in one embodiment the chimeric antibodies are antibodies having murine variable domains and human constant domains.

The scFv antibodies of the presently disclosed subject matter also include humanized scFv antibodies. Humanized forms of non-human (for example, murine) scFv antibodies are chimeric scFv antibodies that contain minimal sequence derived from non-human immunoglobulins. Humanized scFv antibodies include human scFvs in which residues from a complementarity-determining region (CDR) are encoded by a nucleic acid encoding a CDR of a non-human species such as mouse, having the desired specificity, affinity, and capacity. In some instances, Fv framework residues of the human immunoglobulin are replaced by corresponding non-human residues. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; Presta, 1992). Thus, as used herein, the term "humanized" encompasses chimeric antibodies comprising a human constant region, including those antibodies wherein all of the residues are encoded by a human nucleic acid (see for example Shalaby et al., 1992; Mocikat et al., 1994).

III.B. In Vivo Screening for Ligands that Bind Irradiated Tumors

The presently disclosed subject matter provides a method for in vivo screening for ligands that bind irradiated tumors. As used herein, the term "in vivo screening" refers to a method of screening a library for selection of a ligand that homes to an irradiated tumor or the vasculature associated with an irradiated tumor.

The term "in vivo", as used herein to describe methods of screening or ligand selection, refers to contacting of one or more ligands to endogenous candidate target molecules, wherein the candidate target molecules are naturally present in a subject, or are present in a tumor in, or a tumor biopsy from, a subject, whether naturally occurring to experimentally induced, and the contacting occurs in the subject or in the biopsied tumor. By contrast, "in vitro" screening refers to contacting a library of candidate ligands with one or more isolated or recombinantly produced target molecules.

Thus, a method for screening as disclosed herein includes the steps of (a) contacting a cell with a first solution, the first solution comprising a plurality of phage-displayed antibodies; (b) isolating a second solution, the second solution comprising those phage-displayed antibodies that do not bind to the cell; (c) removing any phage-displayed antibodies bound to the cell; (d) treating the cell with radiation, wherein the treating results in a radiation-inducible neoantigen being present on the cell; (e) contacting the cell with the second solution; and (f) detecting binding of a phage-displayed antibody to the radiation-inducible neoantigen on the cell. In one embodiment, a phage-displayed antibody is a single chain fragment variable (scFv) antibody. In another embodiment, a phage-displayed antibody is an Fab antibody.

The term "administering to a subject", when used to describe provision of a library of molecules, is used in its broadest sense to mean that the library is delivered to the irradiated tumor. For example, a library can be provided to the circulation of the subject by injection or cannulization such that the molecules can pass through the tumor.

Alternatively or in addition, a library can be administered to an isolated tumor or tumor biopsy. Thus, a method for in vivo screening can also comprise: (a) exposing a tumor and a control tissue to ionizing radiation; (b) administering to the tumor and to the control tissue a library of diverse molecules; (c) detecting one or more molecules of the library that bind to the tumor and that substantially lack binding to the control tissue, whereby a molecule that binds an irradiated tumor is identified.

The in vivo screening methods of the presently disclosed subject matter can further comprise administering the library to isolated tumor cells or to isolated proteins prior to administering the library to a subject or to a tumor. For example, in vitro screening methods can be performed to select ligands that bind to particular tumor neoantigens, followed by performance of the in vivo screening methods as disclosed herein.

In one embodiment of the presently disclosed subject matter, the radiation treatment comprises administration of less than about 2 Grays (Gy) ionizing radiation. In another embodiment, the radiation treatment comprises at least about 2 Gy ionizing radiation, optionally about 2 Gy to about 3 Gy ionizing radiation, or about 2 Gy to about 6 Gy ionizing radiation. In an alternative embodiment, radiation treatment comprises about 10 Gy to about 20 Gy ionizing radiation.

The methods of the presently disclosed subject matter can be performed using any tumor-bearing subject or any subject suspected of having a tumor. In one embodiment a subject is a warm-blooded vertebrate, in another embodiment a mammal, and in still another embodiment a human.

In one embodiment of the presently disclosed subject matter, a library is administered to a tumor-bearing human subject following irradiation of the tumor. Methods and appropriate doses for administration of a library to a human subject are described in PCT International Publication No. WO 01/09611.

In another embodiment, a tumor is experimentally induced in a subject (for example, a mouse), the tumor comprising a human cell or cell line. A library is then administered to the tumor-bearing subject either prior to or subsequent to irradiation of the tumor, as described in Example 16.

Example 5 describes a representative procedure for in vivo screening of phage-displayed peptide ligands that bind to irradiated tumor vessels in accordance with the presently disclosed subject matter. Briefly, peptide binding was studied in tumor blood vessels of 2 distinct tumor models: (1) GL261 glioma, and (2) Lewis lung carcinoma. Tumors were irradiated with 3 Gy to facilitate identification of peptide sequences that bind tumors exposed to a minimal dose of ionizing radiation. Phage were administered by tail vein injection into tumor bearing mice following irradiation. Phage were recovered from the tumor thereafter. Following multiple rounds of sequential in vivo binding to irradiated tumors, phage were recovered and individual phage were randomly picked and sequenced.

Example 9 describes a representative procedure for in vivo screening of phage-displayed ligands comprising single chain antibodies. The library used for in vivo screening was a biased library in that a pool of antibody ligands that bind to radiation-inducible antigens were pre-selected in vitro. However, a library need not be pre-selected in vitro to be used in the methods disclosed herein.

III.C. Recovery of Targeting Ligands

Methods for identifying targeting ligands that bind an irradiated tumor are selected based on one or more characteristics common to the molecules present in the library. For example, mass spectrometry and/or gas chromatography can be used to resolve molecules that home to an irradiated tumor. Thus, where a library comprises diverse molecules based generally on the structure of an organic molecule, determining the presence of a parent peak for the particular molecule can identify a ligand that binds a radiation-inducible target molecule. The use of matrix-assisted laser desorption/ionization coupled mass spectrometry (MALDI-MS) to identify antibody ligands that bind to radiation-inducible neoantigens is described in more detail herein below.

If desired, a ligand can be linked to a tag, which can facilitate recovery or identification of the molecule. A representative tag is an oligonucleotide or a small molecule such as biotin. See e.g., Brenner & Lerner, 1992 and U.S. Pat. No. 6,068,829. Alternatively, a tag can comprise an epitope for which an antibody is commercially available. These so-called epitope tags include, but are not limited to histidine tags, c-myc tags, and the E tag encoded by, for example, pCANTAB 5E from Amersham Biosciences (Piscataway, N.J., United States of America). Histidine tags (also called 6xHis tags) can be purified, for example, using nickel-nitrilotriacetic acid (Ni-NTA) Agarose available from Qiagen Inc. (Valencia, Calif., United States of America). Epitopes from c-myc include the sequence recognized by the monoclonal antibody 9E10, which is produced by a hybridoma (MYC 1-9E10.2) available from the American Type Culture Collection (Manassas, Va., United States of America). See also Evan et al., 1985 and Van Ewijk et al., 1997, each of which is incorporated by reference in its entirety. Polypeptides that comprise Amersham's E tag (GAPVPYPDPLEPR; SEQ ID NO: 25) can be purified using reagents and protocols supplied by the manufacturer. In one embodiment, an scFv antibody of the presently disclosed subject matter comprises an epitope tag.

In addition, a tag can be a support or surface to which a molecule can be attached. For example, a support can be a biological tag such as a virus or virus-like particle such as a bacteriophage ("phage"); a bacterium; or a eukaryotic cell such as yeast, an insect cell, or a mammalian cell (e.g., an endothelial progenitor cell or a leukocyte); or can be a physical tag such as a liposome or a microbead. In one embodiment, a support can have a diameter less than about 10 µm to about 50 µm in its shortest dimension, such that the support can pass relatively unhindered through the capillary beds present in the subject and not occlude circulation. In addition, a support can be nontoxic and biodegradable, particularly where the subject used for in vivo screening is not sacrificed for isolation of library molecules from the tumor. Where a molecule is linked to a support, the part of the molecule suspected of being able to interact with a target in a cell in the subject can be positioned so as be able to participate in the interaction.

III.D. Peptide Ligands

A targeting peptide of the presently disclosed subject matter can be subject to various changes, substitutions, insertions, and deletions where such changes provide for certain advantages in its use. Thus, the term "peptide" encompasses any of a variety of forms of peptide derivatives, that include amides, conjugates with proteins, cyclized peptides, polymerized peptides, conservatively substituted variants, analogs, fragments, peptoids, chemically modified peptides, and peptide mimetics. The terms "targeting peptide" or "peptide ligand" each refer to a peptide as defined herein above that binds to an irradiated tumor. The modifications disclosed herein can also be applied as desired and as appropriate to antibodies, including scFv antibodies.

Peptides of the presently disclosed subject matter can comprise naturally occurring amino acids, synthetic amino acids, genetically encoded amino acids, non-genetically encoded amino acids, and combinations thereof. Peptides can include both L-form and D-form amino acids.

Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

The term "conservatively substituted variant" refers to a peptide comprising an amino acid residue sequence substantially identical to a sequence of a reference ligand of radiation inducible target in which one or more residues have been conservatively substituted with a functionally similar residue and which displays the targeting activity as described herein. The phrase "conservatively substituted variant" also includes peptides wherein a residue is replaced with a chemically derivatized residue, provided that the resulting peptide displays targeting activity as disclosed herein.

Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Peptides of the presently disclosed subject matter also include peptides comprising one or more additions and/or deletions or residues relative to the sequence of a peptide whose sequence is disclosed herein, so long as the requisite targeting activity of the peptide is maintained. The term "fragment" refers to a peptide comprising an amino acid residue sequence shorter than that of a peptide disclosed herein.

Additional residues can also be added at either terminus of a peptide for the purpose of providing a "linker" by which the peptides of the presently disclosed subject matter can be conveniently affixed to a label or solid matrix, or carrier. Amino acid residue linkers are usually at least one residue and can be 40 or more residues, more often 1 to 10 residues, but do alone not constitute radiation inducible target ligands. Typical amino acid residues used for linking are tyrosine, cysteine, lysine, glutamic and aspartic acid, or the like. In addition, a peptide can be modified by terminal-$NH_2$ acylation (e.g., acetylation, or thioglycolic acid amidation) or by terminal-carboxylamidation (e.g., with ammonia, methylamine, and the like terminal modifications). Terminal modifications are useful, as is well known, to reduce susceptibility by proteinase digestion, and therefore serve to prolong half-life of the peptides in solutions, particularly biological fluids where proteases can be present.

Peptide cyclization is also a useful terminal modification because of the stable structures formed by cyclization and in view of the biological activities observed for such cyclic peptides as described herein. An exemplary method for cyclizing peptides is described by Schneider & Eberle, 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxyl termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

The term "peptoid" as used herein refers to a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), a thiopeptide bond (CS—NH), and an N-modified bond (—NRCO—). See e.g. Corringer et al., 1993; Garbay-Jaureguiberry et al., 1992; Tung et al., 1992; Urge et al., 1992; Pavone et al., 1993.

Peptides of the presently disclosed subject matter, including peptoids, can be synthesized by any of the techniques that are known to those skilled in the art of peptide synthesis. Synthetic chemistry techniques, such as a solid-phase Merrifield-type synthesis, can be used for reasons of purity, antigenic specificity, freedom from undesired side products, ease of production, and the like. A summary of representative techniques can be found in Stewart & Young, 1969; Merrifield, 1969; Fields & Noble, 1990; and Bodanszky, 1993. Solid phase synthesis techniques can be found in Andersson et al., 2000, references cited therein, and in U.S. Pat. Nos. 6,015,561; 6,015,881; 6,031,071; and 4,244,946. Peptide synthesis in solution is described by Schröder & Lübke, 1965. Appropriate protective groups usable in such synthesis are described in the above texts and in McOmie, 1973. Peptides that include naturally occurring amino acids can also be produced using recombinant DNA technology. In addition, peptides comprising a specified amino acid sequence can be purchased from commercial sources (e.g., Biopeptide Co., LLC of San Diego, Calif., United States of America and PeptidoGenics of Livermore, Calif., United States of America).

The term "peptide mimetic" as used herein refers to a ligand that mimics the biological activity of a reference peptide, by substantially duplicating the targeting activity of the reference peptide, but it is not a peptide or peptoid. In one embodiment, a peptide mimetic has a molecular weight of less than about 700 daltons.

A peptide mimetic can be designed by: (a) identifying the pharmacophoric groups responsible for the targeting activity of a peptide; (b) determining the spatial arrangements of the pharmacophoric groups in the active conformation of the peptide; and (c) selecting a pharmaceutically acceptable template upon which to mount the pharmacophoric groups in a manner that allows them to retain their spatial arrangement in the active conformation of the peptide. For identification of pharmacophoric groups responsible for targeting activity, mutant variants of the peptide can be prepared and assayed for targeting activity. Alternatively or in addition, the three-dimensional structure of a complex of the peptide and its target molecule can be examined for evidence of interactions, for example the fit of a peptide side chain into a cleft of the target molecule, potential sites for hydrogen bonding, etc. The spatial arrangements of the pharmacophoric groups can be determined by NMR spectroscopy or X-ray diffraction studies. An initial three-dimensional model can be refined by energy minimization and molecular dynamics simulation. A template for modeling can be selected by reference to a template database and will typically allow the mounting of 2-8 pharmacophores. A peptide mimetic is identified wherein addition of the pharmacophoric groups to the template maintains their spatial arrangement as in the peptide.

A peptide mimetic can also be identified by assigning a hashed bitmap structural fingerprint to the peptide based on its chemical structure, and determining the similarity of that fingerprint to that of each compound in a broad chemical database. The fingerprints can be determined using fingerprinting software commercially distributed for that purpose by Daylight Chemical Information Systems, Inc. (Mission Viejo, Calif.) according to the vendor's instructions. Representative databases include but are not limited to SPREI'95 (InfoChem GmbH of München, Germany), Index Chemicus (ISI of Philadelphia, Pa., United States of America), World Drug Index (Derwent of London, United Kingdom), TSCA93 (United States Envrionmental Protection Agency), MedChem (Biobyte of Claremont, Calif., United States of America), Maybridge Organic Chemical Catalog (Maybridge of Cornwall, England), Available Chemicals Directory (MDL Information Systems of San Leandro, Calif., United States of America), NCI96 (United States National Cancer Institute), Asinex Catalog of Organic Compounds (Asinex Ltd. of Moscow, Russia), and NP (InterBioScreen Ltd. of Moscow, Russia). A peptide mimetic of a reference peptide is selected as comprising a fingerprint with a similarity (Tanamoto coefficient) of at least 0.85 relative to the fingerprint of the reference peptide. Such peptide mimetics can be tested for bonding to an irradiated tumor using the methods disclosed herein.

Additional techniques for the design and preparation of peptide mimetics can be found in U.S. Pat. Nos. 5,811,392; 5,811,512; 5,578,629; 5,817,879; 5,817,757; and 5,811,515.

Any peptide or peptide mimetic of the presently disclosed subject matter can be used in the form of a pharmaceutically acceptable salt. Suitable acids which are capable of the peptides with the peptides of the presently disclosed subject matter include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the presently disclosed subject matter include inorganic bases such as sodium hydroxide, ammonium hydroxide, potassium hydroxide and the like; and organic bases such as mono-di- and tri-alkyl and aryl amines (e.g. triethylamine, diisopropyl amine, methyl amine, dimethyl amine and the like), and optionally substituted ethanolamines (e.g. ethanolamine, diethanolamine and the like).

III.E. Antibody Ligands

An targeting antibody or the presently disclosed subject matter can be identified by the in vivo screening methods disclosed herein. In one embodiment, an antibody targeting ligand comprises: (a) a polypeptide comprising an amino acid sequence of SEQ ID NO: 18, 20, 22, or 24; (b) a polypeptide substantially identical to SEQ ID NO: 18, 20, 22, or 24; (c) a polypeptide encoded by SEQ ID NO: 17, 19, 21, or 23; or (d) a polypeptide encoded by a polynucleotide substantially identical to SEQ ID NO: 17, 19, 21, or 23. Thus, the presently disclosed subject matter also provides an isolated nucleic acid that encodes an antibody targeting ligand comprising: (a) a nucleic acid molecule comprising the nucleotide sequence of SEQ ID NO: 17, 19, 21, or 23; or (b) a nucleic acid molecule substantially identical to SEQ ID NO: 17, 19, 21, or 23.

When phage-displayed antibodies bind to an antigen, they can be affinity-purified using the antigen. These affinity-purified phage can then be used to infect and introduce the antibody gene back into *E. coli*. The *E. coli* can then be grown and induced to express a soluble, non-phage-displayed, antigen-specific recombinant antibody. Phage display technology is especially useful for producing antibodies to antigens that are either poorly immunogenic or readily degraded and for which monoclonal and/or polyclonal antibodies are difficult to obtain. P-selectin, like $\alpha_{2b}\beta_3$, is a high priority radiation-inducible neoantigen because it is not accessible to antibodies or immunoconjugates until after irradiation of tumor vasculature. Phage scFv antibodies have been developed to these proteins by use of phage-displayed antibody library containing $2\times10^9$ members. Negative selection of phage can be first performed on a control tissue, for example untreated vascular endothelium. This can eliminate antibodies that nonspecifically bind to, for example, unirradiated endothelial cells. Unbound phage can then be recovered and incubated with purified radiation-inducible neoantigen, for example, P-selectin or $\alpha_{2b}\beta_3$ integrin. High affinity phage can then be recovered, for example by use of washing at pH 1.

The term "isolated", as used in the context of a nucleic acid or polypeptide, indicates that the nucleic acid or polypeptide exists apart from its native environment and is not a product of nature. An isolated nucleic acid or polypeptide can exist in a purified form or can exist in a non-native environment such as a transgenic host cell. In one embodiment of the presently disclosed subject matter, "isolated" refers to the purification of an scFv antibody from a target tissue to which it has bound.

Nucleic Acids Encoding Targeting Antibodies. The terms "nucleic acid molecule" or "nucleic acid" each refer to deoxyribonucleotides or ribonucleotides and polymers thereof in single-stranded or double-stranded. Unless specifically limited, the term encompasses nucleic acids containing known analogues of natural nucleotides that have similar properties as the reference natural nucleic acid. The terms "nucleic acid molecule" or "nucleic acid" can also be used in place of "gene", "cDNA", or "mRNA". Nucleic acids can be synthesized, or can be derived from any biological source, including any organism.

The term "substantially identical", as used herein to describe a degree of similarity between nucleotide sequences, refers to two or more sequences that have in one embodiment at least about least 60%, in another embodiment at least about 70%, in another embodiment at least about 80%, in another embodiment about 90% to about 99%, in another embodiment about 95% to about 99%, and in still another embodiment about 99% nucleotide identity, as measured using one of the following sequence comparison algorithms (described herein below) or by visual inspection. The substantial identity exists in one embodiment in nucleotide sequences of at least about 100 residues, in another embodiment in nucleotide sequences of at least about 150 residues, and in still another embodiment in nucleotide sequences comprising a full length coding sequence.

Thus, substantially identical sequences can comprise mutagenized sequences, including sequences comprising silent mutations, or variably synthesized sequences. A mutation or variant sequence can comprise a single base change.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

An exemplary nucleotide sequence employed for hybridization studies or assays includes probe sequences that are complementary to or mimic at least an about 14 to 40 nucleotide sequence of a nucleic acid molecule of the presently disclosed subject matter. For this purpose, a probe comprises a region of the nucleic acid molecule other than a sequence encoding a common immunoglobulin region. Thus, a probe can comprise a sequence encoding a domain of the antibody that comprises an antigen-binding site. In one embodiment, probes comprise 14 to 20 nucleotides, or even longer where desired, such as 30, 40, 50, 60, 100, 200, 300 nucleotides or up to the full length of a region of SEQ ID NO: 17, 19, 21, or 23 that encodes an antigen binding site. Such fragments can be readily prepared by, for example, chemical synthesis of the fragment, by application of nucleic acid amplification technology, or by introducing selected sequences into recombinant vectors for recombinant production.

The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen, 1993. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook & Russell, 2001 for a description of SSC buffer. Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4× to 6×SSC at 40° C. For short probes (e.g., about 10 to 50 nucleotides), stringent conditions typically involve salt concentrations of less than about 1M $Na^+$ ion, typically about 0.01 to 1M $Na^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to identify nucleotide sequences that are substantially identical to reference nucleotide sequences of the presently disclosed subject matter. In one embodiment, a probe nucleotide sequence hybridizes to a target nucleotide sequence in 7% sodium dodecyl sulfate (SDS), 0.5M NaPO$_4$, 1 mM ethylenediamine tetraacetic acid (EDTA) at 50° C. followed by washing in 2×SSC, 0.1% SDS at 50° C. In one embodiment, a probe and target sequence hybridize in 7% sodium dodecyl sulfate (SDS), 0.5M NaPO$_4$, 1 mM EDTA at 50° C. followed by washing in 1×SSC, 0.1% SDS at 50° C. In another embodiment, a probe and target sequence hybridize in 7% sodium dodecyl sulfate (SDS), 0.5M NaPO$_4$, 1 mM EDTA at 50° C. followed by washing in 0.5×SSC, 0.1% SDS at 50° C. In another embodiment, a probe and target sequence hybridize in 7% sodium dodecyl sulfate (SDS), 0.5M NaPO$_4$, 1 mM EDTA at 50° C. followed by washing in 0.1×SSC, 0.1% SDS at 50° C. In yet another embodiment, a probe and target sequence hybridize in 7% sodium dodecyl sulfate (SDS), 0.5M NaPO$_4$, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three-dimensional structure, or are biologically functional equivalents. These terms are defined further herein below. Nucleic acid molecules that do not hybridize to each other under stringent conditions are still substantially identical if the corresponding proteins are substantially identical. This can occur, for example, when two nucleotide sequences are significantly degenerate as permitted by the genetic code.

The term "conservatively substituted variants" refers to nucleic acid sequences having degenerate codon substitutions wherein the third position of one or more selected (or all) codons is substituted with mixed-base and/or deoxyinosine residues. See Batzer et al., 1991; Ohtsuka et al., 1985; Rossolini et al., 1994.

The term "subsequence" refers to a sequence of nucleic acids that comprises a part of a longer nucleic acid sequence. An exemplary subsequence is a probe, described herein above, or a primer. The term "primer" as used herein refers to a contiguous sequence comprising in one embodiment about 8 or more deoxyribonucleotides or ribonucleotides, in another embodiment about 10-20 nucleotides, and in still another embodiment about 20-30 nucleotides of a selected nucleic acid molecule. The primers of the presently disclosed subject matter encompass oligonucleotides of sufficient length and appropriate sequence so as to provide initiation of polymerization on a nucleic acid molecule of the presently disclosed subject matter.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

Nucleic acids of the presently disclosed subject matter can be cloned, synthesized, recombinantly altered, mutagenized, or combinations thereof. Standard recombinant DNA and molecular cloning techniques used to isolate nucleic acids are known in the art. Site-specific mutagenesis to create base pair changes, deletions, or small insertions are also known in the art. See e.g., Sambrook & Russell, 2001; Silhavy et al., 1984; Glover & Hames, 1995; Ausubel, 1995.

Single Chain Antibody Polypeptides. As used herein, the phrase "substantially identical" refers to a nucleic acid sequence having in one embodiment at least about 45%, in another embodiment at least about 50%, in another embodiment at least about 60%, in another embodiment at least about 70%, in another embodiment at least about 80%, in another embodiment at least about 90%, in another embodiment at least about 95%, and in still another embodiment at least about 99% sequence identity, when compared over the full length of one of SEQ ID NO: 17, 19, 21, and 23. Methods for determining percent identity are defined herein below.

Substantially identical polypeptides also encompass two or more polypeptides sharing a conserved three-dimensional structure. Computational methods can be used to compare structural representations, and structural models can be generated and easily tuned to identify similarities around important active sites or ligand binding sites. See Saqi et al., 1999; Barton, 1998; Henikoff et al., 2000; Huang et al., 2000.

Substantially identical proteins also include proteins comprising an amino acid sequence comprising amino acids that are functionally equivalent to amino acids of SEQ ID NOs: 18, 20, 22, or 24. The term "functionally equivalent" in the context of amino acid sequences is known in the art and is based on the relative similarity of the amino acid side-chain substituents. See Henikoff & Henikoff, 2000. Relevant factors for consideration include side-chain hydrophobicity, hydrophilicity, charge, and size. For example, arginine, lysine, and histidine are all positively charged residues; that alanine, glycine, and serine are all of similar size; and that phenylalanine, tryptophan, and tyrosine all have a generally similar shape. By this analysis, described further herein below, arginine, lysine, and histidine; alanine, glycine, and serine; and phenylalanine, tryptophan, and tyrosine; are defined herein as biologically functional equivalents.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982). It is known that certain amino acids can be substituted for other amino acids having a similar hydropathic index or score and still retain a similar biological activity. In one embodiment, amino acids for which the hydropathic indices are within ±2 of the original value are substituted for each other. In another embodiment, amino acids for which the hydropathic indices are within ±1 of the original value are substituted for each other. And in still another embodiment, amino acids for which the hydropathic indices are within ±0.5 of the original value are substituted for each other in making changes based upon similar hydropathicity values.

It is also understood in the art that the substitution of like amino acids can be made effectively on the basis of hydrophilicity. U.S. Pat. No. 4,554,101 describes that the greatest local average hydrophilicity of a protein, as governed by the hydrophilicity of its adjacent amino acids, correlates with its immunogenicity and antigenicity, e.g., with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In one embodiment, amino acids for which the hydrophilic indices are within ±2 of the original value are substituted for each other. In another embodiment, amino acids for which the hydrophilic indices are within ±1 of the original value are substituted for each other. And in still another embodiment, amino acids for which the hydrophilic indices are within ±0.5 of the original value are substituted for each other in making changes based upon similar hydropathicity values.

The term "substantially identical" also encompasses polypeptides that are biologically functional equivalents. The term "functional", as used herein to describe polypeptides comprising antibody targeting ligands, refers to two or more antibodies that are immunoreactive with a same radiation-inducible target molecule. In one embodiment, the two or more antibodies specifically bind a same target molecule and substantially lack binding to a control antigen.

The term "specifically binds", when used to describe binding of an antibody to a target molecule, refers to binding to a target molecule in a heterogeneous mixture of other polypeptides.

The phases "substantially lack binding" or "substantially no binding", as used herein to describe binding of an antibody to a control polypeptide or sample, refers to a level of binding that encompasses non-specific or background binding, but does not include specific binding.

Techniques for detecting antibody-target molecule complexes are known in the art and include but are not limited to centrifugation, affinity chromatography and other immunochemical methods. In one embodiment, an antibody-target molecule complex can be detected following administration of an antibody to a subject as described in Examples 6 and 7. In another embodiment, an antibody-target molecule complex can be detected in vivo by performing radiation-guided drug delivery, wherein the drug comprises a targeting antibody of SEQ ID NO: 18, 20, 22, or 24 and a detectable label, as described in Examples 1 and 2. See also Manson, 1992; Law, 1996.

The presently disclosed subject matter also provides functional fragments of a antibody targeting polypeptide. Such functional portion need not comprise all or substantially all of the amino acid sequence of SEQ ID NO: 18, 20, 22, or 24.

The presently disclosed subject matter also includes functional polypeptide sequences that are longer sequences than that of SEQ ID NO: 18, 20, 22, or 24. For example, one or more amino acids can be added to the N-terminus or C-terminus of a antibody targeting ligand. Methods of preparing such proteins are known in the art.

Isolated polypeptides and recombinantly produced polypeptides can be purified and characterized using a variety of standard techniques that are known to the skilled artisan. See e.g., Schröder & Lübke, 1965; Schneider & Eberle, 1993; Bodanszky, 1993; Ausubel, 1995.

Nucleotide and Amino Acid Sequence Comparisons. The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical" in regards to a nucleotide or polypeptide sequence means that a particular sequence varies from the sequence of a naturally occurring sequence by one or more deletions, substitutions, or additions, the net effect of which is to retain biological activity of a gene, gene product, or sequence of interest.

For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, e.g., by the local homology algorithm disclosed in Smith & Waterman, 1981, by the homology alignment algorithm disclosed in Needleman & Wunsch, 1970, by the search for similarity method disclose din Pearson & Lipman, 1988, by computerized implementations of these algorithms (GAP, BESTFIT, FASTA, and TFASTA in the GCG® WISCONSIN PACKAGE™, available from Accelrys Inc., San Diego, Calif., United States of America), or by visual inspection. See generally, Ausubel, 1995.

A representative algorithm for determining percent sequence identity and sequence similarity is the BLAST algorithm, which is described in Altschul et al., 1990. Software for performing BLAST analyses is publicly available through the National Center for Biotechnology Information on the World Wide Web at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W)=11, an expectation (E)=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences. See e.g., Karlin & Altschul, 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1 in one embodiment, less than about 0.01 in another embodiment, and less than about 0.001 in still another embodiment.

III.F. Immunoconjugates

The presently disclosed subject matter also provides immunoconjugate compositions comprising the antibodies and antibody fragments disclosed herein. In one embodiment, the antibody fragment is a humanized scFv antibody. In another embodiment, the antibody fragment is an scFv antibody comprising an amino acid sequence set forth in one of SEQ ID NOs: 18, 20, 22, or 24, or encoded by a nucleic acid comprising SEQ ID NOs: 17, 19, 21, or 23.

Immunoconjugates compositions of the presently disclosed subject matter can be monovalent (i.e. they comprise an antibody that binds to only one epitope present on a radiation-inducible neoantigen) or polyvalent. As used herein, a "polyvalent immunoconjugate composition" refers to an immunoconjugate composition that comprises at least two different ligands (for example, scFv antibodies that bind to radiation-inducible neoantigens) that bind to at least two different targets, at least one of which is a radiation-inducible neoantigen. Thus, in one embodiment a polyvalent immunoconjugate composition comprises a plurality of single chain fragment variable (scFv) antibodies, human Fab antibodies, or combinations thereof, wherein the plurality of antibodies or antibody fragments bind to a plurality of different epitopes, and wherein at least one of the epitopes is present on a radiation-inducible neoantigen. In one embodiment, at least one of the plurality of different epitopes is present on a vascular endothelial cell.

An exemplary polyvalent immunoconjugate is depicted in FIG. 1. As shown in FIG. 1, Antibody 1 binds to an epitope present on endothelium (for example, tumor endothelium), and Antibody 2 binds to an antigen present on vascular endothelium. One or both of the epitopes to which Antibody 1 and Antibody 2 bind can be radiation-inducible neoantigens. This Figure depicts the epitopes to which Antibodies 1 and 2 bind as being different, thus the immunoconjugate is a polyvalent immunoconjugate. However, if Antibody 1 and Antibody 2 bind to the same epitope present on a radiation-inducible neoantigen, the immunoconjugate would be monovalent.

In accordance with the presently disclosed subject matter, immunoconjugate compositions can be used to deliver therapeutic agents to target tissues. Such therapeutic agents include, but are not limited to viruses, radionuclides, cytotoxins, therapeutic genes, and chemotherapeutic agents.

Also in accordance with the presently disclosed subject matter, an immunoconjugate composition, the immunoconjugate composition can further comprise a detectable label. In one embodiment, the detectable label is detectable in vivo. In this embodiment, the detectable label comprises a label that can be detected using magnetic resonance imaging, scintigraphic imaging, ultrasound, or fluorescence. An exemplary detectable label that can be used for detection in vivo is a radionuclide label, for example $^{131}$I or $^{99m}$Tc.

In one embodiment, prioritization and quantification combinations of antibodies employ fluorescent "bar codes". Fluorescent core/shell semiconductor nanocrystals, or "quantum dots", are a new tool for fluorescent imaging in biology (Bruchez et al., 1998; Chan & Nie, 1998). The emission wavelength is precisely tuned by the size of the nanocrystal, which typically range in diameter from 1 nm to 10 nm (corresponding to blue through red emission wavelengths for a CdSe/ZnS core/shell). This small size and appropriate organic surface modification make the nanocrystals readily biocompatible (Dubertret et al., 2002). Unlike organic fluorescent dies, the nanocrystals have narrow, gaussian emission spectra, enabling the visualization of several receptors or cellular components simultaneously. As the absorption spectrum is continuous above the first excitation feature, all sizes, and hence all colors, can be excited with a single excitation source. Finally the nanocrystals photobleach on a timescale of hours, as opposed to minutes.

Ligands (for example, antibodies or antibody fragments that bind to radiation-inducible neoantigens) can be bound to the surface of the nanocrystal in order to image targets to which the ligands bind. For example, a ligand can be conjugated to a mercaptoacetic acid-coated dot via an EDC coupling, and a 5,000 GMW polyethylene glycol chain is used to defeat non-specific binding. Quantum dots can therefore be used to efforts to study the binding of immunoconjugates to targets.

IV. Prioritizing the Binding of scFv Antibodies

The presently disclosed subject matter also provides a method for prioritizing the binding of a plurality of phage-displayed antibodies to a target tissue in a subject, the method comprising: (a) providing a plurality of phage-displayed antibodies that bind to the target, wherein the plurality of phage-displayed antibodies comprise at least two different phage-displayed antibodies that bind a radiation-inducible neoantigen within the target tissue, and wherein the at least two different phage-displayed antibodies are distinguishable from each other; (b) irradiating the target tissue, whereby the radiation-inducible neoantigens are expressed within the target tissue; (c) administering the plurality of phage-displayed antibodies to the subject under conditions sufficient to allow the plurality of phage-displayed antibodies to bind to the radiation-inducible neoantigens in the target tissue; (d) isolating a portion of the target tissue from the subject, wherein the portion comprises the radiation-inducible neoantigens to which the plurality of phage-displayed antibodies bind; (e) identifying the at least two different phage-displayed antibodies in the portion of the target tissue; (f) comparing a relative selectivity and an affinity for the radiation-inducible neoantigens of the at least two different phage-displayed antibodies identified in step (e) in the irradiated target tissue; and (g) assigning a priority to the at least two different phage-displayed antibodies based on the comparing of step (f). In one embodiment, the phage-displayed antibodies are single chain fragment variable (scFv) antibodies. In another embodiment, the phage-displayed antibodies are Fab antibodies.

As used herein, the term "prioritizing" refers to a qualitative and/or quantitative evaluation of the potential usefulness of a given antibody for use in the disclosed methods. For example, as described herein, parameters that can be considered in choosing antibodies (for example, scFv or Fab antibodies) for inclusion in an immunoconjugate include, but are not limited to, the affinity and the specificity of the binding of the antibody to a radiation-inducible neoantigen. In other words, antibodies can be evaluated (i.e. prioritized) based on their affinities and specificities for binding to radiation-inducible neoantigens present in target tissues. The prioritization can include, for example, measuring the fraction of administered antibody that binds to the target tissue versus a control tissue (for example, a non-neoplastic tissue (for example, a normal cell) or non-irradiated vascular endothelium). Thus, an antibody that binds to a radiation-inducible neoantigen in a subject but substantially lacks binding to non-target tissues would be expected to have a higher priority than one that binds to a radiation-inducible neoantigen but also shows substantial binding to normal cells present within a subject. Additional factors that can be used to prioritize antibodies include, but are not limited to prolonged kinetics, specific binding in target tissues, successful targeting after therapeutic doses of radiation, binding to epitopes that are accessible to immunoconjugates, and binding to antigens that remain tethered to tumor vessels.

Several sequential and complementary high throughput screens of antibodies and antibody fragments (for example, scFv antibodies and/or human Fab antibodies) that bind radiation-inducible neoantigens have been developed: (a) phage library screen; (b) fluorometric microvolume assay technology (FMAT; see Stadel et al., 1997 for a discussion of FMAT); (c) BIACORE®/ELISA/westerns; and (d) MALDI-MS. In the first step, antibodies or antibody fragments that bind radiation-inducible neoantigens are selected from a library of phage antibodies (for example, a library of phage-displayed scFv antibodies with a complexity of $10^9$ members). Subsequently, the other screening methodologies are used to prioritize those antibodies that have the highest binding affinities for neoantigens.

Figure 2:
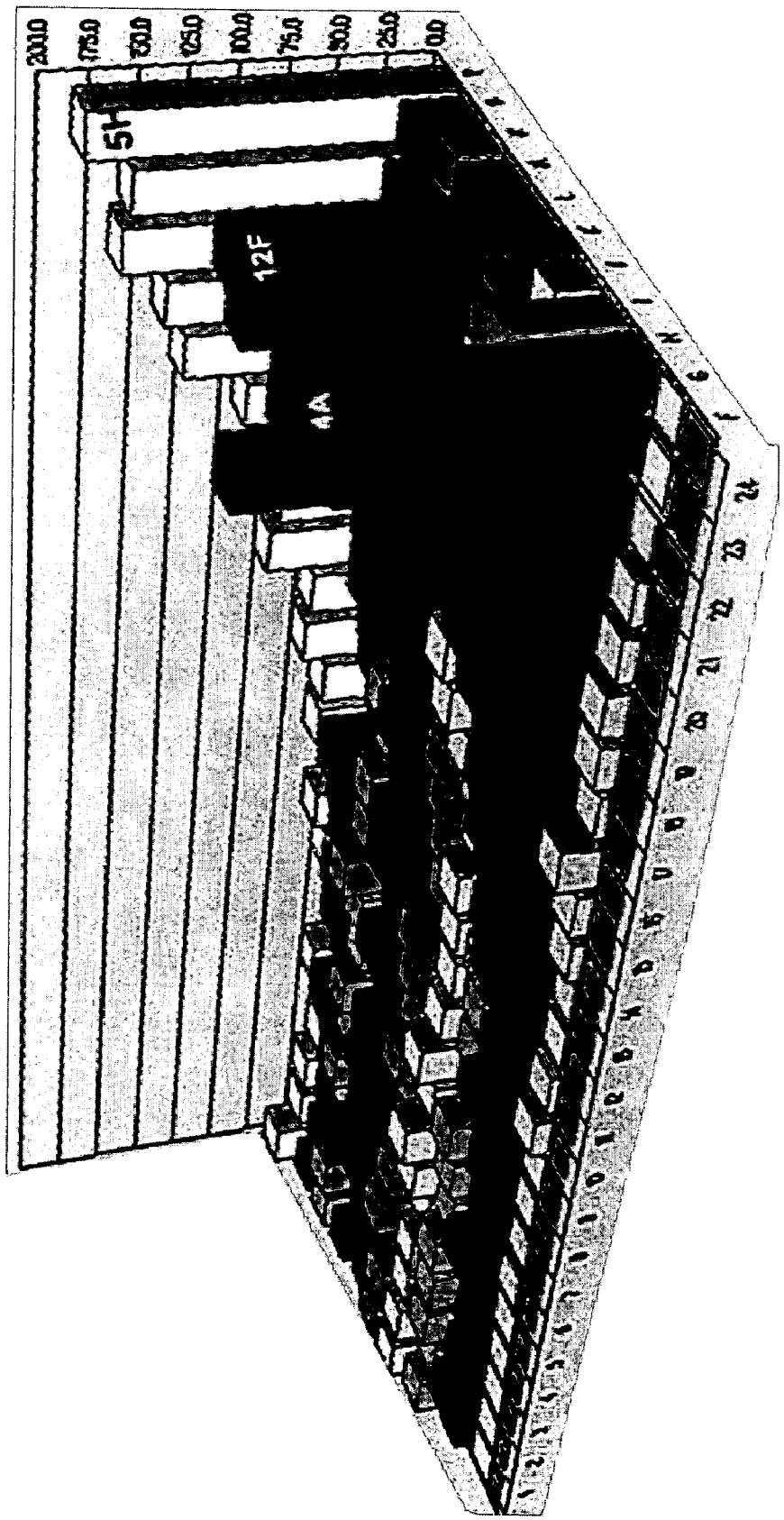
FIG. 2 depicts the output from the FMAT™ 8100 device (PE Biosystems, Foster City, Calif., United States of America) used to prioritize several E-tagged anti-P-selectin single chain fragment variable (scFv) antibodies. In this Figure, Lane F is P-selectin alone. Lane G is P-selectin and secondary (anti-E-tag) antibody. Lanes H-P show the binding of serial dilutions of 9 different anti-P-selectin scFv antibodies.

Fluorometric microvolume assay technology (FMAT) can be used to assay the interactions between ligands (for example, antibodies and antibody fragments) and targets (for example, radiation-inducible neoantigens). An example of the output from the PE Biosystems FMAT™ 8100 used to prioritize several anti-P-selectin scFv antibodies is shown in FIG. 2.

Of those antibodies, several are chosen for simultaneous administration to patients with irradiated tumors (for example, irradiated gliomas), and MALDI-MS is used to detect those antibodies that achieve optimal tumor-specific binding. Imaging mass spectrometry (MS) can be used to develop radiation-inducible antigens and to prioritize antibodies that bind within tumors. This technology brings new and extraordinarily powerful capabilities to the laboratory by allowing imaging of the pattern of a specific molecular weight protein in a tumor sample. MS offers a unique high-accuracy molecular specificity that is invaluable in understanding the molecular events surrounding the interactions of targeting antibodies and their targets (for example, radiation-inducible neoantigens).

MALDI-MS can be used for analyzing large numbers of samples where the molecular weight of peptides and proteins are of prime interest. It utilizes a solid sample mounted on a stage, mixing or coating of the sample with a crystalline organic matrix, and a laser for the deposition of energy into the sample. A time-of-flight analyzer is commonly used to assign mass-to-charge (m/z) ratios to the desorbed ions. The high duty cycle of the laser/analyzer combination permits the acquisition of summed spectra for multiple laser shots and quick downloads so that very high sample throughput is possible. The technology is particularly sensitive for peptide and protein analysis.

Figure 3:
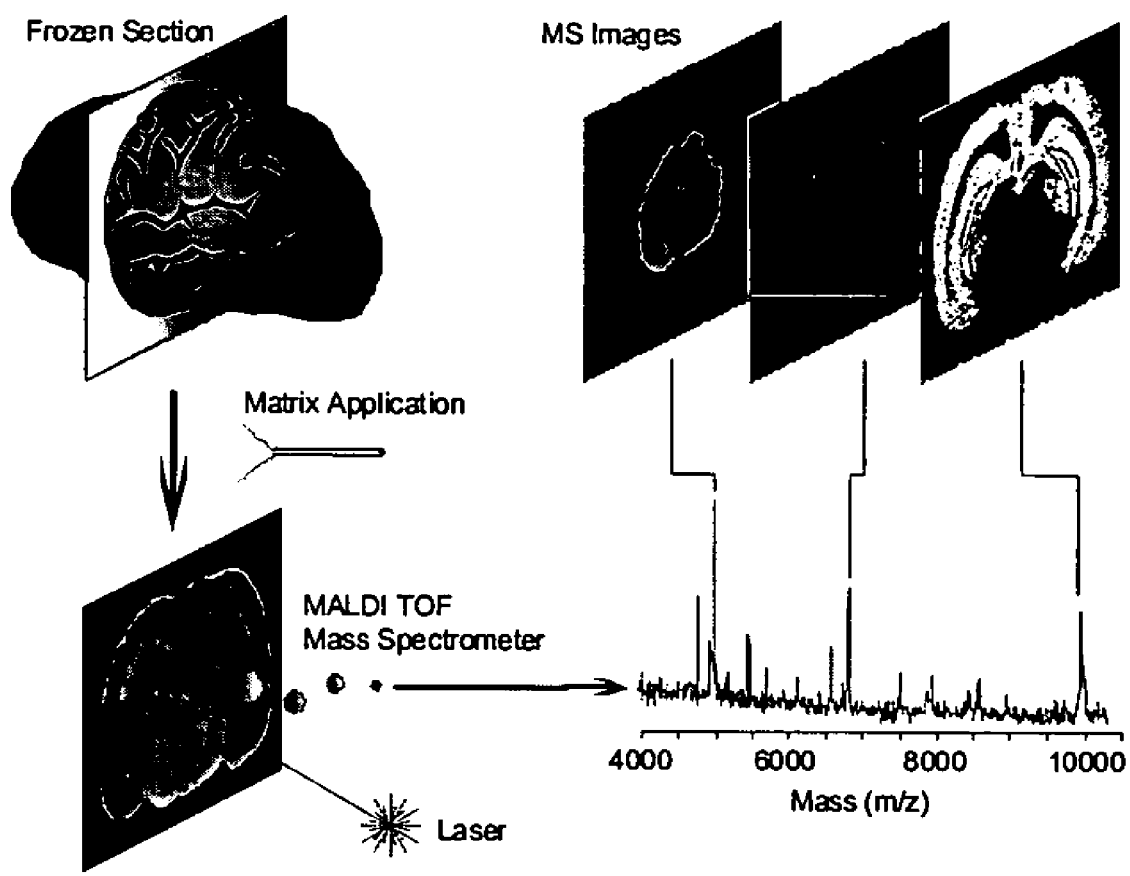
FIG. 3 depicts a general strategy for MALDI-TOF Mass Spectrometry of antibody binding to a target tissue. As depicts in this Figure, a crystalline organic matrix is applied to frozen section of a target tissue that has been treated with a composition of the presently disclosed subject matter (either an antibody or fragment thereof, or an immunoconjugate). The matrix-containing sections are then analyzed by MALDI-TOF, which assigns mass-to-charge (m/z) ratios to the desorbed ions. The mass image profiles can then be used to generate information about the binding of the antibodies or immunoconjugates in the target tissue.

Profiling and imaging techniques using MALDI-MS have been developed for the spatial analysis of peptides and proteins in biological samples, focusing on their applications to tissue sections (Caprioli et al., 1997; Stoeckli et al., 2001). An early use of MALDI-MS for imaging cells and tissues demonstrated that signals for peptides and proteins could be obtained directly from tissues and blots of tissues. Over the past 2 years, the inventors have developed imaging MS technology (FIG. 3) and have shown that relatively large proteins can be desorbed from tissues and blots of tissues in the molecular weight range up to about 80 kDa. Thus, MALDI-MS can be used to prioritize antibody binding in tumors because the molecular weights of scFv antibodies range from about 25 to about 31 kDa. From tumor samples, 300-500 peptide and protein peaks can be recorded in the mass spectrum produced from a single laser ablated area on the sample. Further, a raster of the surface of the sample can be performed with multiple laser spots and the mass spectrum from each spot saved separately, resulting in the production of a data array that contains the relative intensity of any mass at each spot. An image of the sample can then be constructed at any given molecular weight, providing a molecular weight-specific map of the sample. A high-resolution image of a piece of tissue might then consist of an array of 100 by 100 laser spots with each spot being roughly circular with a diameter of 30 µm, covering an area of 3,000 by 3,000 µm. Both the area covered and the density of the laser spots can be covered, depending on the task to be accomplished. Commonly, individual maps can be generated to verify the presence, molecular weight, and location of proteins (for example, scFv antibodies) that have been selected based on preliminary mass spectrometry scans, 2D gels, gene identification and sequencing, and other biochemical information. From a single raster of a piece of tissue, hundreds of image maps can be produced, each at a discrete molecular weight value.

Figure 4A:
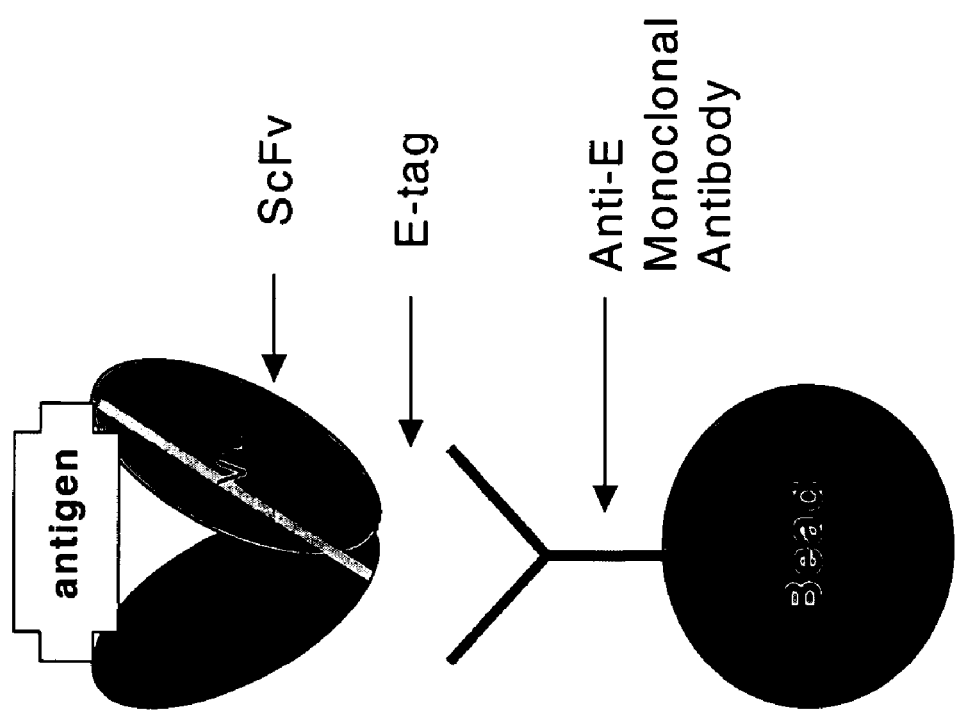
FIGS. 4A and 4B depict mass spectrophotometric analysis of affinity purified scFvs specific for an antigen.
Figure 4B:
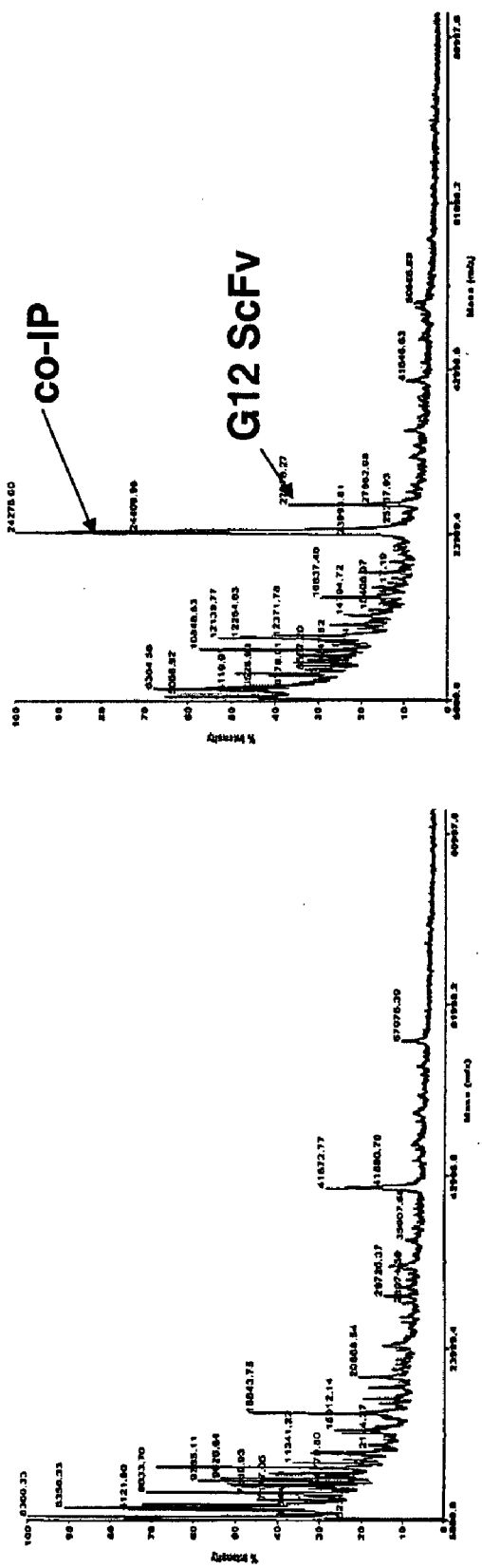

The sequential and complementary high throughput presented herein can be used to examine scFv antibodies that can be differentiated by MALDI-MS in order to perform side-by-side comparisons of antibody binding within tumors. These comparisons can be performed by immunoprecipitating tagged antibodies from tumor homogenates, followed by MALDI-MS. In one embodiment, scFv antibodies are tagged with c-myc and 6xHis, which provide an approach to isolating antibodies from tumor biopsy specimens before they are measured by MALDI-MS. In another embodiment, the scFv antibodies are tagged with an E-tag epitope tag. FIGS. 4A and 4B depict an E-tagged scFv antibody and a mass spectrograph of the affinity purification of such antibodies from a cell lysate, respectively.

V. Tumor Diagnosis, Treatment, and Imaging

The presently disclosed subject matter further provides methods and compositions for x-ray guided drug delivery to a tumor in a subject. The term "drug" as used herein refers to any substance having biological or detectable activity. Thus, the term "drug" includes a pharmaceutical agent, a diagnostic agent, or a combination thereof. The term "drug" also includes any substance that is desirably delivered to a tumor.

Thus, in one embodiment of the presently disclosed subject matter, a composition is prepared, the composition comprising a targeting ligand as disclosed herein and a diagnostic agent. The composition can be used for the detection of a tumor in a subject by: (a) exposing a suspected tumor to ionizing radiation; (b) administering to the subject a targeting ligand of the presently disclosed subject matter, wherein the ligand comprises a detectable label; and (c) detecting the detectable label, whereby a tumor is diagnosed. Alternatively, a method for detecting a tumor can comprise: (a) exposing a suspected tumor to ionizing radiation; (b) biopsing a suspected tumor; (c) contacting a targeting ligand of the presently disclosed subject matter with the suspected tumor in vitro, wherein the ligand comprises a detectable label; and (d) detecting the detectable label, whereby a tumor is diagnosed.

A therapeutic composition of the presently disclosed subject matter can comprise one or more targeting ligands and a therapeutic agent, such that the therapeutic agent can be selectively targeted to an irradiated tumor. The one or more targeting ligands can comprise ligands having diverse molecular features. For example, one or more targeting ligands can comprise both peptide and antibody targeting ligands. In one embodiment, a therapeutic composition is an immunoconjugate. In one embodiment, the immunoconjugate is polyvalent, meaning that it comprises at least two targeting ligands that bind to at least two different epitopes, at least one of which is an epitope found on a radiation-inducible neoantigen.

Optionally, a therapeutic composition can additionally comprise a detectable label, in one embodiment a label that can be detected in vivo. The biodistribution of the therapeutic composition so prepared can be monitored following administration to a subject.

Methods for preparation, labeling, and x-ray guided drug delivery using targeting ligands of the presently disclosed subject matter are described further herein below. See also Examples 1 and 2.

V.A. Therapeutic Agents

The novel targeting ligands disclosed here are used to target a therapeutic agent to an irradiated tumor. Representative therapeutic agents include but are not limited to a nucleic acid (e.g., a therapeutic gene) and a small molecule. In one embodiment of the presently disclosed subject matter, an inactive drug is administered, which is subsequently activated by irradiation (Hallahan et al., 1995b). For example, therapeutic gene expression can be regulated by a radiation-inducible promoter (Hallahan et al., 1995b).

Therapeutic Genes. Angiogenesis and suppressed immune response play a central role in the pathogenesis of malignant disease and tumor growth, invasion, and metastasis. Thus, a representative therapeutic gene encodes a polypeptide having an ability to induce an immune response and/or an anti-angiogenic response in vivo.

The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte proliferation), Representative therapeutic proteins with immunostimulatory effects include but are not limited to cytokines (e.g., an interleukin (IL) such as IL2, IL4, IL7, IL12, interferons, granulocyte-macrophage colony-stimulating factor (GM-CSF), tumor necrosis factor alpha (TNF-$\alpha$)), immunomodulatory cell surface proteins (e.g., human leukocyte antigen (HLA proteins), co-stimulatory molecules, and tumor-associated antigens. See Kirk & Mule, 2000; Mackensen et al., 1997; Walther & Stein, 1999; and references cited therein.

The term "angiogenesis" refers to the process by which new blood vessels are formed. The term "anti-angiogenic response" and "anti-angiogenic activity" as used herein, each refer to a biologic wherein the formation of new blood vessels is inhibited.

Representative proteins with anti-angiogenic activities that can be used in accordance with the presently disclosed subject matter include: thrombospondin I (Kosfeld & Frazier, 1993; Tolsma et al., 1993; Dameron et al., 1994), metallospondin proteins (Carpizo & Iruela-Arispe, 2000), class I interferons (Albini et al., 2000), IL12 (Voest et al., 1995), protamine (Ingber et al., 1990), angiostatin (O'Reilly et al., 1994), Iaminin (Sakamoto et al., 1991), endostatin (O'Reilly et al., 1997), and a prolactin fragment (Clapp et al., 1993). In addition, several anti-angiogenic peptides have been isolated from these proteins (Maione et al., 1990; Eijan et al., 1991; Woltering et al., 1991).

A gene therapy construct used in accordance with the methods of the presently disclosed subject matter can also encode a therapeutic gene that displays both immunostimulatory and anti-angiogenic activities, for example, IL12 (see Dias et al., 1998 and references cited herein below), interferon-$\alpha$ (O'Byrne et al., 2000), and references cited therein), or a chemokine (Nomura & Hasegawa, 2000, and references cited therein). In addition, a gene therapy construct can encode a gene product with immunostimulatory activity and a gene product having anti-angiogenic activity. See e.g. Narvaiza et al., 2000.

Additional compositions useful for cancer therapy include but are not limited to genes encoding tumor suppressor gene products/antigens, antimetabolites, suicide gene products, and combinations thereof. See Kirk & Mule, 2000; Mackensen et al., 1997; Walther & Stein, 1999; and references cited therein.

Therapeutic Compounds. In accordance with the methods of the presently disclosed subject matter, a therapeutic agent can also comprise a cytotoxic agent, a chemotherapeutic agent, a radionuclide, or any other anti-tumor molecule. Studies using ligand/drug conjugates have demonstrated that a chemotherapeutic agent can be linked to a ligand to produce a conjugate that maintains the binding specificity of the ligand and the therapeutic function of the agent. For example, doxorubicin has been linked to antibodies or peptides and the ligand/doxorubicin conjugates display cytotoxic activity (Shih et al., 1994; Lau et al., 1995; Sivam et al., 1995), PCT International Publication No. WO 98/10795). Similarly, other anthracyclines, including idarubicin and daunorubocin, have been chemically conjugated to antibodies, which have facilitated delivery of effective doses of the agents to tumors (Aboud-Pirak et al., 1989; Rowland et al., 1993). Other chemotherapeutic agents include cis-platinum (Schechter et al., 1991), methotrexate (Shawler et al., 1988; Fitzpatrick & Garnett, 1995) and mitomycin-C (Dillman et al., 1989).

In another embodiment of the presently disclosed subject matter, a therapeutic agent comprises a radionuclide. Radionuclides can be effectively conjugated to antibodies (Hartmann et al., 1994; Buchsbaum et al., 1995), small molecule ligands (Wilbur, 1992; Fjalling et al., 1996), and peptides (Boerman et al., 2000; Krenning & de Jong, 2000; Kwekkeboom et al., 2000; Virgolini et al., 2001, and references cited therein), such that administration of the conjugated radionuclide promotes tumor regression. Representative therapeutic radionuclides and methods for preparing a radionuclide-labeled agent are described further herein below under the heading Scintigraphic Imaging. For therapeutic methods of the presently disclosed subject matter, exemplary radionuclides comprise $^{131}$I and $^{99m}$Tc.

Additional anti-tumor agents that can be conjugated to the targeting ligands disclosed herein and used in accordance with the therapeutic methods of the presently disclosed subject matter include but are not limited to alkylating agents such as melphalan and chlorambucil (Smyth et al., 1987; Aboud-Pirak et al., 1989; Rowland et al., 1993), vinca alkaloids such as vindesine and vinblastine (Aboud-Pirak et al., 1989; Starling et al., 1992), antimetabolites such as 5-fluorouracil, 5-fluorouridine and derivatives thereof (Krauer et al., 1992; Henn et al., 1993).

Other Therapeutic Agents. In accordance with the methods of the presently disclosed subject matter, a therapeutic agent can comprise a virus or a viral genome. In one embodiment, a therapeutic agent comprises an oncolytic virus. In an exemplary embodiment, an oncolytic virus comprises a naturally occurring virus that is capable of killing a cell in the target tissue (for example, by lysis) when it enters such a cell. Alternatively, an oncolytic virus can comprise a recombinant viral vector (for example, an adenovirus vector) that has been engineered to encode a polypeptide that, when present in a cell of the target tissue suppresses the growth of that cell or kills it. For example, a recombinant viral vector can comprise an adenovirus vector that has been engineered to encode one of the therapeutic genes disclosed herein, including but not limited to immunostimulatory genes, anti-angiogenic genes, tumor suppressors, antimetabolites, suicide gene products, and combinations thereof.

V.B. Preparation of a Therapeutic and/or Diagnostic Composition

The presently disclosed subject matter also provides a method for preparing a composition for x-ray-guided drug delivery. The method comprises: (a) performing in vivo screening, whereby a ligand that binds a radiation-inducible tumor molecule is identified; and (b) conjugating the ligand to a drug, whereby a composition for x-ray-guided drug delivery is prepared. A drug can further comprise a drug carrier and can be formulated in any manner suitable for administration to a subject. In one embodiment of the presently disclosed subject matter, the method employs a targeting ligand identified by in vivo screening. Such targeting ligands can comprise, for example, peptides (for example, the peptides disclosed in any one of SEQ ID NOs: 1-13), scFv antibodies (for example, the scFv antibodies disclosed in any one of SEQ ID NOs: 18, 20, 22, and 24), and immunoconjugates comprising the peptides and scFv antibodies (such as those disclosed in SEQ ID NOs: 1-13, 18, 20, 22, and 24).

Drug Carriers. The compositions of the presently disclosed subject matter can further comprise a drug carrier to facilitate drug preparation and administration. Any suitable drug delivery vehicle or carrier can be used, including but not limited to a gene therapy vector (e.g., a viral vector or a plasmid), a microcapsule, for example a microsphere or a nanosphere (Manome et al., 1994; Hallahan, 2001a; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997 and U.S. Pat. Nos. 4,551,482, 5,714,166, 5,510,103, 5,490,840, and 5,855,900), and a polysome (U.S. Pat. No. 5,922,545). In one embodiment of the presently disclosed subject matter, a drug carrier comprises a nanosphere, and in another embodiment a drug carrier comprises a liposome.

Conjugation of Targeting Ligands. Antibodies, peptides, or other ligands can be coupled to drugs or drug carriers using methods known in the art, including but not limited to carbodiimide conjugation, esterification, sodium periodate oxidation followed by reductive alkylation, and glutaraldehyde crosslinking. See Goldman et al., 1997; Cheng, 1996; Neri et al., 1997; Nabel, 1997; Park et al., 1997; Pasqualini et al., 1997; Bauminger & Wilchek, 1980; U.S. Pat. No. 6,071,890; and European Patent No. 0 439 095.

In addition, a targeting peptide or antibody can be recombinantly expressed. For example, a nucleotide sequence encoding a targeting peptide or ligand can be cloned into adenovirus DNA encoding the H1 loop fiber, such that the targeting peptide or ligand is extracellularly presented. An adenovirus vector so prepared can be used for x-ray-guided delivery of a gene therapy construct as disclosed herein. A modified adenovirus vector encoding the RGD peptide was observed to transduce the endothelium in tumor blood vessels.

Formulation. A therapeutic composition, a diagnostic composition, or a combination thereof of the presently disclosed subject matter comprises in one embodiment a pharmaceutical composition that includes a pharmaceutically acceptable carrier. Suitable formulations include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exembplary ingredients are SDS, for example in the range of 0.1 to 10 mg/ml, in one embodiment about 2.0 mg/ml; and/or mannitol or another sugar, for example in the range of 10 to 100 mg/ml, in one embodiment about 30 mg/ml; and/or phosphate-buffered saline (PBS). Any other agents conventional in the art having regard to the type of formulation in question can be used.

The therapeutic regimens and pharmaceutical compositions of the presently disclosed subject matter can be used with additional adjuvants or biological response modifiers including, but not limited to, the cytokines interferon (IFN)-α, IFN-γ, IL2, IL4, IL6, tumor necrosis factor (TNF), or other cytokine affecting immune cells.

V.C. Administration

Suitable methods for administration of a therapeutic composition, a diagnostic composition, or combination thereof, of the presently disclosed subject matter include but are not limited to intravascular, subcutaneous, or intratumoral administration. In one embodiment, intravascular administration is employed. For delivery of compositions to pulmonary pathways, compositions can be administered as an aerosol or coarse spray.

For therapeutic applications, a therapeutically effective amount of a composition of the presently disclosed subject matter is administered to a subject. A "therapeutically effective amount" is an amount of the therapeutic composition sufficient to produce a measurable biological tumor response (e.g., an immunostimulatory, an anti-angiogenic response, a cytotoxic response, or tumor regression). Actual dosage levels of active ingredients in a therapeutic composition of the presently disclosed subject matter can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and prior medical history of the subject being treated. In one embodiment, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

For diagnostic applications, a detectable amount of a composition of the presently disclosed subject matter is administered to a subject. A "detectable amount", as used herein to refer to a diagnostic composition, refers to a dose of such a composition that the presence of the composition can be determined in vivo or in vitro. A detectable amount will vary according to a variety of factors, including but not limited to chemical features of the drug being labeled, the detectable label, labeling methods, the method of imaging and parameters related thereto, metabolism of the labeled drug in the subject, the stability of the label (e.g. the half-life of a radionuclide label), the time elapsed following administration of the drug and/or labeled antibody prior to imaging, the route of drug administration, the physical condition and prior medical history of the subject, and the size and longevity of the tumor or suspected tumor. Thus, a detectable amount can vary and can be tailored to a particular application. After study of the present disclosure, and in particular the Examples, it is within the skill of one in the art to determine such a detectable amount.

V.D. Radiation Treatment

The disclosed targeting ligands are useful for x-ray guided drug delivery. Targeted drug delivery to a tumor in a subject can be performed by irradiating the tumor prior to, concurrent with, or subsequent to administration of a composition of the presently disclosed subject matter. In accordance with the in vivo screening methods for discovery of the targeting ligands, the tumor is irradiated in one embodiment 0 hours to about 24 hours before administration of the composition, and in another embodiment about 4 hours to about 24 hours before administration of the composition.

Low doses of radiation can be used for selective targeting using the peptide ligands disclosed herein. In one embodiment, the dose of radiation comprises up to about 2 Gy ionizing radiation. Higher radiation doses can also be used, especially in the case of local radiation treatment as described herein below.

Radiation can be localized to a tumor using conformal irradiation, brachytherapy, or stereotactic irradiation. The threshold dose for inductive changes can thereby be exceeded in the target tissue but avoided in surrounding normal tissues. In this case, a dose of at least about 2 Gy ionizing radiation can be used; in one embodiment, about 10 Gy to about 20 Gy ionizing radiation is used. For treatment of a subject having two or more tumors, local irradiation enables differential drug administration and/or dose at each of the two or more tumors. Alternatively, whole body irradiation can be used, as permitted by the low doses of radiation required for targeting of ligands disclosed herein. Radiotherapy methods suitable for use in the practice of this presently disclosed subject matter can be found in Leibel & Phillips, 1998, among other sources.

V.E. Monitoring Distribution In Vivo

In one embodiment of the presently disclosed subject matter, a diagnostic and/or therapeutic composition for x-ray-guided drug delivery comprises a label that can be detected in vivo. The term "in vivo", as used herein to describe imaging or detection methods, refer to generally non-invasive methods such as scintigraphic methods, magnetic resonance imaging, ultrasound, or fluorescence, each described briefly herein below. The term "non-invasive methods" does not exclude methods employing administration of a contrast agent to facilitate in vivo imaging.

The label can be conjugated or otherwise associated with a targeting ligand (e.g., any one of SEQ ID NOs: 1-13, 18, 20, 22, and 24), a therapeutic, a diagnostic agent, a drug carrier, or combinations thereof. Following administration of the labeled composition to a subject, and after a time sufficient for binding, the biodistribution of the composition can be visualized. The term "time sufficient for binding" refers to a temporal duration that permits binding of the labeled agent to a radiation-inducible target molecule.

Scintigraphic Imaging. Scintigraphic imaging methods include SPECT (Single Photon Emission Computed Tomography), PET (Positron Emission Tomography), gamma camera imaging, and rectilinear scanning. A gamma camera and a rectilinear scanner each represent instruments that detect radioactivity in a single plane. Most SPECT systems are based on the use of one or more gamma cameras that are rotated about the subject of analysis, and thus integrate radioactivity in more than one dimension. PET systems comprise an array of detectors in a ring that also detect radioactivity in multiple dimensions.

A representative method for SPECT imaging is presented in Example 2. Other imaging instruments suitable for practicing the method of the presently disclosed subject matter, and instruction for using the same, are readily available from commercial sources. Both PET and SPECT systems are offered by ADAC (Milpitas, Calif., United States of America) and Siemens (Hoffman Estates, Ill., United States of America). Related devices for scintigraphic imaging can also be used, such as a radio-imaging device that includes a plurality of sensors with collimating structures having a common source focus.

When scintigraphic imaging is employed, the detectable label can comprise a radionuclide label; in alternative embodiements, a radionuclide label selected from the group consisting of $^{18}$fluorine, $^{64}$copper, $^{65}$copper, $^{67}$gallium, $^{68}$gallium, $^{77}$bromine, $^{80m}$bromine, $^{95}$ruthenium, $^{97}$ruthenium, $^{103}$ruthenium, $^{105}$ruthenium, $^{99m}$technetium, $^{107}$mercury, $^{203}$mercury, $^{123}$iodine, $^{124}$iodine, $^{125}$iodine, $^{126}$iodine, $^{131}$iodine, $^{133}$iodine, $^{111}$indium, $^{113}$mindium, $^{99m}$rhenium, $^{105}$rhenium, $^{101}$rhenium, $^{186}$rhenium, $^{188}$rhenium, $^{121}$mtellurium, $^{122m}$tellurium, $^{125m}$tellurium, $^{165}$thulium, $^{167}$thulium, $^{168}$thulium, and nitride or oxide forms derived there from. In one embodiment of the presently disclosed subject matter, the radionuclide label comprises $^{131}$iodine or $^{99m}$technetium.

Methods for radionuclide-labeling of a molecule so as to be used in accordance with the disclosed methods are known in the art. For example, a targeting molecule can be derivatized so that a radioisotope can be bound directly to it (Yoo et al., 1997). Alternatively, a linker can be added to enable conjugation. Representative linkers include diethylenetriamine pentaacetate (DTPA)-isothiocyanate, succinimidyl 6-hydrazinium nicotinate hydrochloride (SHNH), and hexamethylpropylene amine oxime (HMPAO) (Chattopadhyay et al., 2001; Sagiuchi et al., 2001; Dewanjee et al., 1994; U.S. Pat. No. 6,024,938). Additional methods can be found in U.S. Pat. No. 6,080,384; Hnatowich et al., 1996; and Tavitian et al., 1998.

When the labeling moiety is a radionuclide, stabilizers to prevent or minimize radiolytic damage, such as ascorbic acid, gentisic acid, or other appropriate antioxidants, can be added to the composition comprising the labeled targeting molecule.

Magnetic Resonance Imaging (MRI). Magnetic resonance image-based techniques create images based on the relative relaxation rates of water protons in unique chemical environments. As used herein, the term "magnetic resonance imaging" refers to magnetic source techniques including convention magnetic resonance imaging, magnetization transfer imaging (MTI), proton magnetic resonance spectroscopy (MRS), diffusion-weighted imaging (DWI) and functional MR imaging (fMRI). See Rovaris et al., 2001; Pomper & Port, 2000; and references cited therein.

Contrast agents for magnetic source imaging include but are not limited to paramagnetic or superparamagnetic ions, iron oxide particles (Weissleder et al., 1992; Shen et al., 1993), and water-soluble contrast agents. Paramagnetic and superparamagnetic ions can be selected from the group of metals including iron, copper, manganese, chromium, erbium, europium, dysprosium, holmium and gadolinium. Non-limiting examples of metals are iron, manganese and gadolinium. In one embodiment, a metal is gadolinium.

Those skilled in the art of diagnostic labeling recognize that metal ions can be bound by chelating moieties, which in turn can be conjugated to a therapeutic agent in accordance with the methods of the presently disclosed subject matter. For example, gadolinium ions are chelated by diethylenetriamine pentaacetic acid (DTPA). Lanthanide ions are chelated by tetaazacyclododocane compounds. See U.S. Pat. Nos. 5,738,837 and 5,707,605. Alternatively, a contrast agent can be carried in a liposome (Schwendener, 1992).

Images derived used a magnetic source can be acquired using, for example, a superconducting quantum interference device magnetometer (SQUID, available with instruction from Quantum Design of San Diego, Calif.). See U.S. Pat. No. 5,738,837.

Ultrasound. Ultrasound imaging can be used to obtain quantitative and structural information of a target tissue, including a tumor. Administration of a contrast agent, such as gas microbubbles, can enhance visualization of the target tissue during an ultrasound examination. In one embodiment, the contrast agent can be selectively targeted to the target tissue of interest, for example by using a peptide for x-ray guided drug delivery as disclosed herein. Representative agents for providing microbubbles in vivo include but are not limited to gas-filled lipophilic or lipid-based bubbles (e.g., U.S. Pat. Nos. 6,245,318, 6,231,834, 6,221,018, and 5,088,499). In addition, gas or liquid can be entrapped in porous inorganic particles that facilitate microbubble release upon delivery to a subject (U.S. Pat. Nos. 6,254,852 and 5,147,631).

Gases, liquids, and combinations thereof suitable for use with the presently disclosed subject matter include air; nitrogen; oxygen; is carbon dioxide; hydrogen; nitrous oxide; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. Halogenated hydrocarbon gases can show extended longevity, and thus can be used for some applications. Representative gases of this group include decafluorobutane, octafluorocyclobutane, decafluoroisobutane, octafluoropropane, octafluorocyclopropane, dodecafluoropentane, decafluorocyclopentane, decafluoroisopentane, perfluoropexane, perfluorocyclohexane, perfluoroisohexane, sulfur hexafluoride, and perfluorooctaines, perfluorononanes; perfluorodecanes, optionally brominated.

Attachment of targeting ligands to lipophilic bubbles can be accomplished via chemical crosslinking agents in accordance with standard protein-polymer or protein-lipid attachment methods (e.g., via 1-Ethyl-3-(3-dimethylaminopropyl)-carbodiimide (EDC) or N-succinimidyl 3-(2-pyridylthio)propionate (SPDP)). To improve targeting efficiency, large gas-filled bubbles can be coupled to a targeting ligand using a flexible spacer arm, such as a branched or linear synthetic polymer (U.S. Pat. No. 6,245,318). A targeting ligand can be attached to the porous inorganic particles by coating, adsorbing, layering, or reacting the outside surface of the particle with the targeting ligand (U.S. Pat. No. 6,254,852).

A description of ultrasound equipment and technical methods for acquiring an ultrasound dataset can be found in Coatney, 2001; Lees, 2001; and references cited therein.

Fluorescent Imaging. Non-invasive imaging methods can also comprise detection of a fluorescent label. A drug comprising a lipophilic component (therapeutic agent, diagnostic agent, vector, or drug carrier) can be labeled with any one of a variety of lipophilic dyes that are suitable for in vivo imaging. See e.g. Fraser, 1996; Ragnarson et al., 1992; and Heredia et al., 1991. Representative labels include, but are not limited to carbocyanine and aminostyryl dyes; in one embodiment long chain dialkyl carbocyanines (e.g., Dil, DiO, and DiD available from Molecular Probes Inc. of Eugene, Oreg., United States of America) and dialkylaminostyryl dyes. Lipophilic fluorescent labels can be incorporated using methods known to one of skill in the art. For example VYBRANT™ cell labeling solutions are effective for labeling of cultured cells of other lipophilic components (Molecular Probes Inc. of Eugene, Oreg., United States of America). Preparation of liposomes comprising a targeting ligand and a Dil detectable label are described in Example 1.

A fluorescent label can also comprise sulfonated cyanine dyes, including Cy5.5 and Cy5 (available from Amersham of Arlington Heights, Ill.), IRD41 and IRD700 (available from Li-Cor, Inc. of Lincoln, Nebr.), NIR-1 (available from Dejindo of Kumamoto, Japan), and LaJolla Blue (available from Diatron of Miami, Fla.). See also Licha et al., 2000; Weissleder et al., 1999; and Vinogradov et al., 1996.

In addition, a fluorescent label can comprise an organic chelate derived from lanthanide ions, for example fluorescent chelates of terbium and europium (U.S. Pat. No. 5,928,627). Such labels can be conjugated or covalently linked to a drug as disclosed therein.

For in vivo detection of a fluorescent label, an image is created using emission and absorbance spectra that are appropriate for the particular label used. The image can be visualized, for example, by diffuse optical spectroscopy.

Additional methods and imaging systems are described in U.S. Pat. Nos. 5,865,754; 6,083,486; and 6,246,901, among other places.

V.F. In Vitro Detection

The presently disclosed subject matter further provides methods for diagnosing a tumor, wherein a tumor sample or biopsy is evaluated in vitro. In this case, a targeting ligand of the presently disclosed subject matter comprises a detectable label such as a fluorescent, epitope, or radioactive label, each described briefly herein below.

Fluorescence. Any detectable fluorescent dye can be used, including but not limited to FITC (fluorescein isothiocyanate), FLUOR X™, ALEXA FLUOR®, OREGON GREEN®, TMR (tetramethylrhodamine), ROX (X-rhodamine), TEXAS RED®, BODIPY® 630/650, and Cy5 (available from Amersham Pharmacia Biotech of Piscataway, N.J. or from Molecular Probes Inc. of Eugene, Oreg.).

A fluorescent label can be detected directly using emission and absorbance spectra that are appropriate for the particular label used. Common research equipment has been developed for in vitro detection of fluorescence, including instruments available from GSI Lumonics (Watertown, Mass., United States of America) and Genetic MicroSystems Inc. (Woburn, Mass., United States of America). Most of the commercial systems use some form of scanning technology with photomultiplier tube detection. Criteria for consideration when analyzing fluorescent samples are summarized by Alexay et al., 1996.

Detection of an Epitope. If an epitope label has been used, a protein or compound that binds the epitope can be used to detect the epitope. A representative epitope label is biotin, which can be detected by binding of an avidin-conjugated fluorophore, for example avidin-FITC, as described in Example 7. Alternatively, the label can be detected by binding of an avidin-horseradish peroxidase (HRP) streptavidin conjugate, followed by calorimetric detection of an HRP enzymatic product. The production of a colorimetric or luminescent product/conjugate is measurable using a spectrophotometer or luminometer, respectively.

Autoradiographic Detection. In the case of a radioactive label (e.g., $^{131}I$ or $^{99m}Tc$) detection can be accomplished by conventional autoradiography or by using a phosphorimager as is known to one of skill in the art. An exemplary autoradiographic method employs photostimulable luminescence imaging plates (Fuji Medical Systems of Stamford, Conn.). Briefly, photostimulable luminescence is the quantity of light emitted from irradiated phosphorous plates following stimulation with a laser during scanning. The luminescent response of the plates is linearly proportional to the activity (Amemiya et al., 1988; Hallahan et al., 2001b).

VI. Identification of a Radiation-Inducible Neoantigens

Targeting ligands obtained using the methods disclosed herein can be used to identify and/or isolate a target molecule that is recognized by the targeting ligand. Representative methods include affinity chromatography, biotin trapping, and two-hybrid analysis, each described briefly herein below.

Affinity Chromatography. A representative method for identification of a radiation-inducible target molecule is affinity chromatography. For example, a targeting ligand as disclosed herein can be linked to a solid support such as a chromatography matrix. A sample derived from an irradiated tumor is prepared according to known methods in the art, and such sample is provided to the column to permit binding of a target molecule. The target molecule, which forms a complex with the targeting ligand, is eluted from the column and collected in a substantially isolated form. The substantially isolated target molecule is then characterized using standard methods in the art. See Deutscher, 1990.

Biotin Trapping. A related method employs a biotin-labeled targeting ligand such that a complex comprising the biotin-labeled targeting ligand bound to a target molecule can be purified based on affinity to avidin, which is provided on a support (e.g., beads, a column). A targeting ligand comprising a biotin label can be prepared by any one of several methods, including binding of biotin maleimide [3-(N-maleimidylpropionyl)biocytin] to cysteine residues of a peptide ligand (Tang & Casey, 1999), binding of biotin to a biotin acceptor domain, for example that described in *K. pneumoniae* oxaloacetate decarboxylase, in the presence of biotin ligase (Julien et al., 2000), attachment of biotin amine to reduced sulfhydryl groups (U.S. Pat. No. 5,168,037), and chemical introduction of a biotin group into a nucleic acid ligand, (Carninci et al., 1996). In one embodiment, a biotin-labeled targeting ligand and the unlabeled same target ligand show substantially similar binding to a target molecule.

Two-Hybrid Analysis. As another example, targeting ligands can be used to identify a target molecule using a two-hybrid assay, for example a yeast two-hybrid or mammalian two-hybrid assay. In one embodiment of the method, a targeting ligand is fused to a DNA binding domain from a transcription factor (this fusion protein is called the "bait"). Representative DNA-binding domains include those derived from GAL4, LEXA, and mutant forms thereof. One or more candidate target molecules are fused to a transactivation domain of a transcription factor (this fusion protein is called the "prey"). Representative transactivation domains include those derived from *E. coli* B42, GAL4 activation domain II, herpes simplex virus VP16, and mutant forms thereof. The fusion proteins can also include a nuclear localization signal.

The transactivation domain should be complementary to the DNA-binding domain, meaning that it should interact with the DNA-binding domain so as to activate transcription of a reporter gene comprising a binding site for the DNA-binding domain. Representative reporter genes enable genetic selection for prototrophy (e.g. LEU2, HIS3, or LYS2 reporters) or by screening with chromogenic substrates (lacZ reporter).

The fusion proteins can be expressed from a same vector or different vectors. The reporter gene can be expressed from a same vector as either fusion protein (or both proteins), or from a different vector. The bait, prey, and reporter genes are co-transfected into an assay cell, for example a microbial cell (e.g., a bacterial or yeast cell), an invertebrate cell (e.g., an insect cell), or a vertebrate cell (e.g., a mammalian cell, including a human cell). Cells that display activity of the encoded reporter are indicative of a binding interaction between the peptide and the candidate target molecule. The protein encoded by such a clone is identified using standard protocols known to one of skill in the art.

Additional methods for yeast two-hybrid analysis can be found in Brent & Finley, 1997; Allen et al., 1995; Lecrenier et al., 1998; Yang et al., 1995; Bendixen et al., 1994; Fuller et al., 1998; Cohen et al., 1998; Kolonin & Finley, 1998; Vasavada et al., 1991; Rehrauer et al., 1996; Fields & Song, 1989.

Mass Spectroscopy. MALDI-MS can be used to identify radiation-inducible neoantigens that are well suited for immunoconjugate-mediated drug delivery. These include antigens that are not expressed in normal vasculature, but are inducible and tethered within tumor blood vessels and stroma. The host components of tumors (vasculature and stroma) respond to ionizing radiation with physiologic responses that occur within most if not all tumors. These include responses to oxidative stress and tissue injury such as receptor and enzyme activation. The response in vasculature of heterotopic tumors implanted into mice is described herein.

Novel radiation-inducible neoantigens can also be identified by analyzing the response of human head and neck squamous cell carcinoma (HNSCC) from biopsies of tumors following irradiation and characterizing the proteomic response to irradiation within both microvasculature and stroma. For example, the response of stroma and endothelium following irradiation of tumors can be analyzed to detect sites of apoptosis using terminal deoxynucleotidyl transferase-mediated nick end labeling (TUNEL) staining. Using this approach, it was observed that irradiated tumor endothelial respond with apoptosis which provides neoantigenic targets for drug delivery.

EXAMPLES

The following Examples have been included to illustrate modes of the presently disclosed subject matter. Certain aspects of the following Examples are described in terms of techniques and procedures found or contemplated by the present co-inventors to work well in the practice of the presently disclosed subject matter. These Examples illustrate standard laboratory practices of the co-inventors. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

X-Ray Guided Delivery of Fibrinogen-Conjugated Liposomes and Microspheres

Preparation of Radiolabeled Microspheres. Albumin microspheres (Martodam et al., 1979) were resuspended using 10 ml of sterile normal saline (0.9% NaCl). One-half milliliter of the reconstituted microsphere was added to a 1.5 ml conical polypropylene tube previously coated with IODO-GEN® (Pierce Biotechnology, Inc., Rockford, Ill., United States of America). To this, 11.3 mCi (418 megabecquerel (MBq)) of $^{131}$I (DuPont Pharmaceuticals, Wilmington, Del., United States of America) was added in approximately 11 µl of saline and allowed to incubate at room temperature for 30 minutes. Following incubation, the microspheres were transferred to a 15 ml sterile centrifuge tube, diluted to 10 ml with normal saline, and centrifuged at 1,500 g for seven minutes. The supernatant was removed and discarded. The microspheres were washed one additional time with 10 ml of normal saline and centrifuged. The microspheres were suspended in 2 ml of normal saline for injection. Final yield was 4.8 mCi (177.6 MBq) of radioiodinated microspheres in 2 ml saline. Radiochemical yield was 42.4%.

Preparation of Fibrinogen-Conjugated Liposomes. The lipophilic SH reactive reagent with a long spacing arm was synthesized from maleimide-PEG 2000-NSH ester (Prochem Chemicals, High Point, N.C., United States of America), dioleoylphosphatidylethanolanime (DOPE, available from AVANTI® Polar Lipids, Inc., Alabaster, Ala., United States of America) and triethylamine in chloroform (1:1:1.5). Resulting maleimide-PEG 2000-DOPE was purified by flash column. Under stirring, to a solution of fibrinogen (2 mg/ml) in 0.01M HEPES 0.15 NaCl buffer pH 7.9, containing 10 mM EDTA and 0.08% NaN$_3$ was added in 5-fold excess of freshly prepared Traut's reagent (2-iminothiolane hydrochloride) in the same buffer. The reaction was allowed to proceed for 30 minutes at 0° C.

SH-fibrinogen was purified using a PD-10 desalting and buffer exchange column (Amersham Pharmacia Biotech, Piscataway, N.J., United States of America). PEG 2000-PE, cholesterol, Dipalmitoyl phosphocholine (AVANTI® Polar Lipids, Inc., Alabaster, Ala., United States of America), DiI (lipid fluorescent marker available from Molecular Probes, Eugene, Oreg., United States of America), and maleimide-PEG-2000-DOPE were dissolved in chloroform and mixed at a molar ratio of 10:43:43:2:2, respectively, in a round bottom flask. The organic solvent was removed by evaporation followed by desiccation under vacuum for 2 hours. Liposomes were prepared by hydrating the dried lipid film in PBS at a lipid concentration of 10 mM. The suspension was then sonicated 3×5 minutes, or until the solution appeared clear, to form unilamellar liposomes of 100 nM in diameter. To conjugate thiolated fibrinogen to maleimide containing liposomes, prepared vesicles and thiolated protein were mixed in 10 mm HEPES, 0.15 M NaCl and EDTA pH 6.5. The final concentrations for proteins and liposomes were 0.25 g/L and 2.5 mM, respectively. The peptide/liposome mixture was incubated for 18 hours at room temperature. Vesicles were then separated from unconjugated peptide using a sepharose 4B-CL filtration column (Amersham Pharmacia Biotech, Piscataway, N.J., United States of America).

Liposomes were fluorescently labeled with DiI fluorescent marker (Molecular Probes, Inc., Eugene, Oreg., United States of America) according to the manufacturer's instructions. Labeled liposomes were administered by tail vein injection to tumor bearing mice. Tumors were treated with 4 Gy either prior to administration or after administration of fibrinogen-liposome conjugates. Tumors were fixed and sectioned at 24 hours following irradiation. Fluorescence was imaged by ultraviolet microscopy (100×).

Image Analysis. Tumors were grown in the hind limb of nude and C57BL/6 mice and irradiated with 4 Gy as described in Hallahan et al., 1995b and Hallahan et al., 1998. Tumors were produced by injection of about $10^6$ GL261 (glioblastoma multiforme), B16F0 (murine melanoma), or Lewis lung carcinoma cells were injected into the hind limb(s) of mice and allowed to grow to a size of about 0.7 to 1.0 cm. $^{131}$I-fibrinogen was then administered by tail vein injection and gamma camera images were obtained. Tumor bearing mice were imaged at one hour and 24 hours post-administration of radiolabeled proteins. Planar pinhole gamma camera imaging was performed on a single-head gamma camera (HELIX® model from General Electric Medical Systems, Milwaukee, Wis., United States of America) using a cone-shaped pinhole collimator with a 4-mm diameter Tungsten aperture. Pinhole collimation offers the advantage of improved photon detection efficiency (sensitivity) and spatial resolution when compared with conventional, parallel multi-hole collimators. Pinhole planar imaging with a small source-aperture separation can provide high-resolution images combined with large magnification. Each scan consisted of a 180-second acquisition (256×256 acquisition matrix) with a 10% energy window centered on 364 keV. The source-aperture separation was 6.0 cm.

Prior to imaging analysis in animals, a uniform $^{131}$I disk source was imaged in order to measure the angular dependence of the pinhole collimator—gamma camera system detection efficiency with distance from the center of the pinhole. Angular sensitivity, normalized to 1.0 at the center of the pinhole, was then used to scale the mouse data in order to correct image counts for this geometrical effect. A calibration source of known $^{131}$I activity was also scanned at a 6.0 cm source-aperture separation distance in order to measure system sensitivity along the center of the pinhole.

Peptide biodistribution data was assessed using two measures: (1) tumor-to-background ratio (T/B) of observed activity; and (2) tumor uptake activity in microcuries (µCi). Both types of data were obtained using region of interest (ROI) analysis. For both measurements an 11×11 ROI was used to determine mean counts within the tumor ($\sigma_T$) and at five different locations within the mouse background ($\sigma_B$). These readings were scaled to account for geometric sensitivity and the ratio of tumor uptake to total animal uptake (R) was computed according to the relation, $$R = \frac{\sigma_T}{(\sigma_T + \sigma_B)}.$$

Activity uptake in the tumor was then approximated by the product of the amount of activity administered into the animal multiplied by the value obtained for R above. Tumor-background ratios were determined according to the general expression:

$$\left(\frac{T}{B}\right) = \frac{\sigma_T}{\sigma_B}.$$

Fibrinogen Coated Microsphere Localize to Irradiated Tumors.

Fibrinogen-coated microspheres were radiolabeled with $^{131}$I and administered by tail vein injection into tumor bearing mice, and tumors were irradiated with 6 Gy. The specificity of fibrinogen-coated albumin was determined by measuring the intensity of gamma detection within regions of interest (ROI) and well counts of tumor and other tissues. In animals receiving localized radiation at the tumor site, 90% of the measured radioactivity was localized to the tumor, and 10% of the radioactivity was diffusely distributed throughout the entire animal model. In untreated controls, 10% of radioactive counts were localized to the tumor (p<0.001).

During optimization studies, tumors were irradiated immediately before or immediately after tail vein injection. Both schedules were effective in achieving $^{131}$I-fibrinogen-coated microsphere binding. However, tumor irradiation subsequent to microsphere administration achieved increased targeting specificity when compared to tumors irradiated prior to microsphere administration. Microspheres lacking the fibrinogen ligand did not bind irradiated tumors.

To quantify a level of binding of fibrinogen-coated microspheres in irradiated tumors, data were normalized based on background levels of radiation. Fibrinogen-coated microspheres were 100-fold more abundant in irradiated tumors compared to non-tumor control tissues. By contrast, microspheres lacking the fibrinogen ligand were detected at similar levels in tumor and non-tumor control tissues.

To determine whether fibrinogen-conjugated microspheres bind irradiated non-tumor control tissues, the entire hind quarters of mice bearing hind limb tumors were irradiated, and radiolabeled fibrinogen-coated microspheres were administered immediately after irradiation. Well counts of all tissues were performed at 24 hours after irradiation. 90% of radioactive counts were detected in the tumor. By contrast, 2% of radioactive counts were detected in irradiated non-tumor control tissue, demonstrating selective targeting of fibrinogen-coated microspheres to irradiated tumors.

Fibrinogen-Liposome Conjugates Localize to Irradiated Tumors.

Fibrinogen-conjugated, fluorescently labeled liposomes were administered by tail vein into mice bearing tumors on both hind limbs. The right tumor was treated with radiation and the left tumor served as the untreated control. Untreated control tumors showed no fibrinogen-liposome conjugate binding whereas tumors irradiated immediately before or immediately after tail vein injection showed fibrinogen adhesion in blood vessels. The fluorescent marker was observed within the vascular lumen of tumor microvasculature.

Studies using radiolabeled fibrinogen-conjugated liposomes gave similar results. When liposomes were administered after tumor irradiation, 89% of fibrinogen-coated liposomes localized to tumors. When liposomes were administered immediately prior to tumor irradiation, 69% of liposomes showed tumor localization. By contrast, in untreated controls, a background level of 9% of fibrinogen-coated liposomes localized to the tumor.

Example 2

Clinical Trials of X-Ray-Guided Delivery Using a Peptide Ligand

Ligand Preparation and Administration

Biapcitide (ACUTECT® available from Diatide, Inc., Londonderry, N.H., United States of America) is a synthetic peptide that binds to GP-IIb/IIIa receptors on activated platelets (Hawiger et al., 1989; Hawiger & Timmons, 1992). Biapcitide was labeled with $^{99m}$Tc in accordance with a protocol provided by Diatide Inc.

Reconstituted $^{99m}$Tc-labeled biapcitide was administered to patients at a dose of 100 mcg of biapcitide radiolabeled with 10 millicuries (mCi) of $^{99m}$Tc. Patients received $^{99m}$Tc-labeled biapcitide intravenously immediately prior to irradiation. Patients were then treated with 10 Gy or more. Patients underwent gamma camera imaging prior to irradiation and 24 hours following irradiation. Following planar image acquisition, those patients showing uptake in irradiated tumors underwent tomographic imaging using SPECT and repeat imaging at 24 hours. Patients showing no uptake on planer images during this 24-hour time frame had no further imaging. Each patient had an internal control, which consisted of a baseline scan immediately following administration of $^{99m}$Tc-labeled biapcitide.

Patients were treated with X-irradiation ranging from 4 to 18 MV photon using external beam linear accelerator at Vanderbilt University. Appropriate blocks, wedges and bolus to deliver adequate dose to the planned target volume was utilized. The site of irradiation, treatment intent and normal tissue considerations determined the radiation dosage and volume. When stereotactic radiosurgery was used, the dose was prescribed to the tumor periphery.

Image Analysis. Image acquisition consisted of both planar and single photon emission computed tomography (SPECT) studies. Planar studies were performed on a dual-head gamma camera (Millenium VG—Variable Geometry model available from General Electric Medical Systems of Milwaukee, Wis.) equipped with low energy high-resolution (LEUR) collimators. This type of collimator represents a compromise between sensitivity (photon counting efficiency) and image resolution. Planar nuclear medicine images were acquired with a 256×256 acquisition matrix (pixel size approximately 0.178 cm/pixel) for 10 minutes. In order to maximize collimator-gamma camera system sensitivity the source-to-detector surface distance was minimized to the extent that patient geometry allows. The spatial distribution of fibrinogen within the planar image was measured using region of interest (ROI) analysis. Two different size ROI's (5×5 pixel, and 15×15 pixel) was used in both the tumor and surrounding organs and tissues in the patient. The rationale for using ROIs with different dimensions is to be able to quantify image counts while at the same time isolating any possible influence of ROI size on the results. Tumor-to-background ratios were computed as the ratio of average counts in the tumor region divided by average counts in surrounding organs and tissues, each corrected for background. Background counts was determined based on ROI analysis of a separate planar acquisition performed in the absence of a radioactive source.

Three-dimensional nuclear medicine SPECT examinations were performed using the same dual-head gamma camera system. Each SPECT study comprised a 360 scan acquired with a step-and-shoot approach utilizing the following acquisition parameters: three increments between views, a 256×256×64 acquisition matrix, LEUR collimation and 60 seconds per view. Images were reconstructed using analytical filtered back-projection and statistical maximum likelihood techniques with photon attenuation correction and post-reconstruction deconvolution filtering for approximate detector response compensation. In this case, correction for background consisted of subtracting counts acquired in a single 60-second planar view from all views of the SPECT projection data prior to image reconstruction. SPECT tumor-to-background ratios were computed using quantitative ROI techniques identical to the planar studies.

Results. Administration of a $^{99m}$Tc-labeled biapticide, an RGD peptide mimetic, immediately prior to radiation resulted in tumor binding in 4 of 4 patients (Hallahan et al., 2001a). Two patients among this group had second neoplasms that were not treated with radiation, and binding of $^{99m}$Tc-labeled biapticide was not observed in the untreated tumor. Administration of the $^{99m}$Tc-labeled biapticide within one hour following radiation also failed to show localization of the targeting molecule to the tumor (Hallahan et al., 2001a).

Example 3

Response of Tumor Blood Vessels to Ionizing Radiation

To determine the response of tumor blood vessels to ionizing radiation, a tumor vascular window and Doppler sonography were used to measure the change in tumor blood vessels (Donnelly et al., 2001; Geng et al., 2001). Tumors implanted into the window model developed blood vessels within 1 week. Tumors were then treated with radiation and the response of blood vessels was imaged by use of light microscopy. Radiation doses in the range of 2-3 Gy increased the vascularity within tumors. In contrast, larger doses of radiation such as 6 Gy reduced tumor vascularity.

Established tumors were studied to determine whether there is a dose-dependent change in blood flow following irradiation. Tumors in the hind limb were grown to approximately 1 cm in diameter. Blood flow within tumors was measured by use of power Doppler (Donnelly et al., 2001). Tumors were treated with 3 Gy or 6 Gy ionizing radiation, and changes in tumor blood flow were measured using power Doppler sonography. A radiation dose of 3 Gy achieved an increase in tumor blood flow. In contrast, radiation doses of 6 Gy or higher markedly reduced tumor blood flow.

Example 4

Preparation of a Recombinant Peptide Library in Phage

A population of DNA fragments encoding recombinant peptide sequences was cloned into the T7 SELECT™ vector (Novagen, Madison, Wis., United States of America). Cloning at the EcoR I restriction enzyme recognition site places the recombinant peptide in-frame with the 10B protein such that the peptide is displayed on the capsid protein. The resulting reading frame requires an AAT initial codon followed by a TCX codon.

The molar ratio between insert and vector was 1:1. Size-fractionated cDNA inserts were prepared by gel filtration on sepharose 4B and ranged from 27 base pairs to 33 base pairs. cDNAs were ligated by use of the DNA ligation kit (Novagen, Madison, Wis., United States of America). Recombinant T7 DNA was packaged according to the manufacturer's instructions and amplified prior to bioscreening in animal tumor models. The diversity of the library was $10^7$.

Example 5

In Vivo Screening for Peptide Ligands to Radiation-Inducible Molecules

GL261 murine glioma cells and Lewis lung carcinoma cells were implanted into the hind limb of C57BL6 mice (Hallahan et al., 1995b; Hallahan et al., 1998; Hallahan & Virudachalam, 1999).

To determine the optimal time at which peptides bind within tumors, phage were administered at 1 hour before, at 1 hour after, and at 4 hours after irradiation of both LLC and GL261 tumors. Phage were recovered from tumors when administered 4 hours after irradiation. Phage administered 1 hour before or 1 hour after irradiation were not recovered from tumors. These data indicate that the optimal time of administration is beyond 1 hour after irradiation.

For in vivo screening, tumors were irradiated with 3 Gy and approximately $10^{10}$ phage (prepared as described in Example 4) were administered by tail vein injection into each of the tumor bearing mice at 4 hours following irradiation. Tumors were recovered at one hour following injection and amplified in BL21 bacteria. Amplified phage were pooled and re-administered to a tumor-bearing mouse following tumor irradiation. The phage pool was sequentially administered to a total of 6 animals. As a control, wild type phage lacking synthetic peptide inserts were identically administered to a second experimental group of animals.

To determine the titer of phage binding in a tumor or in normal tissue, recovered phage were amplified in BL21 bacteria. Bacteria were plated and the number of plaques present were counted. To determine the total phage output per organ, the number of plaque forming units (PFU) on each plate was divided by the volume of phage plated and the weight of each organ. Normal variation was observed as a 2-fold difference in PFU.

In the present study, background binding within tumor blood vessels was approximately $10^4$ phage. Phage that bound to the vasculature within irradiated tumors show enrichment in the tumor relative to other organs and enrichment in the irradiated tumor relative to the control phage without DNA insert. Phage that home to irradiated tumors showed a background level of binding in control organs that was lower than control phage without DNA insert.

Following 6 rounds of in vivo screening, fifty recombinant phage peptides that bound within irradiated tumors were randomly selected for further analysis. The nucleic acid sequence encoding recombinant phage was amplified by PCR using primers set forth as SEQ ID NOs: 14-15 (available from Novagen, Madison, Wis., United States of America). An individual phage suspension was used as template. Amplified peptides were sequenced using an ABI PRISM 377 sequencer (PE Biosystems, Foster City, Calif., United States of America). The sequences of the encoded peptides are listed in Table 1. Several conserved subsequences were deduced from the recovered peptides and are presented in Table 2.

Peptide sequences recovered from both tumor types include NHVGGSSV (SEQ ID NO: 1), NSLRGDGSSV (SEQ ID NO: 2), and NSVGSRV (SEQ ID NO: 4). Of the peptide sequences recovered from 6 irradiated tumors, 56% had the subsequence GSSV (SEQ ID NO: 5), 18% had the sequence RGDGSSV (SEQ ID NO: 6), and 4% had the sequence GSRV (SEQ ID NO: 7). Approximately 22-40 of $10^6$ injected phage were recovered from irradiated tumors having a peptide insert comprising the subsequence GSSV (SEQ ID NO: 5). By contrast, no phage were from irradiated tumors following administration of $10^6$ wild type phage.

TABLE 1

Peptides Identified by In Vivo Screening of LLC and GL261 Tumors

| Peptide Sequence | Number of Phage Recovered from LLC tumors (Frequency) | Number of Phage Recovered from GL261 tumors (Frequency) |
| --- | --- | --- |
| NHVGGSSV (SEQ ID NO: 1) | 7 (28%) | 12 (48%) |
| NSLRGDGSSV (SEQ ID NO: 2) | 7 (28%) | 2 (8%) |
| NSVRGSGSGV (SEQ ID NO: 3) | 7 (28%) | 0 |
| NSVGSRV (SEQ ID NO: 4) | 1 (4%) | 3 (12%) |
| Unique Sequences | 3 (12%) | 8 (32%) |

TABLE 2

Conserved Motifs within Peptides Identified by In Vivo Screening

| Conserved Sequence | | Frequency of Recovery |
| --- | --- | --- |
| GSSV | (SEQ ID NO: 13) | 56% |
| GSXV | (SEQ ID NO: 8) | 78% |
| NSXRGXGS | (SEQ ID NO: 9) | 32% |
| NSV | (SEQ ID NO: 10) | 22% |
| NSXR | (SEQ ID NO: 11) | 32% |
| NXVG | (SEQ ID NO: 12) | 46% |

Example 6

Peptide Targeting in Additional Tumors

The binding properties of phage encoding NHVGGSSV (SEQ ID NO: 1), NSLRGDGSSV (SEQ ID NO: 2), NSVRGSGSGV (SEQ ID NO: 3), and NSVGSRV (SEQ ID NO: 4) were additionally characterized in a B16F0 melanoma model. Peptides set forth as SEQ ID NOs: 1 and 2 bound within the melanoma, lung carcinoma, and glioma tumor models. SEQ ID NO: 3 bound within glioma and melanoma, and SEQ ID NO: 4 bound within lung carcinoma and glioma.

Example 7

Characterization of Peptide Binding to Irradiated Tumors

To determine where recombinant peptides bind in tumor blood vessels, the biodistribution of biotinylated peptides was assessed. Tumors were treated with 3 Gy and biotinylated peptides were administered by tail vein at 4 hours following irradiation. Tumors were recovered 30 minutes following administration of biotinylated peptides. Tumors were snap frozen and sectioned on a cryostat. Frozen sections were then incubated with Avidin-FITC (fluorescein isothiocyante) and imaged by fluorescent microscopy. Recombinant peptides (for example, those set forth in Table 1) were observed to bind the vascular endothelium within tumor blood vessels.

The anti-$\alpha_{2b}\beta_3$ monoclonal antibody was administered by tail vein to determine whether this receptor is required for recombinant phage binding in irradiated tumors. Phage encoding SLRGDGSSV (SEQ ID NO: 5) on the capsid protein were injected immediately after blocking antibody or control antibody. Phage were recovered from the tumor and controls organs and quantified by plaque formation. Radiation induced a 4-fold increase in phage binding in tumor. Blocking antibody eliminated induction of phage binding, while control antibody to P-selectin (on activated platelets) did not reduce phage binding. Thus, the tumor binding activity of targeting peptide SLRGDGSSV (SEQ ID NO: 5) is dependent on its interaction with the $\alpha_{2b}\beta_3$ receptor.

Example 8

Production of a Phage-Displayed scFv Antibody Library

A phage-displayed antibody library was constructed based upon previously published methodologies (see Pope et al., 1996). Briefly, spleens from outbred newborn and three-to-four week old mice and rats were used as a source of antibody-encoding genetic material to produce a library of about 2×10⁹ members. The antibody-encoding genetic material was cloned into the pCANTAB phagemid vector.

The pCANTAB vector contains an amber stop codon that is located downstream of the scFv coding sequences and upstream of the M13 gene III coding sequences. *E. coli* TG1 cells (a sup E strain of *E. coli*) contain a suppressor tRNA that inserts a glutamic acid residue in response to an UAG (amber) stop codon. The amber stop codon is about 14% efficient. Therefore, the scFv antibody amino acid sequences will be fused to M13 phage gene III amino acid sequences about 14% of the time, and will be produced as a soluble, non-fusion protein about 86% of the time when the library is grown in TG1 cells. In contrast, *E. coli* strain HB2151 does not contain the amber stop codon, and thus only soluble non-fused scFv will be produced when the library is grown in HB2151.

Example 9

In Vivo Screening for Antibody Ligands to Radiation-Inducible Neoantigens

A phage library comprising diverse single chain antibodies was prepared in M13 phage. Briefly, nucleotide sequences encoding antibody $V_L$ and $V_H$ regions separated by a (Gly$_4$Ser)$_3$ linker were fused to M13 gene III nucleotide sequences. When a recombinant M13 carrying these antibody-gene III fusions infects an appropriate host bacterium, the host produces recombinant M13 phage that display scFv antibody polypeptides ($V_L$—linker—$V_H$) fused to gene III protein.

The phage library was exposed to the radiation-inducible neoantigens P-selectin (also called CD62P; GENBANK™ Accession No. P98109) and/or platelet membrane glycoprotein IIB (also called CD41; GENBANK™ Accession No. P08514) immobilized on glass slides. Phage were selected based on antigen binding, and selected phage were pooled as a biased library. For representative in vitro screening methods, see Fowlkes et al., 1992; Haaparanta & Huse, 1995; Jung & Pluckthun, 1997; Peter et al., 2000; Holzem et al., 2001; Chiu et al., 2000.

Phage identified by in vitro screening were tested on Western immunoblots to confirm binding to the P-selection and platelet membrane glycoprotein IIB neoantigens. Phage that specifically bound P-selectin and platelet membrane glycoprotein IIB were subsequently used for in vivo screening of irradiated tumors as described in Example 5. Wild type phage were used as internal controls. Antibodies having substantial affinity for irradiated tumors were identified by observing an increased number of phage in the irradiated tumor when compared to a number of phage in a control organ (e.g., liver and lung). Phage antibodies with the greatest affinity for tumors were identified using the formula: number of phage in irradiated tumor/number of phage in each organ.

Several antibodies that bound P-selectin and several other antibodies that bound platelet membrane glycoprotein IIB were recovered following in vivo screening to irradiated tumors. Representative targeting antibodies identified by this method include the single chain antibodies set forth as SEQ ID NOs: 18, 20, 22, and 24 (encoded by SEQ ID NOs: 17, 19, 21, and 23 respectively), that recognize the radiation-inducible neoantigens P-selectin and platelet membrane glycoprotein IIB.

Examples 10-13

Delivery Vehicles for Use in X-Ray Guided Drug Delivery

Examples 10-13 pertain to site-specific drug delivery systems that bind to irradiated tumor blood vessels. In Examples 10-13, radiation-inducible targets, including integrin 3 (component of receptors GPIIb/IIIa and $α_vβ_3$), for the delivery vehicles are described. The drug delivery methods and compositions of the presently disclosed subject matter, including those described in Examples 10-13, are applicable to all vascularized neoplasms, thereby eliminating the problem of tumor-type specificity.

As disclosed herein above, ionizing radiation can be used to guide drugs to specific sites such as neoplasms or aberrant blood vessels. When blood vessels are treated with ionizing radiation, they respond by expressing a number of cell adhesion molecules and receptors that participate in homeostasis (referred to herein as "radiation-inducible targets"). Mass spectrometry has been used to study protein expression within tumor blood vessels. A number of proteins have been characterized. One such protein is the integrin $β_3$. Other examples of radiation-inducible molecules in blood vessels include ICAM-1, Endoglin, E-selectin, and P-selectin.

Antibody binding to radiation-inducible targets such as the cell adhesion molecules (CAMs) ICAM-1, E-selectin, and P-selectin, Endoglin, and the $β_3$ integrin subunit is also disclosed herein. Ionizing radiation induces oxidative injury in the endothelium. The endothelium responds to maintain homeostasis by preserving the barrier function in blood vessels. This is accomplished by activation of inflammation and platelet aggregation. The mechanism by which radiation activates these homeostatic responses is, in part, through the induction of cell adhesion molecules. This requires the activation of the transcription factor NFκB, which regulates transcription of the ICAM-1 and E-selectin genes (Hallahan, 1995a; Hallahan, 1996b; Hallahan, 1998b). ICAM-1, E-selectin, and P-selectin are induced by X-irradiation of the endothelium and bind to receptors on circulating leukocytes to initiate inflammation.

P-selectin (GMP140, CD62P) contributes to the inflammatory response following translocation from the cytoplasm of the vascular endothelium to the luminal surface of irradiated blood vessels. P-selectin is a cell adhesion molecule (CAM) that is sequestered in storage reservoirs within the vascular endothelium and granules in platelets. This CAM is translocated to the blood-tissue interface of the endothelium, and is not released from storage reservoirs, but remains tethered to the endothelial cell membrane (Johnston, 1989). P-selectin is rapidly translocated to the vascular lumen after tissue injury to initiate the adhesion and activation of platelets and leukocytes (Malik, 1996).

As disclosed herein, the histologic pattern of P-selectin expression in irradiated tumor blood vessels was studied and it was observed that P-selectin was localized within the endothelium of tumor vessels prior to treatment. At one hour following irradiation, P-selectin was localized to the lumen of blood vessels. P-selectin localization to the vascular lumen was present in all tumors and all species studied. Irradiated intracranial gliomas showed P-selectin localization to the vascular lumen within one hour, whereas blood vessels in normal brain showed no P-selectin staining in the endothelium and no localization to the irradiated vascular lumen.

An additional paradigm of radiation-inducible targets for drug delivery is activation (conformational changes) of receptors within irradiated blood vessels. The integrin $\beta_3$ (a component of receptor GPIIb/IIIa, $\alpha_{2b}\beta_3$) is activated and accumulates in the lumen of irradiated tumor blood vessels. Glycoproteins (GP) IIb and IIIa are members of the integrin superfamily and are the predominant surface glycoproteins in the platelet plasma membrane (Hawiger & Timmons, 1992). These glycoproteins form a heterodimer GPIIb/IIIa (Carrell, 1985). Platelets contain several integrins, including the collagen receptor $\alpha_2\beta_1$, the fibronectin receptor $\alpha_5\beta_1$, and the vitronectin receptor $\alpha_v\beta_3$. Of these integrins, GPIIb/IIIa appears to be unique in that it is the only integrin that is restricted to platelets and cells of megakaryoblastic potential.

Human fibrinogen interacts with binding sites exposed on GPIIb/IIIa of stimulated platelets through the tentacles present on γ and α chains (Hawiger, 1982). The 12-residue carboxyl-terminal segment of the γ chain, encompassing residues 400-411, was pinpointed by Hawiger and others as the platelet receptor recognition domain. See e.g. Hawiger & Timmons, 1992. Hawiger also showed that the sequence—RGD (amino acids 95-98) and (amino acids 572-575) are involved in the interaction of human fibrinogen α chain with receptors on activated platelets (Hawiger et al., 1989), but these regions are not essential for fibrinogen binding. Both domains contain the sequence RGD, identified previously as the cell recognition site of fibronectin. The presence of three domains on each half of the fibrinogen molecule, provides conditions for tighter binding of fibrinogen to platelets and for their subsequent aggregation A fibrinogen molecule comprises three pairs of nonidentical chains arranged in an anti-parallel configuration. The platelet receptor recognition domains encompass sequence 400-411 on the γ chain. RGD sequences 95-98 and 572-575 on the α chain bind, but are not essential. One fibrinogen molecule can be engaged in trans and cis interactions with platelet receptor GPIIb/IIIa.

Thus, identified herein are several radiation-inducible target proteins in blood vessels. These include E-selectin, ICAM-1, P-selectin, and the $\beta_3$ integrin, which are expressed at radiation doses as low as 2 Gy. E-selectin and ICAM-1 are induced at the level of transcription in the vascular endothelium in response to ionizing radiation exposure. Levels of E-selectin protein and RNA induction following irradiation of vascular endothelial cells increase seven- to ten-fold. Likewise, levels of ICAM protein and RNA induction following irradiation of the endothelium increase approximately three-fold.

In addition to the transcriptional induction of genes in the vascular endothelium, preexisting proteins are translocated or activated following X-irradiation. For example, as disclosed herein, P-selectin is stored in a storage reservoir (Weibel Palade bodies), which undergo exocytosis in response to X-irradiation. P-selectin expression on the surface of endothelial cells in response to ionizing radiation has been observed. P-selectin accumulation within the lumen of tumor microvasculature following tumor irradiation was also observed. This response occurs at therapeutic doses of radiation (2 Gy) and typically occurs within one hour of X-irradiation.

$\beta_3$ also accumulates within the lumen of blood vessels in response to radiation. $\beta_3$ is associated with integrins $\alpha_v$ or $\alpha_{2b}$ to form heterodimers $\alpha_{2b}\beta_3$ and $\alpha_v\beta_3$. The heterodimer $\alpha_{2b}\beta_3$ is the component of a receptor on activated platelets, glycoprotein IIb/IIIa (GPIIb/IIIa), while $\alpha_v\beta_3$ is the vitronectin receptor. As disclosed herein, while several other radiation-inducible molecules can be targeted within tumor blood vessels, the $\beta_3$ target for drug delivery is an exemplary target for site-specific peptide binding within tumor blood vessels following irradiation.

As set forth in Examples 10-13, peptides and antibodies that bind to $\beta_3$ have been studied. $\beta_3$-binding proteins have been conjugated to fluorochromes and radionuclides to determine whether specific binding of peptides occurs within irradiated tumors. Immunofluorescent and immunohistochemical staining of $\beta_3$ within the lumen of blood vessels immediately following irradiation has been observed. Drug delivery to irradiated tumors in accordance with the presently disclosed subject matter has been studied through the analysis of ligands to $\beta_3$ (vitronectin, von Willebrand factor, fibronectin, and fibrinogen). $^{131}$I was conjugated to these ligands to determine the biodistribution in tumor bearing mice. These studies demonstrated that $^{131}$I-fibrinogen binds specifically to tumors following exposure to ionizing radiation.

Immunoconjugates directed to radiation-inducible neoantigens in accordance with the presently disclosed subject matter circumvent the limitation associated with attempts in the prior art to prepare immunoconjugate delivery vehicles in that prior art immunoconjugates are limited to certain tumor types. In contrast, because antigens that are induced in irradiated vessels in all tumor types have been selected for use in the methods and compositions of the presently disclosed subject matter, all tumor types can be targeted. This is possible because it has been observed in that the endothelium and blood components respond to oxidative stress in a similar, if not identical manner in all tumors.

Examples 10-13 provide data that demonstrates improved bioavailability and biodistribution of therapeutic agents to irradiated tissues in animal models. The methods and compositions of the presently disclosed subject matter thus provide for an increase in the bioavailability of therapeutic agents at biologically active sites, and for a reduction in toxicity by directing treatment specifically to the neoplasm or the site of angiogenesis. Thus, an aspect of the presently disclosed subject matter is to target drug delivery to these radiation-inducible molecules through antibody conjugate delivery vehicles, protein conjugate delivery vehicles and peptide conjugate delivery vehicles.

Site-specific drug delivery to radiation-inducible antigens is adaptable to many compounds and therapeutic approaches. In this regard, any suitable therapeutic agents, including but not limited to cytotoxins, biologicals, gene therapy vectors, and radionuclides, can be incorporated into a delivery vehicle of the presently disclosed subject matter.

Materials and Methods Employed in
Examples 10-13

Linking Compounds. Linking compounds include 1,3,4,6-tetrachloro-3a,6a-diphenylglcouril (a reagent sold under the registered trademark IODO-GEN®), and MPBA, each available from Pierce Biotechnology, Inc. (Rockford, Ill., United States of America). The IODO-GEN® reagent reacts with tyrosine residues, while MPBA reacts with cysteine residues, both of which are not on the peptide HHLG-GAKQAGDV (SEQ ID NO: 16). An advantage of the IODO-GEN® reagent is that it is supplied in coated tubes and beads to eliminate contamination of the injectable material, whereas MPBA is in powder form. Initial experiments use the IODO-GEN® reagent to iodinate a poly-tyrosine peptide derivative of HHLGGAKQAGDV-SGSGS (SEQ ID NO: 26), HHLGGAKQAGDV-SGSGS-YYYYY (SEQ ID NO: 28), and additional experiments use MPBA to iodinate poly-Cys.

Preparation and Radioiodination of Peptides. An IODO-GEN®-plated reaction vessel (Pierce Biotechnology, Inc.) is rinsed with a small amount of sterile saline to remove any loose microscopic flakes of the iodination reagent. The desired amount of carrier-free $^{125}$I sodium iodide, a specific activity of 100 mCi/mg protein, is added to the reaction vessel, followed by the reconstituted peptides suspension. The reaction vessel is then sealed off and the reaction is allowed to proceed for 20 minutes at room temperature with constant gentle agitation of the reaction vessel. The iodination process is terminated by removing the reaction mixture from the reaction vessel into a centrifugation tube. The reaction mixture is centrifuged at 3,000 rpm for 15 minutes. The supernatant is removed and the residue is reconstituted in 5 ml sterile normal saline.

Pinhole Gamma Camera Imaging of Peptide Biodistribution. A dedicated research single-head gamma camera (20 cm×40 cm active imaging area) fitted with a cone-shaped pinhole collimator is used for nuclear medicine animal imaging experiments. The pinhole collimator, equipped with a 4 mm aperture Tungsten insert, is used to acquire pre-treatment and serial, post-treatment follow-up images of each animal in order to determine the temporal distribution of peptide in vivo. Each pinhole acquisition comprises a planar view acquired for 3 minutes using a 256×256 pixel acquisition matrix. In order to maximize pinhole collimator-gamma camera system sensitivity, a source-to-aperture distance on the order of 2 cm to 5 cm is maintained. The spatial distribution of peptide within each image is measured using quantitative, region of interest (ROI) analysis. Two different size ROIs are used in both the tumor region and mouse background in order to quantify image counts and isolate any possible influence of ROI size on quantification. A 2×2 (small) and 11×11 (large) pixel ROI are used to record image counts in the tumor and other organs in the mouse. The angular dependence of pinhole efficiency is measured using a flat, uniform sheet source of activity. Image counts are then corrected for decay and this geometric effect.

Statistical Considerations. Internal controls are established in each animal by use of an untreated control tumor implanted on the left hind limb and irradiation of the right hind limb tumor, as described in Hallahan, 1995b and Hallahan, 1998.

Sample Size and Power Analysis. In order to calculate the statistical significance of differences between groups of mice, eight mice are studied at each time to determine statistical significance. In general, a sample size of eight per group gives about 80% of power to detect a difference of 1.5-fold standard deviations in the interesting parameters between two groups with a two-sided statistic equal to 5%.

Statistical Analysis Plan. Pharmacokinetic parameters are presented in tabular and graphic form. Pharmacokinetic parameters such as maximal plasma concentration, time of maximal concentration, and area under the plasma concentration time curve are determined using non-compartmental methods. Statistical analyses are performed using the General Linear Model method of the Statistical Analysis System (SAS). If significant differences are indicated by the ANOVA analysis, the Waller-Duncan K-ratio t-test procedure is used for pairwise comparisons of mean pharmacokinetic parameter values.

For the single time point data, tests of hypotheses concerning correlation between imaging results and results are completed using the paired t-test or Wilcoxon Signed-Rank test for the interesting continuous parameters or the McNemar's Chi-square test for the interesting categorical parameters. For either count or binary multiple time points data, tests concerning correlation between imaging results and pharmacokinetic results are made using the Generalized Estimating Equation (GEE) method statistical procedure for longitudinal data analysis with multiple observable vectors for the same subject (Diggle, 1994; Liang, 1986). For continuous multiple time points data, tests concerning correlation between groups are completed using the restricted/residual maximum likelihood (REML)-based repeated measure model (mixed model analysis; Jennrich, 1986) with various covariance structure.

The statistical analyses are completed by SAS 6.12 statistical program, or SAS IML macro in this project. Computer connections, when necessary, are attained via a Novell network using the Internet Packet eXchange (IPX) protocol.

Example 10

X-Ray-Guided Drug Delivery via Antibody Delivery Vehicles

Following platelet activation, several antigens are expressed on the surface of platelets. Indeed, it has been observed that irradiation of animal tumors increases the expression of platelet antigens such as P-selectin and GPIIb/IIIa. As disclosed herein above, antibodies can be conjugated to radionuclides, cytotoxic agents, gene therapy vectors, liposomes, and other active agents. In this Example, the administration of radioimmunoconjugate delivery vehicles against platelet antigens following irradiation of tumors is disclosed.

Anti-GPIIb/IIIa antibodies (R&D Systems, Inc., Minneapolis, Minn., United States of America) are labeled with $^{131}$I using IODO-GEN® reagent (Pierce Biotechnology, Inc., Rockford, Ill., United States of America). Labeled antibody is separated from free iodine by use of column chromatography. Radioimmunoconjugates are injected into mice by tail vein. Hind limb tumors are implanted and treated as described herein above. The optimal time of administration of radioimmunoconjugates is determined.

In separate experiments, procoagulants such as DDAVP are also administered to enhance radioimmunoconjugate binding to activated platelets in irradiated tumors. Mouse subjects are imaged by gamma camera as described herein above. PHOSPHORIMAGER™ plates and histologic sections with immunohistochemistry as described herein above are used to validate image processing. In the event that certain radioimmunoconjugates do not achieve specific activity within tumors that is sufficient to image or treat tumors, multiple radionuclides are incorporated into the antibody delivery vehicles.

In additional experiments, Fab' fragments of anti-GPIIIa and anti-GPIIb antibodies are also employed in binding in a site-specific manner to irradiated tumors. It is shown herein that anti-GPIIIa antibody staining in blood vessels following X-irradiation. There are two approaches in producing antibodies for site-specific binding. The first is cleavage of the IgG antibody to form the Fab' fragment. The second approach is the use of phage antibodies to GPIIIa and GPIIb that are produced in the Vanderbilt Cancer Center Molecular Discovery Core Laboratory using phage-display techniques. Each of these approaches yields low molecular weight antibodies that can be efficiently produced for clinical studies. Specificities of the GPIIIa (integrin $\beta_3$) antibodies and antibody fragments are compared to the specificities of the GPIIb antibodies and antibody fragments to establish potentially useful reagents and in that GPIIIa is also found in $\alpha_v\beta_3$.

Experimental Design. The anti-GPIIIa and anti-GPIIb antibodies (R&D Systems, Inc.) are cleaved to form the Fab' fragment. This fragment is isolated from the Fc fragment by columns. In addition, GPIIIa protein is screened with a phage library within the Vanderbilt Cancer Center Molecular Discovery Core Laboratory. Antibody from phage is grown up in the bacteria. Antibodies are then studied for binding in irradiated tumors. Antibodies are labeled with $^{131}$I using IODO-GEN® reagent as described above. The molar ratio of $^{131}$I to antibody is optimized to avoid potential reduction in the affinity of antibody binding due to $^{131}$I.

Tumors are implanted and irradiated as described herein. Radio-immunoconjugates are administered immediately after irradiation using tail vein injection. Eight mice are randomly assigned into experimental and control groups. Imaging and quantification of $^{131}$I are performed as described above. Statistical analysis is performed as described above.

Positive control groups. Radiolabeled fibrinogen is administered to irradiated tumor bearing mice and compared to radioimmunoconjugates. These mice are randomly assigned into groups during the same experiment as radio-immunoconjugates.

Negative control groups. Non-irradiated control tumors are implanted in the left hind limb of all mice. Secondly, radiolabeled anti-$\alpha_v$ and anti-human IgG antibodies are administered to tumor bearing mice following irradiation to verify that antibody binding to irradiated tumors is not a generalized phenomenon.

Example 11

X-Ray-Guided Drug Delivery Targeted to Radiation-Inducible Neoantigens in Blood Vessels Radiation-inducible targets for drug delivery systems will be most useful if they are not tumor-specific. The vascular endothelium is an essential component to nearly all neoplasms. As disclosed herein above, radiation response is similar across a wide range of tumor types. In particular, P-selectin exocytosis, von Willebrand Factor release, and platelet aggregation are observed within all tumor blood vessels following irradiation. In this Example, antibody delivery vehicles for X-ray-guided drug delivery to the vascular endothelium of tumors are disclosed. Antibody delivery vehicles adhere to antigens released into the lumen and are thus obstructed from circulating beyond the confines of the tumor. In view of the targeting of vascular endothelium, this Example is also illustrative of the methods of treating angiogenesis in accordance with the presently disclosed subject matter disclosed herein above.

Additionally, one level of radiation-inducible expression of receptors and adhesion molecules is the activation of inactive receptors following irradiation of tumor blood vessels. Tumors in the hind limb of mice were treated with 2 Gy ionizing radiation followed by sectioning and immunohistochemical staining for the $\beta_3$ integrin in the tumor sections. The observed histologic pattern of staining showed that both platelets and endothelium stain with anti-$\beta_3$ antibody after irradiation, but not prior to irradiation. Thus, therapeutic doses of irradiation (2 Gy) were and are sufficient to induce the accumulation of integrin $\beta_3$ within tumor blood vessels within 1-4 hours of irradiation.

Hind limb tumors are implanted into mice and treated with radiation as described in Hallahan et al., 1998a. Radio-immunoconjugate delivery vehicles are prepared using anti-E-selectin and anti-P-selectin antibodies (R&D Systems, Inc.), IODO-GEN® reagent (Pierce Biotechnology, Inc.) and $^{131}$I. Radiolabeled antibodies are separated from free $^{131}$I by use of column chromatography. The delivery vehicles are injected via tail vein into mice with hind limb tumors following treatment with irradiation. Mice are imaged with gamma camera imaging as described herein above. Image processing is validated by use of PHOSPHORIMAGER™ plates, immunofluorescence, and immunohistochemistry as described herein above.

One potential limitation of this embodiment of the presently disclosed subject matter is that anti-E-selectin antibody binding occurs in untreated normal tissues such as the lung. The importance of validation of the tumor specificity for radioimmunoconjugate delivery vehicles is that the ideal radiation-inducible antigens have substantially no constitutive expression in any tissue, but prolonged expression in tumor blood vessels. Thus, pharmacokinetics and biodistribution of the anti-E-selectin and anti-P-selectin antibody delivery vehicles are also determined.

Example 12

X-Ray-Guided Drug Delivery by Use of a Twelve Amino Acid Segment of the γ Subunit of Fibrinogen This Example pertains to the use of the dodecapeptide HHLGGAKQAGDV (SEQ ID NO: 16), a segment of the γ subunit of fibrinogen, to achieve site-specific binding to irradiated tumors. This peptide segment of the carboxyl terminus of the fibrinogen γ chain binds to GPIIb/IIIa following platelet activation. The fibrinogen binding sequence (HHLGGAKQAGDV; SEQ ID NO: 16) is sufficient for site-specific localization to irradiated tumors.

Observations. The peptide sequence within fibrinogen that binds to the activated GPIIb/IIIa receptor is the dodecapeptide HHLGGAKQAGDV (SEQ ID NO: 16). To determine whether HHLGGAKQAGDV (SEQ ID NO: 16) binds in irradiated tumors, applicant utilized the peptide HHLGGAKQAGDV (SEQ ID NO: 16) linked to biotin by a serine-glycine linker (HHLGGAKQAGDV-SGSGSK-biotin; SEQ ID NO: 30). This peptide was synthesized in the Vanderbilt University Peptide Core Lab and biotinylated at the carboxyl terminus. The resulting HHLGGAKQAGDV-SGSGSK-biotin (SEQ ID NO: 30) was administered by tail vein injection into tumor bearing mice. B16F0 tumors in the hind limb were treated with sham irradiation (control), 4 Gy irradiation followed by HHLGGAKQAGDV-SGSGSK-biotin (SEQ ID NO: 30) injection, or HHLGGAKQAGDV-SGSGSK-biotin (SEQ ID NO: 30) followed by tumor irradiation (4 Gy). Tumors were frozen at 4 hours and sectioned for fluorescence staining. Avidin-FITC was incubated with tumor sections and imaged by UV microscopy. Avidin-FITC stained blood vessels were observed in irradiated tumors, but not in untreated control. Moreover, it was found that HHLGGAKQAGDV (SEQ ID NO: 16) administration prior to irradiation is a more efficient schedule of administration as compared to radiation before dodecapeptide administration.

Design of Iodination Experiments. Tumors are implanted and irradiated as described herein above. The synthetic dodecapeptide encompassing the sequence HHLGGAKQAGDV (SEQ ID NO: 16) on the carboxyl-terminal segment of fibrinogen γ chain binds to GPIIb/IIIa is prepared, and a peptide tail for radioiodination (SGSGS-YYYYY; SEQ ID NO: 32) is added. The peptide tail is commercially available from PeptidoGenic Research & Co. (Livermore, Calif., United States of America). A sample from each batch is sequenced in accordance with standard techniques for quality control.

HHLGGAKQAGDV-SGSGS-YY (SEQ ID NO: 28) is labeled with $^{131}$I using IODO-GEN® reagent as described above. When tumors are grown to 0.5 cm in diameter, the tail vein of each mouse subject is cannulated and $^{131}$I-labeled HHLGGAKQAGDV-SGSGS-YYYYY (SEQ ID NO: 28) is injected. The injection tubing and syringe is counted after the injection to measure residual $^{131}$I. Immediately after administration of $^{131}$I-peptide, tumors are irradiated using techniques described herein and by Hallahan et al., 1998. Mice are imaged by gamma camera imaging at 1 and 24 hours after irradiation. $^{131}$I-labeled HHLGGAKQAGDV-SGSGS-YYYYY (SEQ ID NO: 28) binding to tumors is quantified by gamma camera imaging and direct well counts from excised tumors as described above. Tissue sections of all organs are analyzed. Eight tumor-bearing mice are randomly assigned into each of the experimental and control groups. Statistical considerations are addressed as described above.

Positive control groups. Radioiodinated-fibrinogen is administered to irradiated tumor bearing mice and compared to radioiodinated-peptide. These mice are randomly assigned into groups during the same experiment as radiolabeled peptides.

Negative control groups. Non-irradiated control tumors are implanted in the left hind limb of all mice. Secondly, radiolabeled SGSGSGSSGSGSSGSGS-YYYYY (SEQ ID NO: 33) are administered to tumor bearing mice following irradiation to verify that peptide binding to irradiated tumors is not a generalized phenomenon.

It is noted that the three-dimensional conformation of fibrinogen might facilitate site-specific binding to irradiated tumors. Alternatively, $^{131}$I labeling might interfere with peptide binding to GPIIb/IIIa. A longer peptide linker and fewer Tyr residues are options that are employed in each case.

Example 13

Liposome Delivery Vehicle Comprising Twelve Amino Acid Segment of the γ Subunit of Fibrinogen This Example pertains to the preparation of liposomes that are conjugated to the dodecapeptide HHLGGAKQAGDV (SEQ ID NO: 16), a segment of the γ subunit of fibrinogen, to achieve site-specific binding to irradiated tumors.

In initial experiments, 1,1'-Dioctadecyl-3,3,3',3'-tetramethylindocarbo-cyanine perchlorate (DiI), a lipid fluorescent marker, was added to liposome-fibrinogen conjugates and injected by tail vein. As a control, liposomes without fibrinogen conjugation were injected. These produced no increase in fluorescence in irradiated tumors. Fluorescence within blood vessels of tumors treated with ionizing radiation was observed for the liposome-fibrinogen conjugates. These findings support site-directed drug delivery to the fibrinogen receptor in irradiated tumors.

Cationic liposomes can be conjugated to antibodies and peptides (Kirpotin et al., 1997); however, these liposomes bind to lipophilic proteins in the serum, which reduces the circulation time. Therefore, polyethylene glycol (PEG) is used to coat the drug delivery systems. PEG prolongs circulation time (Nam et al., 1999; Koning et al., 1999).

In this Example, HHLGGAKQAGDV (SEQ ID NO: 16) is conjugated to liposomes and encapsulated by PEG. It is then determined whether both large MW therapeutic proteins and small MW cytotoxic compounds can be localized to irradiated tumors by liposomes conjugated to HHLGGAKQAGDV (SEQ ID NO: 16). The linking peptide SGSGS (SEQ ID NO: 31) is placed at the C-terminus, which is linked to liposomes. Liposomes are conjugated to the SH on Cys at the C-terminus. The biodistribution of HHLGGAKQAGDV-SGSGSC (SEQ ID NO: 29)-liposome is studied and the length of the linking peptide is altered as necessary. In the event that PEG will not achieve membrane fusion that is comparable to cationic liposomes, the length of the linking peptide is also altered as necessary.

Preparation of HHLGGAKQAGDV (SEQ ID NO: 16)-Long Circulatory Liposomes. Two methods of conjugating liposomes to peptides are employed. The first method conjugates the liposome to the N-terminus, and thus the linking peptide is placed at the N-terminus. This method arranges the conjugate in the following configuration: liposome-SGSGS-HHLGGAKQAGDVC (SEQ ID NO: 27). The second method conjugates the liposome to the C-terminus of the peptide. This method is facilitated by placing a Cys residue at the C-terminus. This method arranges the conjugate into the configuration: HHLGGAKQAGDV-SGSGSC (SEQ ID NO: 29)-liposome. These two methods provide alternatives in the event that one configuration is useful for site-specific drug delivery over the other configuration. These methods are also applicable to larger polypeptides and proteins, including fibrinogen itself.

Method 1

Step (1) Synthesis of Maleimide-PGE-PE

The lipophilic SH reactive reagent with a long spacing arm is synthesized from maleimide-PEG 2000-NHS ester (Prochem, High Point, N.C., United States of America), dioleoylphosphatidylethanolanime (DOPE, Avanti Polar Lipids, inc., Alabaster, Ala., United States of America), and triethylamine in chloroform (1:1:1.5). Resulting maleimide-PEG 2000-DOPE is purified by flash column.

Step (2) Preparation of Thiolated HHLGGAKQAGDV (SEQ ID NO: 16)

Under stirring, to a solution of HHLGGAKQAGDV (SEQ ID NO: 16; 2 mg/mL) in 0.01 M HEPES 0.15 M NaCl buffer pH 7.9, containing 10 mM EDTA and 0.08% sodium azide, is added in five-fold excess of freshly prepared Traut's Reagent in the same buffer. Reaction is performed for 30 minutes at 0° C. Thiolated HHLGGAKQAGDV (SEQ ID NO: 16) is then purified using a desalting PD-10 column (Amersham Biosciences).

Preparation of maleimide-containing long circulating liposomes with fluorescent labels. PGE 2000-PE, cholesterol, Dipalmitoyl phosphocholine (Avanti Polar Lipids), DiI, and maleimide-PEG-2000-DOPE is dissolved in chloroform and mixed at a ratio of 10:43:43:2:2 in a round bottom flask as described in Leserman, 1980. The organic solvent is removed by evaporation followed by desiccation under vacuum for 2 hours. Liposomes are prepared by hydrating the dried lipid film in PBS at a lipid concentration of 10 mM. The suspension is then sonicated 3×5 minutes until clear, forming unilamellar liposomes of 100 nM in diameter.

Conjugation of thiolated HHLGGAKQAGDV (SEQ ID NO: 16) to maleimide containing liposomes. Prepared vesicles and thiolated protein is mixed in 10 mm HEPES, 0.15 M NaCl, and EDTA pH 6.5. The final concentrations for proteins and liposomes are 0.25 g/L and 2.5 mM, respectively. The mixture is incubated for 18 hours at room temperature and vesicles are separated from unconjugated protein by gel filtration on a SEPHAROSE® 4B-CL column (Amersham Biosciences).

Method 2

To conjugate the peptide to long-circulating liposomes, a peptide with a Cys residue on the C-terminal is synthesized (PeptidoGenic Research & Co., Livermore, Calif., United States of America). A bifunctional PEG (molecular weight 2000) with a maleic group on one end and NHS group on the other end is used to conjugate to the aminal group of dioleyol phosphatidyl ethanolamine (DOPE). The resulting maleic-PEG-DOPE serves as a sulfhydryl-reactive lipid anchor with a peptide linker between the lipid portion and the SH-reactive group. Long-circulating liposomes are prepared by reverse phase evaportation method using a lipid mixture composed of DOPC:Cholesterol:PEG-DOPE:maleic-PEG-DOPE:Cy3-DOPE at a ratio of 45:44:5:2:2 (molar ratio). The peptide is then conjugated to the liposomes at pH 7.0 under inert gas for 24 hours at room temperature. After the conjugation, the excess of peptide is removed though a gel filtration step using SEPHACRYL™-100 column with PBS as eluent. The percentage of conjugation of the peptide to the liposomes is estimated by the reduction of free peptide peak.

Experimental Design. HHLGGAKQAGDV (SEQ ID NO: 16) is conjugated to liposomes using SH-reactive group as described above. Liposomes are labeled with gamma emitters and fluorochromes so that the pharmacokinetics and biodistribution can be measured. HHLGGAKQAGDV-SGSGSC (SEQ ID NO: 29)-Liposomes are then coated with PEG as described above. Tumors are implanted and irradiated as described above. HHLGGAKQAGDV (SEQ ID NO: 16)-conjugated encapsulated drugs are then injected by tail vein injection.

Biodistribution is studied by use of gamma emitters and gamma camera imaging. Both large molecular weight proteins and small molecular weight compounds (i.e. active agents) are radiolabeled. A therapeutic protein, tumor necrosis factor is labeled with $^{131}$I by use of IODO-GEN® reagent as described above. $^{131}$I-TNF is encapsulated in liposomes-HHLGGAKQAGDV (SEQ ID NO: 16) conjugates and PEG administered by tail vein as described above.

Doxorubicin is used to study the biodistribution of a small MW compound that interacts with radiation. Doxorubicin is encapsulated in fluorescent liposomes (Avanti Polar Lipids) and PEG-HHLGGAKQAGDV (SEQ ID NO: 16) conjugates and administered by tail vein as described above. Methods of preparing fluorescent liposomes and conjugation of HHLGGAKQAGDV (SEQ ID NO: 16) to liposomes are described above, Doxorubicin levels in serum and tumors in the Pharmacokinetic core lab at Vanderbilt University using standard techniques. Fluorescence microscopy is used to measure liposomes in tumors using fluorescence quantification techniques described in Hallahan, 1997a.

Positive control groups. $^{131}$I-labeled HHLGGAKQAGDV-SGSGS-YYYYY (SEQ ID NO: 28) is administered to one group of irradiated tumor bearing mice and compared to biodistribution of encapsulated radiolabeled liposome. These mice are randomly assigned into groups during the same experiment as radiolabeled drugs. Radiolabeled drug binding in each group is quantified and compared to the $^{131}$I-labeled HHLGGAKQAGDV-SGSGS-YYYYY (SEQ ID NO: 28) positive control group.

Negative control groups: Firstly, control tumors are implanted in the left hind limb of all mice and remain unirradiated. Secondly, SGSGSSGSGSGS-SGSGS (SEQ ID NO: 34) are conjugated to PEG and liposomes and administered to tumor bearing mice following irradiation to verify that encapsulated drug binding to irradiated tumors is not a generalized phenomenon. Eight tumor-bearing mice are randomly assigned into each of the experimental and control groups. Statistical considerations are described above.

Example 14

Anti-P-Selectin scFv Binding to Microvasculature of Irradiated Cancer

To determine whether anti-P-selectin scFv antibodies bind to irradiated microvasculature, the binding of four antibodies (4A, 12F, 5H, and 10A) was studied using immunofluoresence microscopy. Human head and neck squamous cell carcinoma (HNSCC) cell lines were implanted into the hind limb of nude mice and grown to 10 mm diameter as in Example 5 (see also Hallahan et al., 1995b; Hallahan et al., 1998; Hallahan & Virudachalam, 1999). Tumors were irradiated and dissected 5 hours later. Dissected tumors were snap frozen and cryosectioned. Immunofluoresence microscopy of each of the scFv antibodies to human P-selectin demonstrated that the antigen in these tumor sections was expressed by host (mouse) cells, indicating that these epitopes are conserved across species. Each of the scFv antibodies bound to the microvasculature of irradiated HNSCC, but not to untreated controls.

Example 15

Direct Application of Library to Irradiated Tumors and Endothelial Cells

To study the feasibility of selecting antibodies that bind irradiated endothelial cells, primary culture human umbilical vein endothelial cells (HUVEC) were used. Negative selection of phage was first performed by removing all phage antibodies that bind within an intact umbilical vein and to unirradiated endothelium from pooled donors. Unbound phage were then incubated with HUVEC at 5 hours after irradiation with 2 Gy. Antibodies were prioritized by fluorometric microvolume assay technology with an FMAT™ 8100 device (PE Biosystems, Foster City, Calif., United States of America) using irradiated HUVEC in microwells. Selected were scFv antibodies that bind with high affinity to irradiated HUVEC but do not bind to untreated HUVEC. Immunofluorescence microscopy of antibodies developed to irradiated HUVEC showed that several antibodies did not bind to untreated control cells but did bind to irradiated HUVEC. These phage-displayed antibodies were not displaced by anti-P-selectin antibodies indicating that they likely bound to distinct radiation-inducible epitopes on HUVEC. A determination of which of these antibodies binds to human cancer microvasculature is presented in Example 17.

Phage antibodies that bind to irradiated HUVEC and fibroblasts using a human Fab antibody library are also selected. Enriched antibodies are prioritized and studied on biopsy specimens from irradiated HNSCC patients. Antibodies that bind to human tumor blood vessels are isolated

Example 16

In Vivo Testing of scFv Antibody Binding

Several scFv antibodies developed to P-selectin and to $\alpha_{2b}\beta_3$ are prioritized by ELISA, BIACORE®, and fluorometric microvolume assay technology (the latter using a FMAT® 8100 device from PE Biosystems, Foster City, Calif., United States of America). These antibodies are tested to determine which bind to the greatest percentage of tumor specimens from irradiated patients, while not binding to biopsies of skin and mucosa. Biopsy specimens are sectioned on the day of antibody staining, which is performed as described (Schueneman et al., 2003). Briefly, sections are first incubated with blocking buffer and washed. Fluorescence-labeled scFv and Fab antibodies are then incubated with the sections under conditions sufficient to allow binding of the antibodies to targets. Antibody staining of tumor blood vessels is compared to that of skin and mucosa biopsies from the same patients. Biopsies from patients are stained for each of the prioritized antibodies by use of fluorescence microscopy and image analysis software as has been described (Geng et al., 2001; Hallahan et al., 2002). Vascular density is also analyzed simultaneously.

HNSCC xenografts are implanted subcutaneously in the hind limb as described in Hallahan et al., 2003. Antibodies and immunoconjugates with optimal binding are radiolabeled and injected by tail vein after irradiation of xenografts. The tumor bearing hind limb is irradiated with 0 Gy (Control), or daily fractionated radiation (2 Gy×7) as described in Schueneman et al., 2003 and Hallahan et al., 2003.

Example 17

Mass Spectrometry Analysis of scFv Antibodies

To develop a high-throughput screening technique for phage library antibodies targeted to radiation-inducible neoantigens (for example, P-selectin or $\alpha_{2b}\beta_3$ integrin) and measure tumor specificity of scFv antibodies developed from phage antibody libraries, a large phage-displayed scFv recombinant antibody library was developed. The phage library was incubated with purified P-selectin protein, and high-affinity phage antibody clones were recovered by washing at pH 1. The antibody clones were assayed for antigen-binding activity by ELISA. The clones producing antibodies reactive with P-selectin were grown and induced to express P-selectin-specific scFv antibodies on a large scale.

The phage antibody library was also screened for scFv that bound to expired human platelets obtained from blood banks. Phage that were nonspecifically bound to inactivated platelets were first subtracted from the library. Platelets were activated to induce $\alpha_{2b}\beta_3$ integrin in the active conformation. Bound phage were displaced by the addition of a monoclonal antibody specific for $\alpha_{2b}$. The displaced phage were recovered and used to produce $\alpha_{2b}$ antibodies.

P-selectin and $\alpha_{2b}$ scFv antibodies were individually spotted in matrix and evaluated by mass spectrometry for size to determine sets of 6 that can be effectively discriminated by mass spectrometry based upon differences in their molecular weights (approximately 400 mass unit size difference). Antibodies to P-selectin and to $\alpha_{2b}$ were administered in sets of 6 by tail vein injection into mice bearing irradiated tumors. The tumors were dissected and antibody binding was measured by MALDI-TOF mass spectrometry.

Soluble rodent scFv antibodies to P-selectin and to $\alpha_{2b}$ were developed, several of which were definitively measured in matrix by MALDI-TOF mass spectrometry. Of these, 9 soluble rodent scFv antibodies to P-selectin and 9 soluble rodent scFv antibodies to $\alpha_{2b}$ were differentially detected in sets of 3 in mice tumors via MALDI-TOF mass spectrometry. Spectrum analysis allowed quantification of the amount of the individual antibodies binding within the tumors.

Example 18

Binding of scFv to Human Cancer Microvasculature

Using the methods and procedures described hereinabove, scFv antibodies that are found to bind to HUVEC cells are tested for binding to human cancer microvasculature either in vivo or in vitro on biopsy samples.

Negative selection of the entire phage library ($2 \times 10^9$) is first performed on untreated vascular endothelium and platelets. Phage-displayed antibodies that bind to normal endothelium and platelets are discarded, while phage that do not bind are used for high throughput screening as follows.

HUVEC cells are grown to confluence in complete medium and human serum in 1536-well plates. Cells are irradiated with 3 Gy. Those scFv phage antibodies that bind to the isolated, irradiated endothelium are selected by use of an automated colony picker, followed by high throughput screening using an FMAT® device (PE Biosystems, Inc., Foster City, Calif., United States of America), which is used to quantify fluorescence-labeled phage localized and concentrated on the irradiated endothelial cell surface.

Example 19

Laser Capture Microdissection

Microvasculature is identified during laser capture microdissection (LCM). The use of an LCM system allows selected single cells or groups of cells to be analyzed. LCM is used to dissect the vascular endothelium and luminal proteins from a frozen section of an irradiated tumor. The phage antibody library is added to these blood vessels and scFv phage antibodies that are recovered from the irradiated tumor vasculature are selected using an automated colony picker. Phage undergo several rounds of selection to reduce nonspecific binding. Identified antibodies are further selected using FMAT.

REFERENCES

The references listed below as well as all references cited in the specification are incorporated herein by reference to the extent that they supplement, explain, provide a background for or teach methodology, techniques and/or compositions employed herein.

Aboud-Pirak E, Lesur B, Rao K S, Baurain R, Trouet A & Schneider Y J (1989) Cytotoxic activity of daunorubicin or vindesin conjugated to a monoclonal antibody on cultured MCF-7 breast carcinoma cells. *Biochem Pharmacol* 38:641-648.

Adams G P (1998) Improving the tumor specificity and retention of antibody-based molecules. *In Vivo* 12:11-21.

Adams G P, McCartney J E, Wolf E J, Eisenberg J, Tai M S, Huston J S, Stafford W F 3rd, Bookman M A, Houston L L & Weiner L M (1995) Optimization of in vivo tumor targeting in SCID mice with divalent forms of 741F8 anti-c-erbB-2 single-chain Fv: effects of dose escalation and repeated i.v. administration. *Cancer Immunol Immunother* 40:299-306.

Albini A, Marchisone C, Del Grosso F, Benelli R, Masiello L, Tacchetti C, Bono M, Ferrantini M, Rozera C, Truini M, Belardelli F, Santi L & Noonan D M (2000) Inhibition of angiogenesis and vascular tumor growth by interferon-producing cells: A gene therapy approach. *Am J Pathol* 156:1381-1393.

Alexay et al., (1996) *The International Society of Optical Engineering* 2705/63.

Allen J B, Walberg M W, Edwards M C & Elledge S J (1995) Finding Prospective Partners in the Library: The Two-Hybrid System and Phage Display Find a Match. *Trends Biochem Sci* 20:511-516.

Altschul S F, Gish W, Miller W, Myers E W & Lipman D J (1990) Basic Local Alignment Search Tool. *J Mol Biol* 215:403-410.

Amemiya Y, Satow Y, Matsushita T, Chikawa J, Wakabayashi K, Miyahara J & Mandelkow E (1988) A Storage Phosphor Detector (Imaging Plate) and its Application to Diffraction Studies Using Synchrotron Radiation. *Topics Curr Chem* (Springer-Verlag), 14Z:121-144.

Andersson L, Blomberg L, Flegel M, Lepsa L, Nilsson B & Verlander M (2000) Large-scale synthesis of peptides. *Biopolymers* 55:227-250.

Arap W, Pasqualini R & Ruoslahti E (1998) Cancer treatment by targeted drug delivery to tumor vasculature in a mouse model. *Science* 279:377-380.

Ausubel F, ed (1995) *Short Protocols in Molecular Biology*, 3rd ed. Wiley, New York, United States of America.

Baillie C T, Winslet M C & Bradley N J (1995) Tumour vasculature—a potential therapeutic target. *Br J Cancer* 72:257-267.

Barton G J (1998) Protein Sequence Alignment Techniques. *Acta Crystallogr D Biol Crystallogr* 54:1139-1146.

Batzer M A, Carlton J E & Deininger P L (1991) Enhanced evolutionary PCR using oligonucleotides with inosine at the 3'-terminus. *Nucleic Acids Res* 19:5081.

Bauminger S & Wilchek M (1980) The Use of Carbodiimides in the Preparation of Immunizing Conjugates. *Methods Enzymol* 70:151-159.

Becerril B, Poul M A & Marks J D (1999) Toward selection of internalizing antibodies from phage libraries. *Biochem Biophys Res Commun* 255:386-393.

Bendixen C, Gangloff S & Rothstein R (1994) A Yeast Mating-Selection Scheme for Detection of Protein-Protein Interactions. *Nucleic Acids Res* 22:1778-1779.

Better M, Chang C P, Robinson R R & Horwitz A H (1988) Escherichia coli secretion of an active chimeric antibody fragment. *Science* 240:1041-3.

Bodanszky M (1993) *Principles of Peptide Synthesis*, 2nd rev. ed. Springer-Verlag, Berlin/New York.

Boerman O C, Oyen W J & Corstens F H (2000) Radiolabeled receptor-binding peptides: a new class of radiopharmaceuticals. *Semin Nucl Med* 30:195-208.

Brenner S & Lerner R A (1992) Encoded combinatorial chemistry. *Proc Natl Acad Sci U S A* 89:5381-5383.

Brent R & Finley R L, Jr. (1997) Understanding Gene and Allele Function with Two-Hybrid Methods. *Annu Rev Genet* 31:663-704.

Bruchez M Jr, Moronne M, Gin P, Weiss S & Alivisatos A P (1998) Semiconductor nanocrystals as fluorescent biological labels. *Science* 281:2013-6.

Buchsbaum D, Khazaeli M B, Liu T, Bright S, Richardson K, Jones M & Meredith R (1995) Fractionated radioimmunotherapy of human colon carcinoma xenografts with 131I-labeled monoclonal antibody CC49. *Cancer Res* 55:5881s-5887s.

Burg M A, Pasqualini R, Arap W, Ruoslahti E & Stallcup W B (1999) NG2 proteoglycan-binding peptides target tumor neovasculature. *Cancer Res* 59:2869-2874.

Cai X & Garen A (1995) Anti-melanoma antibodies from melanoma patients immunized with genetically modified autologous tumor cells: selection of specific antibodies from single-chain Fv fusion phage libraries. *Proc Natl Acad Sci U S A* 92:6537-41.

Caprioli R M, Farmer T B & Gile J (1997) Molecular imaging of biological samples: localization of peptides and proteins using MALDI-TOF MS. *Anal Chem* 69:4751-60.

Carninci P, Kvam C, Kitamura A, Ohsumi T, Okazaki Y, Itoh M, Kamiya M, Shibata K, Sasaki N, Izawa M, Muramatsu M, Hayashizaki Y & Schneider C (1996) High-efficiency full-length cDNA cloning by biotinylated CAP trapper. *Genomics* 37:327-336.

Carpizo D & Iruela-Arispe M L (2000) Endogenous regulators of angiogenesis—emphasis on proteins with thrombospondin—type I motifs. *Cancer Metastasis Rev* 19:159-165.

Chan W C & Nie S (1998) Quantum dot bioconjugates for ultrasensitive nonisotopic detection. *Science* 281:2016-8.

Chang C N, Landolfi N F & Queen C (1991) Expression of antibody Fab domains on bacteriophage surfaces potential use for antibody selection. *J Immunol* 147:3610-14.

Chattopadhyay S, Das M K, Vanaja R & Ramamoorthy N (2001) Purification and stabilization of 99m Tc-d,l-HM-PAO: role of organic extractants. *Nucl Med Biol* 28:741-744.

Cheng P W (1996) Receptor Ligand-Facilitated Gene Transfer: Enhancement of Liposome-Mediated Gene Transfer and Expression by Transferrin. *Hum Gene Ther* 7:275-282.

Cheng S, Craig W S, Mullen D, Tschopp J F, Dixon D & Pierschbacher M D (1994) Design and synthesis of novel cyclic RGD-containing peptides as highly potent and selective integrin alpha IIb beta 3 antagonists. *J Med Chem* 37:1-8.

Chiu Y W, Chen R, Li Q X & Karu A E (2000) Derivation and Properties of Recombinant Fab Antibodies to Coplanar Polychlorinated Biphenyls. *J Agric Food Chem* 48:2614-2624.

Clapp C, Martial J A, Guzman R C, Rentier-Delure F & Weiner R I (1993) The 16-kilodalton N-terminal fragment of human prolactin is a potent inhibitor of angiogenesis. *Endocrinology* 133:1292-1299.

Coatney R W (2001) Ultrasound imaging: principles and applications in rodent research. *ILAR J* 42:233-247.

Cohen B A, Colas P & Brent R (1998) An Artificial Cell-Cycle Inhibitor Isolated from a Combinatorial Library. *Proc Natl Acad Sci U S A* 95:14272-14277.

Corringer P J, Weng J H, Ducos B, Durieux C, Boudeau P, Bohme A & Roques B P (1993) CCK-B agonist or antagonist activities of structurally hindered and peptidase-resistant Boc-CCK4 derivatives. *J Med Chem* 36:166-172.

Dameron K M, Volpert O V, Tainsky M A & Bouck N (1994) Control of angiogenesis in fibroblasts by p53 regulation of thrombospondin-1. *Science* 265:1582-1584.

Deutscher M P (1990) *Guide to Protein Purification*, Academic Press, San Diego, Calif., United States of America.

Dewanjee M K, Ghafouripour A K, Kapadvanjwala M, Dewanjee S, Serafini A N, Lopez D M & Sfakianakis G N (1994) Noninvasive imaging of c-myc oncogene messenger RNA with indium-111-antisense probes in a mammary tumor-bearing mouse model. *J Nucl Med* 35:1054-1063.

Dias S, Thomas H & Balkwill F (1998) Multiple Molecular and Cellular Changes Associated with Tumour Stasis and Regression During Il-12 Therapy of a Murine Breast Cancer Model. *Int J Cancer* 75:151-157.

Dillman R O, Johnson D E, Ogden J & Beidler D (1989) Significance of antigen, drug, and tumor cell targets in the preclinical evaluation of doxorubicin, daunorubicin, methotrexate, and mitomycin-C monoclonal antibody immunoconjugates. *Mol Biother* 1:250-255.

Donnelly E F, Geng L, Wojcicki W E, Fleischer A C & Hallahan D E (2001) Quantified power Doppler US of tumor blood flow correlates with microscopic quantification of tumor blood vessels. *Radiology* 219:166-170.

Dubertret B, Skourides P, Norris D J, Noireaux V, Brivanlou A H & Libchaber A (2002) In vivo imaging of quantum dots encapsulated in phospholipid micelles. *Science* 298:1759-62.

Eijan A M, Davel L, Oisgold-Daga S & de Lustig E S (1991) Modulation of tumor-induced angiogenesis by proteins of extracellular matrix. *Mol Biother* 3:38-40.

Ellerby H M, Arap W, Ellerby L M, Kain R, Andrusiak R, Rio G D, Krajewski S, Lombardo C R, Rao R, Ruoslahti E, Bredesen D E & Pasqualini R (1999) Anti-cancer activity of targeted pro-apoptotic peptides. *Nat Med* 5:1032-1038.

European Pat. No. 0 439 095

Evan G I, Lewis G K, Ramsay G & Bishop J M (1985) Isolation of monoclonal antibodies specific for human c-myc proto-oncogene product. *Mol Cell Biol* 5:3610-3616.

Fjalling M, Andersson P, Forssell-Aronsson E, Gretarsdottir J, Johansson V, Tisell L E, Wangberg B, Nilsson O, Berg G, Michanek A, Lindstedt G & Ahlman H (1996) Systemic radionuclide therapy using indium-111-DTPA-D-Phe1-octreotide in midgut carcinoid syndrome. *J Nucl Med* 37:1519-1521.

Fields G B & Noble R L (1990) Solid phase peptide synthesis utilizing 9-fluorenylmethoxycarbonyl amino acids. *Int J Pept Protein Res* 35:161-214.

Fields S & Song O (1989) A Novel Genetic System to Detect Protein-Protein Interactions. *Nature* 340:245-246.

Figini M, Obici L, Mezzanzanica D, Griffiths A, Colnaghi M I, Winter G & Canevari S (1998) Panning phage antibody libraries on cells: isolation of human Fab fragments against ovarian carcinoma using guided selection. *Cancer Res* 58:991-6.

Fitzpatrick J J & Garnett M C (1995) Design, synthesis and in vitro testing of methotrexate carrier conjugates linked via oligopeptide spacers. *Anticancer Drug Des* 10:1-9.

Fowlkes D M, Adams M D, Fowler V A & Kay B K (1992) Multipurpose Vectors for Peptide Expression on the M13 Viral Surface. *Biotechniques* 13:422-428.

Fraser S E (1996) Iontophoretic dye labeling of embryonic cells. *Methods Cell Biol* 51:147-160.

Fuller K J, Morse M A, White J H, Dowell S J & Sims M J (1998) Development of a Yeast Trihybrid Screen Using Stable Yeast Strains and Regulated Protein Expression. *Biotechniques* 25:85-88, 90-92.

Garbay-Jaureguiberry C, Ficheux D & Roques B P (1992) Solid phase synthesis of peptides containing the non-hydrolysable analog of (O)phosphotyrosine, p(CH2PO3H2)Phe. Application to the synthesis of 344-357 sequences of the beta 2 adrenergic receptor. *Int J Pept Protein Res* 39:523-527.

Garrard L J, Yang M, O'Connell M P, Kelley R F & Henner D J (1991) Fab assembly and enrichment in a monovalent phage display system. *Bio/technology* 9:1373-7.

Geng L, Donnelly E, McMahon G, Lin P C, Sierra-Rivera E, Oshinka H & Hallahan D E (2001) Inhibition of vascular endothelial growth factor receptor signaling leads to reversal of tumor resistance to radiotherapy. *Cancer Res* 61:2413-2419.

Glover D M & Hames B D (1995) *DNA Cloning: A Practical Approach*, 2nd ed. IRL Press at Oxford University Press, Oxford/New York.

Goldman C K, Rogers B E, Douglas J T, Sosnowski B A, Ying W, Siegal G P, Baird A, Campain J A & Curiel D T (1997) Targeted Gene Delivery to Kaposi's Sarcoma Cells Via the Fibroblast Growth Factor Receptor. *Cancer Res* 57:1447-1451.

Haaparanta T & Huse W D (1995) A Combinatorial Method for Constructing Libraries of Long Peptides Displayed by Filamentous Phage. *Mol Divers* 1:39-52.

Hallahan D E & Virudachalam S (1999) Accumulation of P-selectin in the lumen of irradiated blood vessels. *Radiat Res* 152:6-13.

Hallahan D, Clark E T, Kuchibhotla J, Gewertz B L & Collins T (1995b) E-Selectin Gene Induction by Ionizing Radiation Is Independent of Cytokine Induction. *Biochem Biophys Res Commun* 217:784-795.

Hallahan D E, Geng L, Cmelak A J, Chakravarthy A B, Martin W, Scarfone C & Gonzalez A (2001a) Targeting drug delivery to radiation-inducible neoantigens in tumor microvasculature. *J Control Release* 74:183-191.

Hallahan D E, Geng L & Shyr Y (2002) Effects of intercellular adhesion molecule 1 (ICAM-1) null mutation on radiation-induced pulmonary fibrosis and respiratory insufficiency in mice. *J Natl Cancer Inst* 94:733-41.

Hallahan D, Kuchibhotla J & Wyble C (1996) Cell adhesion molecules mediate radiation-inducible leukocyte adhesion to the vascular endothelium. *Cancer Res* 56:5150-5155.

Hallahan D E, Mauceri H J, Seung L P, Dunphy E J, Wayne J D, Hanna N N, Toledano A, Hellman S, Kufe D W & Weichselbaum R R (1995a) Spatial and temporal control of gene therapy using ionizing radiation. *Nat Med* 1:786-791.

Hallahan D E, Qu S, Geng L, Cmelak A, Chakravarthy A, Martin W, Scarfone C & Giorgio T (2001b) Radiation-Mediated Control of Drug Delivery. *Am J Clin Oncol* 24:473-80.

Hallahan D E, Staba-Hogan M J, Virudachalam S & Kolchinsky A (1998) X-Ray-Induced P-Selectin Localization to the Lumen of Tumor Blood Vessels. *Cancer Res* 58:5216-5220.

Hartmann F, Horak E M, Garmestani K, Wu C, Brechbiel M W, Kozak R W, Tso J, Kosteiny S A, Gansow O A, Nelson D L & et al., (1994) Radioimmunotherapy of nude mice bearing a human interleukin 2 receptor alpha-expressing lymphoma utilizing the alpha-emitting radionuclide-conjugated monoclonal antibody 212Bi-anti-Tac. *Cancer Res* 54:4362-4370.

Hawiger J & Timmons S (1992) Binding of fibrinogen and von Willebrand factor to platelet glycoprotein IIb-IIIa complex. *Methods Enzymol* 215:228-243.

Hawiger J, Kloczewiak M, Bednarek M A & Timmons S (1989) Platelet receptor recognition domains on the alpha chain of human fibrinogen: structure-function analysis. *Biochemistry* 28:2909-2914.

Healy J M, Murayama O, Maeda T, Yoshino K, Sekiguchi K & Kikuchi M (1995) Peptide ligands for integrin alpha v beta 3 selected from random phage display libraries. *Biochemistry* 34:3948-3955.

Henikoff J G, Pietrokovski S, McCallum C M & Henikoff S (2000) Blocks-Based Methods for Detecting Protein Homology. *Electrophoresis* 21:1700-1706.

Henikoff S & Henikoff J G (2000) Amino Acid Substitution Matrices. *Adv Protein Chem* 54:73-97.

Henikoff S & Henikoff J G (1992) Amino Acid Substitution Matrices from Protein Blocks. *Proc Natl Acad Sci U S A* 89:10915-10919.

Henn T F, Garnett M C, Chhabra S R, Bycroft B W & Baldwin R W (1993) Synthesis of 2'-deoxyuridine and 5-fluoro-2'-deoxyuridine derivatives and evaluation in antibody targeting studies. *J Med Chem* 36:1570-1579.

Heredia M, Santacana M & Valverde F (1991) A method using DiI to study the connectivity of cortical transplants. *J Neurosci Methods* 36:17-25.

Hnatowich D J, Mardirossian G, Fogarasi M, Sano T, Smith C L, Cantor C R, Rusckowski M & Winnard P, Jr. (1996) Comparative properties of a technetium-99m-labeled single-stranded natural DNA and a phosphorothioate derivative in vitro and in mice. *J Pharmacol Exp Ther* 276:326-334.

Holzem A, Nahring J M & Fischer R (2001) Rapid Identification of a Tobacco Mosaic Virus Epitope by Using a Coat Protein Gene-Fragment-Pviii Fusion Library. *J Gen Virol* 82:9-15.

Hoogenboom H R & Winter G (1992) By-passing immunisation. Human antibodies from synthetic repertoires of germline VH gene segments rearranged in vitro. *J Mol Biol* 227:381-8.

Hoogenboom H R, Griffiths A D, Johnson K S, Chiswell D J, Hudson P & Winter G (1991) Multi-subunit proteins on the surface of filamentous phage:methodologies for displaying antibody (Fab) and light chains. *Nucleic Acids Res* 19:4133-37.

Huang C C, Novak W R, Babbitt P C, Jewett A I, Ferrin T E & Klein T E (2000) Integrated Tools for Structural and Sequence Alignment and Analysis. *Pac Symp Biocomput*: 230-241.

Ingber D, Fujita T, Kishimoto S, Sudo K, Kanamaru T, Brem H & Folkman J (1990) Synthetic analogues of fumagillin that inhibit angiogenesis and suppress tumour growth. *Nature* 348:555-557.

Ishikawa E (1999) *Ultrasensitive and rapid enzyme immunoassay*. Elsevier, Amsterdam/New York.

Ito T, Qiu H, Collins J A, Brill A B, Johnson D K & Griffin T W (1991) Preclinical assessments of 90Y-labeled C110 anti-carcinoembryonic antigen immunotoxin: a therapeutic immunoconjugate for human colon cancer. *Cancer Res* 51:255-260.

Jones P T, Dear P H, Foote J, Neuberger M S & Winter G (1986) Replacing the complementarity-determining regions in a human antibody with those from a mouse. *Nature* 321:522-525.

Julien M, Kajiji S, Kaback R H & Gros P (2000) Simple purification of highly active biotinylated P-glycoprotein: enantiomer-specific modulation of drug-stimulated ATPase activity. *Biochemistry* 39:75-85.

Jung S & Pluckthun A (1997) Improving in Vivo Folding and Stability of a Single-Chain Fv Antibody Fragment by Loop Grafting. *Protein Eng* 10:959-966.

Kang A S, Barbas C F, Janda K D, Benkovic S J & Lerner R A (1991) Linkage of recognition and replication functions by assembling combinatorial antibody Fab libraries along phage surfaces. *Proc Natl Acad Sci U S A* 88:4363-4366.

Karlin S & Altschul S F (1993) Applications and Statistics for Multiple High-Scoring Segments in Molecular Sequences. *Proc Natl Acad Sci U S A* 90:5873-5877.

Kirk C J & Mule J J (2000) Gene-Modified Dendritic Cells for Use in Tumor Vaccines. *Hum Gene Ther* 11:797-806.

Kirpotin D, Park J W, Hong K, Zalipsky S, Li W L, Carter P, Benz C C & Papahadjopoulos D (1997) Sterically Stabilized Anti-Her2 Immunoliposomes: Design and Targeting to Human Breast Cancer Cells in Vitro. *Biochemistry* 36:66-75.

Koivunen E, Gay D A & Ruoslahti E (1993) Selection of peptides binding to the alpha 5 beta 1 integrin from phage display library. *J Biol Chem* 268:20205-20210.

Koivunen E, Wang B & Ruoslahti E (1994) Isolation of a highly specific ligand for the alpha 5 beta 1 integrin from a phage display library. *J Cell Biol* 124:373-380.

Kolonin M G & Finley R L, Jr. (1998) Targeting Cyclin-Dependent Kinases in Drosophila with Peptide Aptamers. *Proc Natl Acad Sci U S A* 95:14266-14271.

Koning G A, Morselt H W, Velinova M J, Donga J, Gorter A, Allen T M, Zalipsky S, Kamps J A & Scherphof G L (1999) Selective Transfer of a Lipophilic Prodrug of 5-Fluorodeoxyuridine from Immunoliposomes to Colon Cancer Cells. *Biochim Biophys Acta* 1420:153-167.

Kosfeld M D & Frazier W A (1993) Identification of a new cell adhesion motif in two homologous peptides from the COOH-terminal cell binding domain of human thrombospondin. *J Biol Chem* 268:8808-8814.

Krauer K G, McKenzie I F & Pietersz G A (1992) Antitumor effect of 2'-deoxy-5-fluorouridine conjugates against a murine thymoma and colon carcinoma xenografts. *Cancer Res* 52:132-137.

Krenning E P & de Jong M (2000) Therapeutic use of radiolabelled peptides. *Ann Oncol* 11:267-271.

Kwekkeboom D, Krenning E P & de Jong M (2000) Peptide receptor imaging and therapy. *J Nucl Med* 41:1704-1713.

Kyte J & Doolittle R F (1982) A simple method for displaying the hydropathic character of a protein. *J Mol Biol* 157:105-132.

Lau A, Berube G & Ford C H (1995) Conjugation of doxorubicin to monoclonal anti-carcinoembryonic antigen antibody via novel thiol-directed cross-linking reagents. *Bioorg Med Chem* 3:1299-1304.

Law B (1996) *Immunoassay: A Practical Guide*. Taylor & Francis, London/Bristol, PA.

Lecrenier N, Foury F & Goffeau A (1998) Two-Hybrid Systematic Screening of the Yeast Proteome. *Bioessays* 20:1-5.

Lees W (2001) Ultrasound imaging in three and four dimensions. *Semin Ultrasound CT MR* 22:85-105.

Leibel S A & Phillips T L (1998) Textbook of Radiation Oncology. Saunders, Philadelphia, Pa., United States of America.

Licha K, Riefke B, Ntziachristos V, Becker A, Chance B & Semmler W (2000) Hydrophilic cyanine dyes as contrast agents for near-infrared tumor imaging: synthesis, photophysical properties and spectroscopic in vivo characterization. *Photochem Photobiol* 72:392-398.

Lu Z, Murray K S, Van Cleave V, LaVallie E R, Stahl M L & McCoy J M (1995) Expression of thioredoxin random peptide libraries on the *Escherichia coli* cell surface as functional fusions to flagellin: a system designed for exploring protein-protein interactions. *Biotechnology (NY)* 13:366-372.

Mackensen A, Lindemann A & Mertelsmann R (1997) Immunostimulatory Cytokines in Somatic Cells and Gene Therapy of Cancer. *Cytokine Growth Factor Rev* 8:119-128.

Maione T E, Gray G S, Petro J, Hunt A J, Donner A L, Bauer S I, Carson H F & Sharpe R J (1990) Inhibition of angiogenesis by recombinant human platelet factor-4 and related peptides. *Science* 247:77-79.

Manome Y, Abe M, Hagen M F, Fine H A & Kufe D W (1994) Enhancer sequences of the DF3 gene regulate expression of the herpes simplex virus thymidine kinase gene and confer sensitivity of human breast cancer cells to ganciclovir. *Cancer Res* 54:5408-5413.

Manson M M (1992) *Immunochemical Protocols*. Humana Press, Totowa, N.J., United States of America.

Martodam R R, Twumasi D Y, Liener I E, Powers J C, Nishino N & Krejcarek G (1979) Albumin microspheres as carrier of an inhibitor of leukocyte elastase: potential therapeutic agent for emphysema. *Proc Natl Acad Sci U S A* 76:2128-2132.

McCafferty J, Griffiths A D, Winter G & Chiswell D J (1990) Phage antibodies: filamentous phage displaying antibody variable domains. *Nature* 348:552-4.

McOmie J F W. (1973) Protective Groups in Organic Chemistry, Plenum Press, London/New York.

Merrifield R B (1969) Solid-phase peptide synthesis. *Adv Enzymol Relat Areas Mol Biol* 32:221-296.

Mocikat R, Kutemeier G, Hoffmann-Fezer G & Thierfelder S (1994) A mouse model for the preclinical evaluation of immunosuppressive effector functions of human isotypes. The human IgG1 isotype is superior to IgG3. *Transplantation* 57:405-11.

Nabel G (1997) Vectors for Gene Therapy. In: *Current Protocols in Human Genetics*, John Wiley & Sons, New York, N.Y., United States of America.

Nam S M, Kim H S, Ahn W S & Park Y S (1999) Sterically Stabilized Anti-G(M3), Anti-Le(X) Immunoliposomes: Targeting to B16bl6, Hrt-18 Cancer Cells. *Oncol Res* 11:9-16.

Narvaiza I, Mazzolini G, Barajas M, Duarte M, Zaratiegui M, Qian C, Melero I & Prieto J (2000) Intratumoral Coinjection of Two Adenoviruses, One Encoding the Chemokine IFN-Gamma-lnducible Protein-10 and Another Encoding Il-12, Results in Marked Antitumoral Synergy. *J Immunol* 164:3112-3122.

Needleman S B & Wunsch C D (1970) A General Method Applicable to the Search for Similarities in the Amino Acid Sequence of Two Proteins. *J Mol Biol* 48:443-453.

Neri D, Carnemolla B, Nissim A, Leprini A, Querze G, Balza E, Pini A, Tarli L, Halin C, Neri P, Zardi L & Winter G (1997) Targeting by Affinity-Matured Recombinant Antibody Fragments of an Angiogenesis Associated Fibronectin Isoform. *Nat Biotechnol* 15:1271-1275.

Nomura T & Hasegawa H (2000) Chemokines and anticancer immunotherapy: anti-tumor effect of EBI1-ligand chemokine (ELC) and secondary lymphoid tissue chemokine (SLC). *Anticancer Res* 20:4073-4080.

O'Byrne K J, Dalgleish A G, Browning M J, Steward W P & Harris A L (2000) The relationship between angiogenesis and the immune response in carcinogenesis and the progression of malignant disease. *Eur J Cancer* 36:151-169.

O'Reilly M S, Boehm T, Shing Y, Fukai N, Vasios G, Lane W S, Flynn E, Birkhead J R, Olsen B R & Folkman J (1997) Endostatin: an endogenous inhibitor of angiogenesis and tumor growth. *Cell* 88:277-285.

O'Reilly M S, Holmgren L, Shing Y, Chen C, Rosenthal R A, Moses M, Lane W S, Cao Y, Sage E H & Folkman J (1994) Angiostatin: a novel angiogenesis inhibitor that mediates the suppression of metastases by a Lewis lung carcinoma. *Cell* 79:315-328.

Ohtsuka E, Matsuki S, Ikehara M, Takahashi Y & Matsubara K (1985) An alternative approach to deoxyoligonucleotides as hybridization probes by insertion of deoxyinosine at ambiguous codon positions. *J Biol Chem* 260:2605-2608.

Park J W, Hong K, Kirpotin D B, Papahadjopoulos D & Benz C C (1997) Immunoliposomes for Cancer Treatment. *Adv Pharmacol* 40:399-435.

Pasqualini R & Ruoslahti E (1996) Organ targeting in vivo using phage display peptide libraries. *Nature* 380:364-366.

Pasqualini R, Koivunen E & Ruoslahti E (1997) Alpha V Integrins as Receptors for Tumor Targeting by Circulating Ligands. *Nat Biotechnol* 15:542-546.

Pavone V, Di Blasio B, Lombardi A, Maglio O, Isernia C, Pedone C, Benedetti E, Altmann E & Mutter M (1993) Non coded C alpha, alpha-disubstituted amino acids. X-ray diffraction analysis of a dipeptide containing (S)-alpha-methylserine. *Int J Pept Protein Res* 41:15-20.

Pearson W R & Lipman D J (1988) Improved Tools for Biological Sequence Comparison. *Proc Natl Acad Sci U S A* 85:2444-2448.

Peter K, Graeber J, Kipriyanov S, Zewe-Welschof M, Runge M S, Kubler W, Little M & Bode C (2000) Construction and Functional Evaluation of a Single-Chain Antibody Fusion Protein with Fibrin Targeting and Thrombin Inhibition after Activation by Factor Xa. *Circulation* 101:1158-1164.

Pierschbacher M D & Ruoslahti E (1987) Influence of stereochemistry of the sequence Arg-Gly-Asp-Xaa on binding specificity in cell adhesion. *J Biol Chem* 262:17294-17298.

Pluckthun A (1994) in *The Pharmacology of Monoclonal Antibodies*, vol. 113, pp. 269-315, Rosenburg & Moore (eds.), Springer-Verlag, New York, United States of America.

Pomper M G & Port J D (2000) New techniques in MR imaging of brain tumors. *Magn Reson Imaging Clin N Am* 8:691-713.

Presta L G (1992) Antibody engineering. *Curr Op Struct Biol* 2:593-596.

Ragnarson B, Bengtsson L & Haegerstrand A (1992) Labeling with fluorescent carbocyanine dyes of cultured endothelial and smooth muscle cells by growth in dye-containing medium. *Histochemistry* 97:329-333.

Rehrauer W M, Lavery P E, Palmer E L, Singh R N & Kowalczykowski S C (1996) Interaction of *Escherichia Coli* RecA Protein with LexA Repressor. I. LexA Repressor Cleavage Is Competitive with Binding of a Secondary DNA Molecule. *J Biol Chem* 271:23865-23873.

Rehrauer W M, Lavery P E, Palmer E L, Singh R N & Kowatczykowski S C (1996) Interaction of *Escherichia coli* RecA protein with LexA repressor. I. LexA repressor cleavage is competitive with binding of a secondary DNA molecule. *J Biol Chem* 271:23865-23873.

Reichmann L, Clark M, Waldmann H & Winter G (1988) Reshaping human antibodies for therapy. *Nature* 332:323-329.

Rossolini G M, Cresti S, Ingianni A, Cattani P, Riccio M L & Satta G (1994) Use of deoxyinosine-containing primers vs degenerate primers for polymerase chain reaction based on ambiguous sequence information. *Mol Cell Probes* 8:91-98.

Rovaris M, Comi G & Filippi M (2001) The role of non-conventional MR techniques to study multiple sclerosis patients. *J Neurol Sci* 186 Suppl 1:S3-9.

Rowland A J, Pietersz G A & McKenzie I F (1993) Preclinical investigation of the antitumour effects of anti-CD19-idarubicin immunoconjugates. *Cancer Immunol Immunother* 37:195-202.

Sagiuchi T, Ishii K, Asano Y, Aoki Y, Woodhams R, Yanaihara H, Kan S & Hayakawa K (2001) Transient seizure activity demonstrated by Tc-99m HMPAO SPECT and diffusion-weighted MR imaging. *Ann Nucl Med* 15:267-270.

Sakamoto N, Iwahana M, Tanaka N G & Osada Y (1991) Inhibition of angiogenesis and tumor growth by a synthetic laminin peptide, CDPGYIGSR-NH2. *Cancer Res* 51:903-906.

Saltzman W M & Fung L K (1997) Polymeric implants for cancer chemotherapy. *Adv Drug Deliv Rev* 26:209-230.

Sambrook J & Russell D (2001) *Molecular Cloning: A Laboratory Manual*, 3rd ed. Cold Spring Harbor Laboratory Press, Cold Spring Harbor, N.Y., United States of America.

Saqi M A, Wild D L & Hartshorn M J (1999) Protein Analyst—a Distributed Object Environment for Protein Sequence and Structure Analysis. *Bioinformatics* 15:521-522.

Schechter B, Arnon R, Wilchek M, Schlessinger J, Hurwitz E, Aboud-Pirak E & Sela M (1991) Indirect immunotargeting of cis-Pt to human epidermoid carcinoma KB using the avidin-biotin system. *Int J Cancer* 48:167-172.

Schneider C H & Eberle A N (1993) *Peptides, 1992: Proceedings of the Twenty-Second European Peptide Symposium*, Sep. 13-19, 1992, Interlaken, Switzerland. Escom, Leiden.

Schröder E & Lübke K (1965) *The Peptides*. Academic Press, New York, United States of America.

Schueneman A J, Himmelfarb E, Geng L, Tan J, Donnelly E, Mendel D, McMahon G & Hallahan D E (2003) SU11248 maintenance therapy prevents tumor regrowth after fractionated irradiation of murine tumor models. *Cancer Res* 63:4009-16.

Schwendener R (1992) Liposomes and Immunoliposomes as Carriers for Cytostatic Drugs, Magnetic Resonance Contrast Agents, and Fluorescent Chelates. *Chimia* 46:69-77.

Shalaby M R, Shepard H M, Presta L, Rodrigues M L, Beverley P C, Feldmann M & Carter P (1992) Development of humanized bispecific antibodies reactive with cytotoxic lymphocytes and tumor cells overexpressing the HER2 protooncogene. *J Exp Med* 175:217-25.

Shawler D L, Johnson D E, Sweet M D, Myers L J, Tudor S D, Beidler D E, Koziol J A & Dillman R O (1988) Preclinical trials using an immunoconjugate of T101 and methotrexate in an athymic mouse/human T-cell tumor model. *J Biol Response Mod* 7:608-618.

Shen T, Weissleder R, Papisov M, Bogdanov A, Jr. & Brady T J (1993) Monocrystalline iron oxide nanocompounds (MION): physicochemical properties. *Magn Reson Med* 29:599-604.

Shih L B, Goldenberg D M, Xuan H, Lu H W, Mattes M J & Hall T C (1994) Internalization of an intact doxorubicin immunoconjugate. *Cancer Immunol Immunother* 38:92-98.

Silhavy T J, Berman M L, Enquist L W & Cold Spring Harbor Laboratory. (1984) *Experiments with Gene Fusions*. Cold Spring Harbor Laboratory, Cold Spring Harbor, N.Y., United States of America.

Sivam G P, Martin P J, Reisfeld R A & Mueller B M (1995) Therapeutic efficacy of a doxorubicin immunoconjugate in a preclinical model of spontaneous metastatic human melanoma. *Cancer Res* 55:2352-2356.

Smith G P (1985) Filamentous fusion phage: novel expression vectors that display cloned antigens on the virion surface. *Science* 228:1315-1317.

Smith T F & Waterman M (1981) Comparison of Biosequences. *Adv Appl Math* 2:482-489.

Smyth M J, Pietersz G A & McKenzie I F (1987) The cellular uptake and cytotoxicity of chlorambucil-monoclonal antibody conjugates. *Immunol Cell Biol* 65:315-321.

Staba M J, Wickham T J, Kovesdi I & Hallahan D E (2000) Modifications of the fiber in adenovirus vectors increase tropism for malignant glioma models. *Cancer Gene Ther* 7:13-19.

Stadel J M, Wilson S & Bergsma D J (1997) Orphan G protein-coupled receptors: a neglected opportunity for pioneer drug discovery. *Trends Pharmacol Sci* 18:430-7.

Starling J J, Maciak R S, Hinson N A, Nichols C L, Briggs S L, Laguzza B C, Smith W & Corvalan J R (1992) In vivo antitumor activity of a panel of four monoclonal antibody-vinca alkaloid immunoconjugates which bind to three distinct epitopes of carcinoembryonic antigen. *Bioconjug Chem* 3:315-322.

Stewart J M & Young J D (1969) Solid Phase Peptide Synthesis, Freeman, San Francisco.

Stoeckli M, Chaurand P, Hallahan D E & Caprioli R M (2001) Imaging mass spectrometry: a new technology for the analysis of protein expression in mammalian tissues. *Nat Med* 7:493-6.

Tang X B & Casey J R (1999) Trapping of inhibitor-induced conformational changes in the erythrocyte membrane anion exchanger AE1. *Biochemistry* 38:14565-14572.

Tavitian B, Terrazzino S, Kuhnast B, Marzabal S, Stettler O, Dolle F, Deverre J R, Jobert A, Hinnen F, Bendriem B, Crouzel C & Di Giamberardino L (1998) In vivo imaging of oligonucleotides with positron emission tomography. *Nat Med* 4:467-471.

Tijssen P (1993) Laboratory Techniques in Biochemistry and Molecular Biology-Hybridization with Nucleic Acid Probes. Elsevier, New York, United States of America.

Tolsma S S, Volpert O V, Good D J, Frazier W A, Polverini P J & Bouck N (1993) Peptides derived from two separate domains of the matrix protein thrombospondin-1 have anti-angiogenic activity. *J Cell Biol* 122:497-511.

Tung CH, Zhu T, Lackland H & Stein S (1992) An acridine amino acid derivative for use in Fmoc peptide synthesis. *Pept Res* 5:115-118.

Urge L, Otvos L, Jr., Lang E, Wroblewski K, Laczko I & Hollosi M (1992) Fmoc-protected, glycosylated asparagines potentially useful as reagents in the solid-phase synthesis of N-glycopeptides. *Carbohydr Res* 235:83-93

U.S. Pat. No. 4,235,871
U.S. Pat. No. 4,244,946
U.S. Pat. No. 4,551,482
U.S. Pat. No. 4,554,101
U.S. Pat. No. 5,011,634

U.S. Pat. No. 5,088,499
U.S. Pat. No. 5,147,631
U.S. Pat. No. 5,168,037
U.S. Pat. No. 5,223,409
U.S. Pat. No. 5,234,933
U.S. Pat. No. 5,264,563
U.S. Pat. No. 5,326,902
U.S. Pat. No. 5,490,840
U.S. Pat. No. 5,498,538
U.S. Pat. No. 5,508,020
U.S. Pat. No. 5,510,103
U.S. Pat. No. 5,645,815
U.S. Pat. No. 5,578,629
U.S. Pat. No. 5,574,172
U.S. Pat. No. 5,650,489
U.S. Pat. No. 5,651,991
U.S. Pat. No. 5,667,988
U.S. Pat. No. 5,688,931
U.S. Pat. No. 5,702,892
U.S. Pat. No. 5,707,605
U.S. Pat. No. 5,714,166
U.S. Pat. No. 5,738,837
U.S. Pat. No. 5,738,996
U.S. Pat. No. 5,747,334
U.S. Pat. No. 5,756,291
U.S. Pat. No. 5,780,225
U.S. Pat. No. 5,786,387
U.S. Pat. No. 5,811,392
U.S. Pat. No. 5,811,512
U.S. Pat. No. 5,811,515
U.S. Pat. No. 5,817,757
U.S. Pat. No. 5,817,879
U.S. Pat. No. 5,824,483
U.S. Pat. No. 5,830,856
U.S. Pat. No. 5,837,500
U.S. Pat. No. 5,840,479
U.S. Pat. No. 5,580,717
U.S. Pat. No. 5,851,818
U.S. Pat. No. 5,855,900
U.S. Pat. No. 5,858,410
U.S. Pat. No. 5,858,670
U.S. Pat. No. 5,858,784
U.S. Pat. No. 5,865,754
U.S. Pat. No. 5,922,356
U.S. Pat. No. 5,939,598
U.S. Pat. No. 5,948,635
U.S. Pat. No. 5,922,545
U.S. Pat. No. 5,928,627
U.S. Pat. No. 5,948,767
U.S. Pat. No. 5,994,392
U.S. Pat. No. 6,013,638
U.S. Pat. No. 6,015,561
U.S. Pat. No. 6,015,881
U.S. Pat. No. 6,022,737
U.S. Pat. No. 6,024,938
U.S. Pat. No. 6,031,071
U.S. Pat. No. 6,083,486
U.S. Pat. No. 6,056,938
U.S. Pat. No. 6,057,098
U.S. Pat. No. 6,068,829
U.S. Pat. No. 6,071,890
U.S. Pat. No. 6,080,384
U.S. Pat. No. 6,106,866
U.S. Pat. No. 6,107,059
U.S. Pat. No. 6,132,766
U.S. Pat. No. 6,136,295
U.S. Pat. No. 6,156,511

U.S. Pat. No. 6,159,443
U.S. Pat. No. 6,168,912
U.S. Pat. No. 6,174,708
U.S. Pat. No. 6,180,348
U.S. Pat. No. 6,197,333
U.S. Pat. No. 6,200,598
U.S. Pat. No. 6,210,707
U.S. Pat. No. 6,214,553
U.S. Pat. No. 6,217,886
U.S. Pat. No. 6,221,018
U.S. Pat. No. 6,225,447
U.S. Pat. No. 6,231,834
U.S. Pat. No. 6,245,318
U.S. Pat. No. 6,246,901
U.S. Pat. No. 6,254,852

Van Ewijk W, de Kruif J, Germeraad W T, Berendes P, Ropke C, Platenburg P P & Logtenberg T (1997) Subtractive isolation of phage-displayed single-chain antibodies to thymic stromal cells by using intact thymic fragments. *Proc Natl Acad Sci USA* 94:3903-3908

Vasavada H A, Ganguly S, Germino F J, Wang Z X & Weissman S M (1991) A Contingent Replication Assay for the Detection of Protein-Protein Interactions in Animal Cells. *Proc Natl Acad Sci U S A* 88:10686-10690.

Vinogradov S A, Lo L W, Jenkins W T, Evans S M, Koch C & Wilson D F (1996) Noninvasive imaging of the distribution in oxygen in tissue in vivo using near-infrared phosphors. *Biophys J* 70:1609-1617.

Virgolini I, Traub T, Novotny C, Leimer M, Fuger B, Li S R, Patri P, Pangerl T, Angelberger P, Raderer M, Andreae F, Kurtaran A & Dudczak R (2001) New trends in peptide receptor radioligands. *Q J Nucl Med* 45:153-159.

Voest E E, Kenyon B M, O'Reilly M S, Truitt G, D'Amato R J & Folkman J (1995) Inhibition of angiogenesis in vivo by interleukin 12. *J Natl Cancer Inst* 87:581-586.

Walther W & Stein U (1999) Therapeutic Genes for Cancer Gene Therapy. *Mol Biotechnol* 13:21-28.

Weissleder R, Bogdanov A & Papisov M (1992) Drug targeting in magnetic resonance imaging. *Magn Reson Q* 8:55-63.

Weissleder R, Tung C H, Mahmood U & Bogdanov A, Jr. (1999) In vivo imaging of tumors with protease-activated near-infrared fluorescent probes. *Nat Biotechnol* 17:375-378.

Wickham T J, Carrion M E & Kovesdi I (1995) Targeting of adenovirus penton base to new receptors through replacement of its RGD motif with other receptor-specific peptide motifs. *Gene Ther* 2:750-756.

Wilbur D S (1992) Radiohalogenation of proteins: an overview of radionuclides, labeling methods, and reagents for conjugate labeling. *Bioconjug Chem* 3:433-470

PCT International Pat. Publication WO 01/09611
PCT International Pat. Publication WO 93/25521
PCT International Pat. Publication WO 98/10795
PCT International Pat. Publication WO 99/54728

Woltering E A, Barrie R, O'Dorisio T M, Arce D, Ure T, Cramer A, Holmes D, Robertson J & Fassler J (1991) Somatostatin analogues inhibit angiogenesis in the chick chorioallantoic membrane. *J Surg Res* 50:245-251.

Yang M, Wu Z & Fields S (1995) Protein-Peptide Interactions Analyzed with the Yeast Two-Hybrid System. *Nucleic Acids Res* 23:1152-1156.

Yokota T, Milenic D, Whitlow M & Schlom J (1992) Rapid Tumor Penetration of a Single-Chain Fv and Comparison with Other Immunoglobulin Forms. *Cancer Res* 52:3402-3408.

Yoo T M, Chang H K, Choi C W, Webber K O, Le N, Kim I S, Eckelman W C, Pastan I, Carrasquillo J A & Paik C H (1997) Technetium-99m labeling and biodistribution of anti-TAC disulfide-stabilized Fv fragment. *J Nucl Med* 38:294-300.

It will be understood that various details of the presently disclosed subject matter can be changed without departing from the scope of the presently disclosed subject matter. Furthermore, the foregoing description is for the purpose of illustration only, and not for the purpose of limitation—the presently disclosed subject matter being defined by the claims appended hereto.

What is claimed is:

1. A method for screening a plurality of phage-displayed antibodies for an ability to bind to a radiation-inducible neoantigen present on a cell, the method comprising:
   (a) contacting the cell with a first solution, the first solution comprising the plurality of phage-displayed antibodies;
   (b) isolating a second solution, the second solution comprising those phage-displayed antibodies that do not bind to the cell;
   (c) removing any phage-displayed antibodies bound to the cell;
   (d) treating the cell with radiation, wherein the treating results in a radiation-inducible neoantigen being present on the cell;
   (e) contacting the cell with the second solution; and
   (f) detecting binding of a phage-displayed antibody to the radiation-inducible neoantigen on the cell.

2. The method of claim 1, wherein the plurality of phage-displayed antibodies comprise a phage-displayed single chain variable fragment (scFv) library or a phage-displayed Fab library.

3. The method of claim 1, wherein the phage-displayed antibodies are humanized.

4. The method of claim 1, wherein the phage-displayed antibody is encoded by a nucleic acid encoding a single chain variable fragment (scFv) antibody having an amino acid sequence selected from the group consisting of SEQ ID NOs: 18, 20, 22, and 24, or by a nucleic acid sequence that is selected from the group consisting of SEQ ID NOs: 17, 19, 21, and 23.

5. The method of claim 1, wherein the phage-displayed antibody has an amino acid sequence that is selected from the group consisting of SEQ ID NOs: 18, 20, 22, and 24.

6. The method of claim 1, wherein the phage-displayed antibody further comprises an epitope tag.

7. The method of claim 6, wherein the epitope tag is selected from the group consisting of a c-myc tag and a histidine tag.

8. The method of claim 1, wherein the cell is selected from the group consisting of a tumor cell and a vascular endothelial cell.

9. The method of claim 8, wherein the vascular endothelial cell is present within tumor microvasculature.

10. The method of claim 1, wherein the radiation-inducible neoantigen is selected from the group consisting of P-selectin, E-selectin, Endoglin, $\alpha_{2b}\beta_3$ integrin, and $\alpha_v\beta_3$ integrin.

11. The method of claim 1, wherein the detecting is by a technique selected from the group consisting of ELISA, BIACORE, Western blotting, immunohistochemistry, fluorometric microvolume assay technology, mass spectroscopy, MALDI-MS, and MALDI-TOF.

12. A method for prioritizing the binding of a plurality of antibodies or antibody fragments to a target tissue in a subject, the method comprising:
   (a) providing a plurality of antibodies or antibody fragments that bind to the target, wherein the plurality of antibodies or antibody fragments comprise at least two different antibodies or antibody fragments that bind a radiation-inducible neoantigen within the target tissue, and wherein the at least two different antibodies or antibody fragments are distinguishable from each other;
   (b) irradiating the target tissue, whereby the radiation-inducible neoantigens are expressed within the target tissue;
   (c) administering the plurality of antibodies or antibody fragments to the subject under conditions sufficient to allow the plurality of antibodies or antibody fragments to bind to the radiation-inducible neoantigen in the target tissue;
   (d) isolating a portion of the target tissue from the subject, wherein the portion comprises the radiation-inducible neoantigens to which the plurality of antibodies or antibody fragments bind;
   (e) identifying the at least two different antibodies or antibody fragments in the portion of the target tissue;
   (f) comparing a relative selectivity and an affinity for the radiation-inducible neoantigens of the at least two different antibodies or antibody fragments identified in step (e) in the irradiated target tissue; and
   (g) assigning a priority to the at least two different antibodies or antibody fragments based on the comparing of step (f).

13. The method of claim 12, wherein the subject is a mammal.

14. The method of claim 12, wherein the target tissue is a tumor or tumor vasculature.

15. The method of claim 12, wherein the antibodies or antibody fragments are single chain fragment variable (scFv) antibodies, Fab antibodies, or combinations thereof.

16. The method of claim 15, wherein the antibodies or antibody fragments are humanized.

17. The method of claim 12, wherein the at least two different antibodies or antibody fragments that bind to at least two different radiation-inducible neoantigens are distinguishable from each other based upon differences in molecular weight.

18. The method of claim 12, wherein the at least two different antibodies or antibody fragments that bind to at least two different radiation-inducible neoantigens within the target tissue each further comprises a different detectable label, such that the antibodies or antibody fragments that bind to different radiation-inducible neoantigens can be distinguished from each other.

19. The method of claim 18, wherein the different detectable labels are fluorescent labels, and each fluorescent label has a different excitation or emission spectrum, such that the different antibodies can be distinguished from each other.

20. The method of claim 12, wherein the at least two radiation-inducible neoantigens within the target tissue are selected from the group consisting of P-selectin, E-selectin, Endoglin, $\alpha_{2b}\beta_3$ integrin, and $\alpha_v\beta_3$ integrin.

21. The method of claim 12, wherein the administering is by intravenous injection or intratumoral injection.

22. The method of claim 12, wherein the portion is a tumor biopsy.

23. The method of claim 12, wherein the detecting is by mass spectroscopy.

24. The method of claim 13, wherein the antibody or antibody fragment is a single chain fragment variable (scFv) antibody or an Fab antibody.

* * * * *

```
                        SEQUENCE LISTING

<160> NUMBER OF SEQ ID NOS: 34

<210> SEQ ID NO 1
<211> LENGTH: 8
<212> TYPE: PRT
<213> ORGANISM: Artificial
<220> FEATURE:
<223> OTHER INFORMATION: Artifical peptide ligand number 1

<400> SEQUENCE: 1

Asn His Val Gly Gly Ser Ser Val
1               5

<210> SEQ ID NO 2
<211> LENGTH: 10
<212> TYPE: PRT
<213> ORGANISM: Artificial
<220> FEATURE:
<223> OTHER INFORMATION: Artificial peptide ligand number 2

<400> SEQUENCE: 2

Asn Ser Leu Arg Gly Asp Gly Ser Ser Val
1               5                   10

<210> SEQ ID NO 3
<211> LENGTH: 10
<212> TYPE: PRT
<213> ORGANISM: Artificial
<220> FEATURE:
<223> OTHER INFORMATION: Artificial peptide ligand number 3

<400> SEQUENCE: 3

Asn Ser Val Arg Gly Ser Gly Ser Gly Val
1               5                   10

<210> SEQ ID NO 4
<211> LENGTH: 7
<212> TYPE: PRT
<213> ORGANISM: Artificial
<220> FEATURE:
<223> OTHER INFORMATION: Artificial peptide ligand number 4

<400> SEQUENCE: 4

Asn Ser Val Gly Ser Arg Val
1               5

<210> SEQ ID NO 5
<211> LENGTH: 9
<212> TYPE: PRT
<213> ORGANISM: Artificial
<220> FEATURE:
<223> OTHER INFORMATION: Artificial peptide ligand number 5

<400> SEQUENCE: 5

Ser Leu Arg Gly Asp Gly Ser Ser Val
1               5
```

<210> SEQ ID NO 6
<211> LENGTH: 7
<212> TYPE: PRT
<213> ORGANISM: Artificial
<220> FEATURE:
<223> OTHER INFORMATION: Artificial peptide ligand number 6

<400> SEQUENCE: 6

Arg Gly Asp Gly Ser Ser Val
1               5

<210> SEQ ID NO 7
<211> LENGTH: 4
<212> TYPE: PRT
<213> ORGANISM: Artificial
<220> FEATURE:
<223> OTHER INFORMATION: Artificial peptide ligand number 7

<400> SEQUENCE: 7

Gly Ser Arg Val
1

<210> SEQ ID NO 8
<211> LENGTH: 4
<212> TYPE: PRT
<213> ORGANISM: Artificial
<220> FEATURE:
<223> OTHER INFORMATION: Artificial peptide ligand number 8
<220> FEATURE:
<221> NAME/KEY: MISC_FEATURE
<222> LOCATION: (1)..(4)
<223> OTHER INFORMATION: X is any amino acid

<400> SEQUENCE: 8

Gly Ser Xaa Val
1

<210> SEQ ID NO 9
<211> LENGTH: 8
<212> TYPE: PRT
<213> ORGANISM: Artificial
<220> FEATURE:
<223> OTHER INFORMATION: Artificial peptide ligand number 9
<220> FEATURE:
<221> NAME/KEY: MISC_FEATURE
<222> LOCATION: (1)..(8)
<223> OTHER INFORMATION: X is any amino acid

<400> SEQUENCE: 9

Asn Ser Xaa Arg Gly Xaa Gly Ser
1               5

<210> SEQ ID NO 10
<211> LENGTH: 3
<212> TYPE: PRT
<213> ORGANISM: Artificial
<220> FEATURE:
<223> OTHER INFORMATION: Artificial peptide ligand number 10

<400> SEQUENCE: 10

Asn Ser Val
1

<210> SEQ ID NO 11
<211> LENGTH: 4
<212> TYPE: PRT
<213> ORGANISM: Artificial
<220> FEATURE:

-continued

```
<223> OTHER INFORMATION: Artificial peptide ligand number 11
<220> FEATURE:
<221> NAME/KEY: MISC_FEATURE
<222> LOCATION: (1)..(4)
<223> OTHER INFORMATION: X is any amino acid

<400> SEQUENCE: 11

Asn Ser Xaa Arg
1

<210> SEQ ID NO 12
<211> LENGTH: 4
<212> TYPE: PRT
<213> ORGANISM: Artificial
<220> FEATURE:
<223> OTHER INFORMATION: Artificial peptide ligand number 12
<220> FEATURE:
<221> NAME/KEY: MISC_FEATURE
<222> LOCATION: (1)..(4)
<223> OTHER INFORMATION: X is any amino acid

<400> SEQUENCE: 12

Asn Xaa Val Gly
1

<210> SEQ ID NO 13
<211> LENGTH: 4
<212> TYPE: PRT
<213> ORGANISM: Artificial
<220> FEATURE:
<223> OTHER INFORMATION: Artificial peptide ligand number 13

<400> SEQUENCE: 13

Gly Ser Ser Val
1

<210> SEQ ID NO 14
<211> LENGTH: 20
<212> TYPE: DNA
<213> ORGANISM: T7 bacteriophage

<400> SEQUENCE: 14
agcggaccag attatcgcta                                              20

<210> SEQ ID NO 15
<211> LENGTH: 19
<212> TYPE: DNA
<213> ORGANISM: T7 bacteriophage

<400> SEQUENCE: 15
aaccctcaag acccgttta                                               19

<210> SEQ ID NO 16
<211> LENGTH: 12
<212> TYPE: PRT
<213> ORGANISM: Artificial
<220> FEATURE:
<223> OTHER INFORMATION: Artificial peptide ligand number 16

<400> SEQUENCE: 16

His His Leu Gly Gly Ala Lys Gln Ala Gly Asp Val
1               5                   10

<210> SEQ ID NO 17
<211> LENGTH: 726
<212> TYPE: DNA
<213> ORGANISM: Artificial
```

```
<220> FEATURE:
<223> OTHER INFORMATION: Artificial antibody ligand number 1
<220> FEATURE:
<221> NAME/KEY: CDS
<222> LOCATION: (1)..(726)

<400> SEQUENCE: 17 atg gcc cag gtg aaa ctg cag cag tct ggg gct gag ctt gtg atg cct        48
Met Ala Gln Val Lys Leu Gln Gln Ser Gly Ala Glu Leu Val Met Pro
1               5                   10                  15 ggg gct tca gtg aag atg tcc tgc aag gct tct ggc tac aca ttc act        96
Gly Ala Ser Val Lys Met Ser Cys Lys Ala Ser Gly Tyr Thr Phe Thr
            20                  25                  30 gac tac tgg atg cac tgg gtg aag cag agg cct gga caa ggc ctt gag       144
Asp Tyr Trp Met His Trp Val Lys Gln Arg Pro Gly Gln Gly Leu Glu
        35                  40                  45 tgg atc gga gcg att gat act tct gat agt tat act agc tac aat caa       192
Trp Ile Gly Ala Ile Asp Thr Ser Asp Ser Tyr Thr Ser Tyr Asn Gln
    50                  55                  60 aag ttc aag ggc aag gcc aca ttg act gta gac gaa tcc tcc agc aca       240
Lys Phe Lys Gly Lys Ala Thr Leu Thr Val Asp Glu Ser Ser Ser Thr
65                  70                  75                  80 gcc tac atg cag ctc agc agc ctg aca tct gag gac tct gcg gtc tat       288
Ala Tyr Met Gln Leu Ser Ser Leu Thr Ser Glu Asp Ser Ala Val Tyr
                85                  90                  95 tac tgt gca aga aga ggc tac tat agc gca ttt gat tac tgg ggc caa       336
Tyr Cys Ala Arg Arg Gly Tyr Tyr Ser Ala Phe Asp Tyr Trp Gly Gln
            100                 105                 110 ggg act acg gtc acc gtc tcc tca ggt gga ggc ggt tca ggc gga ggt       384
Gly Thr Thr Val Thr Val Ser Ser Gly Gly Gly Gly Ser Gly Gly Gly
        115                 120                 125 ggc tct ggc ggt ggc gga tcg gac att gag ctc acc cag tct cca aca       432
Gly Ser Gly Gly Gly Gly Ser Asp Ile Glu Leu Thr Gln Ser Pro Thr
    130                 135                 140 acc atg gct gca tct cca gga gag aag gtc acc atc acc tgc cgt gcc       480
Thr Met Ala Ala Ser Pro Gly Glu Lys Val Thr Ile Thr Cys Arg Ala
145                 150                 155                 160 agc tca agt gta agc tac atg cac tgg ttc cag cag aag tca ggc acc       528
Ser Ser Ser Val Ser Tyr Met His Trp Phe Gln Gln Lys Ser Gly Thr
                165                 170                 175 tcc ccc aaa ccc tgg att tat gac aca tcc aag ctg gct tct gga gtc       576
Ser Pro Lys Pro Trp Ile Tyr Asp Thr Ser Lys Leu Ala Ser Gly Val
            180                 185                 190 cca gat cgc ttc agt ggc agt ggg tct ggg acc tct tat tct ctc aca       624
Pro Asp Arg Phe Ser Gly Ser Gly Ser Gly Thr Ser Tyr Ser Leu Thr
        195                 200                 205 atc agc tcc atg gag gct gaa gat gct gct act tat tac tgt ctg cag       672
Ile Ser Ser Met Glu Ala Glu Asp Ala Ala Thr Tyr Tyr Cys Leu Gln
    210                 215                 220 agg agt agt tac ccg tac acg ttt gga gct ggc acc aag ctg gaa atc       720
Arg Ser Ser Tyr Pro Tyr Thr Phe Gly Ala Gly Thr Lys Leu Glu Ile
225                 230                 235                 240 aaa cgg                                                               726
Lys Arg <210> SEQ ID NO 18
<211> LENGTH: 242
<212> TYPE: PRT
<213> ORGANISM: Artificial
<220> FEATURE:
<223> OTHER INFORMATION: Artificial antibody ligand number 1
```

-continued

```
<400> SEQUENCE: 18

Met Ala Gln Val Lys Leu Gln Gln Ser Gly Ala Glu Leu Val Met Pro
1               5                   10                  15

Gly Ala Ser Val Lys Met Ser Cys Lys Ala Ser Gly Tyr Thr Phe Thr
                20                  25                  30

Asp Tyr Trp Met His Trp Val Lys Gln Arg Pro Gly Gln Gly Leu Glu
            35                  40                  45

Trp Ile Gly Ala Ile Asp Thr Ser Asp Ser Tyr Thr Ser Tyr Asn Gln
    50                  55                  60

Lys Phe Lys Gly Lys Ala Thr Leu Thr Val Asp Glu Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Arg Gly Tyr Tyr Ser Ala Phe Asp Tyr Trp Gly Gln
            100                 105                 110

Gly Thr Thr Val Thr Val Ser Ser Gly Gly Gly Ser Gly Gly Gly
                115                 120                 125

Gly Ser Gly Gly Gly Ser Asp Ile Glu Leu Thr Gln Ser Pro Thr
130                 135                 140

Thr Met Ala Ala Ser Pro Gly Glu Lys Val Thr Ile Thr Cys Arg Ala
145                 150                 155                 160

Ser Ser Ser Val Ser Tyr Met His Trp Phe Gln Lys Ser Gly Thr
                165                 170                 175

Ser Pro Lys Pro Trp Ile Tyr Asp Thr Ser Lys Leu Ala Ser Gly Val
            180                 185                 190

Pro Asp Arg Phe Ser Gly Ser Gly Ser Gly Thr Ser Tyr Ser Leu Thr
            195                 200                 205

Ile Ser Ser Met Glu Ala Glu Asp Ala Ala Thr Tyr Tyr Cys Leu Gln
    210                 215                 220

Arg Ser Ser Tyr Pro Tyr Thr Phe Gly Ala Gly Thr Lys Leu Glu Ile
225                 230                 235                 240

Lys Arg

<210> SEQ ID NO 19
<211> LENGTH: 726
<212> TYPE: DNA
<213> ORGANISM: Artificial
<220> FEATURE:
<223> OTHER INFORMATION: Artificial antibody ligand number 2
<220> FEATURE:
<221> NAME/KEY: CDS
<222> LOCATION: (1)..(726)

<400> SEQUENCE: 19 atg gcc cag gtc aag ctg cag cag tca gga cct gag ctg gta aag cct    48
Met Ala Gln Val Lys Leu Gln Gln Ser Gly Pro Glu Leu Val Lys Pro
1               5                   10                  15 ggg gct tca gtg aag atg tcc tgc aag gct tct gga tac aca ttc act    96
Gly Ala Ser Val Lys Met Ser Cys Lys Ala Ser Gly Tyr Thr Phe Thr
                20                  25                  30 agc tat gtt atg cac tgg gtg aag cag aag cct ggg cag ggc ctt gag   144
Ser Tyr Val Met His Trp Val Lys Gln Lys Pro Gly Gln Gly Leu Glu
            35                  40                  45 tgg att gga tat att aat cct tac aat gat ggt act aag tac aat gag   192
Trp Ile Gly Tyr Ile Asn Pro Tyr Asn Asp Gly Thr Lys Tyr Asn Glu
    50                  55                  60 aag ttc aaa ggc aag gcc gca ctg act tca gac aaa tcc tcc agc aca   240
```

| | | | | | | | | | | | | | | | | |
|---|---|---|---|---|---|---|---|---|---|---|---|---|---|---|---|---|
|Lys|Phe|Lys|Gly|Lys|Ala|Ala|Leu|Thr|Ser|Asp|Lys|Ser|Ser|Ser|Thr| |
|65| | | |70| | | |75| | | |80| | | | |

| gcc | tac | atg | gag | ctc | agc | agc | ctg | acc | tct | gag | gac | tct | gcg | gtc | tat | 288 |
|---|---|---|---|---|---|---|---|---|---|---|---|---|---|---|---|---|
| Ala | Tyr | Met | Glu | Leu | Ser | Ser | Leu | Thr | Ser | Glu | Asp | Ser | Ala | Val | Tyr | |
| | | | 85 | | | | | 90 | | | | | 95 | | | |

| tac | tgt | gca | aga | ttt | ggt | aac | tac | ggt | gct | ttg | gac | tac | tgg | ggc | caa | 336 |
|---|---|---|---|---|---|---|---|---|---|---|---|---|---|---|---|---|
| Tyr | Cys | Ala | Arg | Phe | Gly | Asn | Tyr | Gly | Ala | Leu | Asp | Tyr | Trp | Gly | Gln | |
| | | | 100 | | | | | 105 | | | | | 110 | | | |

| ggg | acc | acg | gtc | acc | gtc | tcc | tca | ggt | gga | ggc | ggt | tca | ggc | gga | ggt | 384 |
|---|---|---|---|---|---|---|---|---|---|---|---|---|---|---|---|---|
| Gly | Thr | Thr | Val | Thr | Val | Ser | Ser | Gly | Gly | Gly | Gly | Ser | Gly | Gly | Gly | |
| | | 115 | | | | | 120 | | | | | 125 | | | | |

| ggc | tct | ggc | ggt | ggc | gga | tcg | gac | att | gag | ctc | acc | cag | tct | cca | aca | 432 |
|---|---|---|---|---|---|---|---|---|---|---|---|---|---|---|---|---|
| Gly | Ser | Gly | Gly | Gly | Gly | Ser | Asp | Ile | Glu | Leu | Thr | Gln | Ser | Pro | Thr | |
| | 130 | | | | | 135 | | | | | 140 | | | | | |

| atc | atg | tct | gca | tct | cca | ggg | gag | aag | gtc | acc | ata | acc | tgc | agt | gcc | 480 |
|---|---|---|---|---|---|---|---|---|---|---|---|---|---|---|---|---|
| Ile | Met | Ser | Ala | Ser | Pro | Gly | Glu | Lys | Val | Thr | Ile | Thr | Cys | Ser | Ala | |
| 145 | | | | | 150 | | | | | 155 | | | | | 160 | |

| agc | tca | agt | gta | agt | tac | atg | cac | tgg | ttc | cag | cag | aag | cca | ggc | act | 528 |
|---|---|---|---|---|---|---|---|---|---|---|---|---|---|---|---|---|
| Ser | Ser | Ser | Val | Ser | Tyr | Met | His | Trp | Phe | Gln | Gln | Lys | Pro | Gly | Thr | |
| | | | | 165 | | | | | 170 | | | | | 175 | | |

| tct | ccc | aaa | ccc | tgg | att | tat | ggc | aca | tcc | aac | ctg | gct | tct | gga | gtc | 576 |
|---|---|---|---|---|---|---|---|---|---|---|---|---|---|---|---|---|
| Ser | Pro | Lys | Pro | Trp | Ile | Tyr | Gly | Thr | Ser | Asn | Leu | Ala | Ser | Gly | Val | |
| | | | 180 | | | | | 185 | | | | | 190 | | | |

| cct | gtt | cgc | ttc | agt | ggc | agt | gga | tct | ggg | acc | tct | tat | tct | ctc | aca | 624 |
|---|---|---|---|---|---|---|---|---|---|---|---|---|---|---|---|---|
| Pro | Val | Arg | Phe | Ser | Gly | Ser | Gly | Ser | Gly | Thr | Ser | Tyr | Ser | Leu | Thr | |
| | | 195 | | | | | 200 | | | | | 205 | | | | |

| atc | agc | agc | atg | gag | gct | gaa | gat | gct | gcc | act | tat | tac | tgt | caa | cag | 672 |
|---|---|---|---|---|---|---|---|---|---|---|---|---|---|---|---|---|
| Ile | Ser | Ser | Met | Glu | Ala | Glu | Asp | Ala | Ala | Thr | Tyr | Tyr | Cys | Gln | Gln | |
| | 210 | | | | | 215 | | | | | 220 | | | | | |

| tgg | agt | agt | tac | cca | ctc | acg | ttc | gga | ggg | ggg | acc | aag | ctg | gaa | ata | 720 |
|---|---|---|---|---|---|---|---|---|---|---|---|---|---|---|---|---|
| Trp | Ser | Ser | Tyr | Pro | Leu | Thr | Phe | Gly | Gly | Gly | Thr | Lys | Leu | Glu | Ile | |
| 225 | | | | | 230 | | | | | 235 | | | | | 240 | |

| aaa | cgg | | | | | | | | | | | | | | | 726 |
|---|---|---|---|---|---|---|---|---|---|---|---|---|---|---|---|---|
| Lys | Arg | | | | | | | | | | | | | | | |

<210> SEQ ID NO 20
<211> LENGTH: 242
<212> TYPE: PRT
<213> ORGANISM: Artificial
<220> FEATURE:
<223> OTHER INFORMATION: Artificial antibody ligand number 2

<400> SEQUENCE: 20

| | | | | | | | | | | | | | | | |
|---|---|---|---|---|---|---|---|---|---|---|---|---|---|---|---|
|Met|Ala|Gln|Val|Lys|Leu|Gln|Gln|Ser|Gly|Pro|Glu|Leu|Val|Lys|Pro|
|1| | | |5| | | |10| | | |15| | | |

| | | | | | | | | | | | | | | | |
|---|---|---|---|---|---|---|---|---|---|---|---|---|---|---|---|
|Gly|Ala|Ser|Val|Lys|Met|Ser|Cys|Lys|Ala|Ser|Gly|Tyr|Thr|Phe|Thr|
| | | |20| | | |25| | | |30| | | | |

| | | | | | | | | | | | | |
|---|---|---|---|---|---|---|---|---|---|---|---|---|
|Ser|Tyr|Val|Met|His|Trp|Val|Lys|Gln|Lys|Pro|Gly|Gln|Gly|Leu|Glu|
| | |35| | | |40| | | |45| | | | | |

| | | | | | | | | | | | | | | | |
|---|---|---|---|---|---|---|---|---|---|---|---|---|---|---|---|
|Trp|Ile|Gly|Tyr|Ile|Asn|Pro|Tyr|Asn|Asp|Gly|Thr|Lys|Tyr|Asn|Glu|
| |50| | | |55| | | |60| | | | | | |

| | | | | | | | | | | | | | | | |
|---|---|---|---|---|---|---|---|---|---|---|---|---|---|---|---|
|Lys|Phe|Lys|Gly|Lys|Ala|Ala|Leu|Thr|Ser|Asp|Lys|Ser|Ser|Ser|Thr|
|65| | | |70| | | |75| | | |80| | | | |

| | | | | | | | | | | | | | | | |
|---|---|---|---|---|---|---|---|---|---|---|---|---|---|---|---|
|Ala|Tyr|Met|Glu|Leu|Ser|Ser|Leu|Thr|Ser|Glu|Asp|Ser|Ala|Val|Tyr|
| | | |85| | | |90| | | |95| | | | |

| | | | | | | | | | | | | | | | |
|---|---|---|---|---|---|---|---|---|---|---|---|---|---|---|---|
|Tyr|Cys|Ala|Arg|Phe|Gly|Asn|Tyr|Gly|Ala|Leu|Asp|Tyr|Trp|Gly|Gln|
| | | |100| | | |105| | | |110| | | | |

| | | | | | | | | | | | | | | | |
|---|---|---|---|---|---|---|---|---|---|---|---|---|---|---|---|
|Gly|Thr|Thr|Val|Thr|Val|Ser|Ser|Gly|Gly|Gly|Gly|Ser|Gly|Gly|Gly|
| | |115| | | | |120| | | | |125| | | |

```
Gly Ser Gly Gly Gly Ser Asp Ile Glu Leu Thr Gln Ser Pro Thr
    130             135                 140

Ile Met Ser Ala Ser Pro Gly Glu Lys Val Thr Ile Thr Cys Ser Ala
145             150                 155                 160

Ser Ser Ser Val Ser Tyr Met His Trp Phe Gln Gln Lys Pro Gly Thr
                165             170                 175

Ser Pro Lys Pro Trp Ile Tyr Gly Thr Ser Asn Leu Ala Ser Gly Val
            180                 185                 190

Pro Val Arg Phe Ser Gly Ser Gly Ser Gly Thr Ser Tyr Ser Leu Thr
        195                 200                 205

Ile Ser Ser Met Glu Ala Glu Asp Ala Ala Thr Tyr Tyr Cys Gln Gln
    210                 215                 220

Trp Ser Ser Tyr Pro Leu Thr Phe Gly Gly Gly Thr Lys Leu Glu Ile
225             230                 235                 240

Lys Arg

<210> SEQ ID NO 21
<211> LENGTH: 795
<212> TYPE: DNA
<213> ORGANISM: Artificial
<220> FEATURE:
<223> OTHER INFORMATION: Nucleic acid encoding scFv antibody 4A
<220> FEATURE:
<221> NAME/KEY: CDS
<222> LOCATION: (1)..(795)

<400> SEQUENCE: 21 atg gcc cag gtg cag ctg cag gag tca gga cct ggc ctt gtg aaa ccc      48
Met Ala Gln Val Gln Leu Gln Glu Ser Gly Pro Gly Leu Val Lys Pro
1               5                   10                  15 tca cag tca ctc tcc ctc acc tgt tct gtc act ggt tac tcc atc act      96
Ser Gln Ser Leu Ser Leu Thr Cys Ser Val Thr Gly Tyr Ser Ile Thr
                20                  25                  30 agt aat tac tgg ggc tgg atc cgg aag ttc cca ggg aat aaa atg gag     144
Ser Asn Tyr Trp Gly Trp Ile Arg Lys Phe Pro Gly Asn Lys Met Glu
            35                  40                  45 tgg atg gga tac ata agc tac agt ggt agc act agc tac aac cca tct     192
Trp Met Gly Tyr Ile Ser Tyr Ser Gly Ser Thr Ser Tyr Asn Pro Ser
        50                  55                  60 ctc aaa agt cga atc tcc att act aga gac aca tcg aag aat cag ctc     240
Leu Lys Ser Arg Ile Ser Ile Thr Arg Asp Thr Ser Lys Asn Gln Leu
65                  70                  75                  80 ttc ctg cag ttg aac tct gta act act gag gac aca gcc aca tat tac     288
Phe Leu Gln Leu Asn Ser Val Thr Thr Glu Asp Thr Ala Thr Tyr Tyr
                85                  90                  95 tgt gca aga tat agc ctc ttt aac tac ggt agg agg gac tat gtt atg     336
Cys Ala Arg Tyr Ser Leu Phe Asn Tyr Gly Arg Arg Asp Tyr Val Met
                100                 105                 110 gat gcc tgg ggc caa ggg acc acg gtc acc gtc tcc tca ggt gga ggc     384
Asp Ala Trp Gly Gln Gly Thr Thr Val Thr Val Ser Ser Gly Gly Gly
            115                 120                 125 ggt tca ggc gga ggt ggc tct ggc ggt ggc gga tcg gac att gag ctc     432
Gly Ser Gly Gly Gly Gly Ser Gly Gly Gly Gly Ser Asp Ile Glu Leu
        130                 135                 140 acc cag tct cca gca acc atg gct gca tct cca gga gag aaa gtc acc     480
Thr Gln Ser Pro Ala Thr Met Ala Ala Ser Pro Gly Glu Lys Val Thr
145                 150                 155                 160 atc acc tgc cgt gcc agc tca act gta agc tac atg cac tgg ttc caa     528
Ile Thr Cys Arg Ala Ser Ser Thr Val Ser Tyr Met His Trp Phe Gln
```

```
                 165                 170                 175
cag aag cca ggc gcc tcc cct aaa ccc tgg att tat gac aca tcc aaa      576
Gln Lys Pro Gly Ala Ser Pro Lys Pro Trp Ile Tyr Asp Thr Ser Lys
            180                 185                 190 ctg gct tct gga gtc cca gat cgc ttc agt ggc agt ggg tct ggg aca      624
Leu Ala Ser Gly Val Pro Asp Arg Phe Ser Gly Ser Gly Ser Gly Thr
        195                 200                 205 gac ttc acc ctc acc att gat cct gtg cag gct gat gat att gca acc      672
Asp Phe Thr Leu Thr Ile Asp Pro Val Gln Ala Asp Asp Ile Ala Thr
    210                 215                 220 tat tac tgt cag cag agt aag gat gat cct cgg acg ttc ggt gga ggg      720
Tyr Tyr Cys Gln Gln Ser Lys Asp Asp Pro Arg Thr Phe Gly Gly Gly
225                 230                 235                 240 acc aag ctg gag ctg aaa cgg cgg ccg cag gtg cgc cgg tgc cgt atc      768
Thr Lys Leu Glu Leu Lys Arg Arg Pro Gln Val Arg Arg Cys Arg Ile
                245                 250                 255 cgg atc cgc tgg aac cgc gtg ccg cat                                  795
Arg Ile Arg Trp Asn Arg Val Pro His
            260                 265

<210> SEQ ID NO 22
<211> LENGTH: 265
<212> TYPE: PRT
<213> ORGANISM: Artificial
<220> FEATURE:
<223> OTHER INFORMATION: Nucleic acid encoding scFv antibody 4A

<400> SEQUENCE: 22

Met Ala Gln Val Gln Leu Gln Glu Ser Gly Pro Gly Leu Val Lys Pro
1               5                   10                  15

Ser Gln Ser Leu Ser Leu Thr Cys Ser Val Thr Gly Tyr Ser Ile Thr
            20                  25                  30

Ser Asn Tyr Trp Gly Trp Ile Arg Lys Phe Pro Gly Asn Lys Met Glu
        35                  40                  45

Trp Met Gly Tyr Ile Ser Tyr Ser Gly Ser Thr Ser Tyr Asn Pro Ser
    50                  55                  60

Leu Lys Ser Arg Ile Ser Ile Thr Arg Asp Thr Ser Lys Asn Gln Leu
65                  70                  75                  80

Phe Leu Gln Leu Asn Ser Val Thr Thr Glu Asp Thr Ala Thr Tyr Tyr
                85                  90                  95

Cys Ala Arg Tyr Ser Leu Phe Asn Tyr Gly Arg Arg Asp Tyr Val Met
            100                 105                 110

Asp Ala Trp Gly Gln Gly Thr Thr Val Thr Val Ser Ser Gly Gly Gly
        115                 120                 125

Gly Ser Gly Gly Gly Gly Ser Gly Gly Gly Gly Ser Asp Ile Glu Leu
    130                 135                 140

Thr Gln Ser Pro Ala Thr Met Ala Ala Ser Pro Gly Glu Lys Val Thr
145                 150                 155                 160

Ile Thr Cys Arg Ala Ser Ser Thr Val Ser Tyr Met His Trp Phe Gln
                165                 170                 175

Gln Lys Pro Gly Ala Ser Pro Lys Pro Trp Ile Tyr Asp Thr Ser Lys
            180                 185                 190

Leu Ala Ser Gly Val Pro Asp Arg Phe Ser Gly Ser Gly Ser Gly Thr
        195                 200                 205

Asp Phe Thr Leu Thr Ile Asp Pro Val Gln Ala Asp Asp Ile Ala Thr
    210                 215                 220

Tyr Tyr Cys Gln Gln Ser Lys Asp Asp Pro Arg Thr Phe Gly Gly Gly
```

|       |       |       |       |       | 225   |       |       |       |       | 230   |       |       |       |       | 235   |       |       |       |       | 240   |
|-------|-------|-------|-------|-------|-------|-------|-------|-------|-------|-------|-------|-------|-------|-------|-------|-------|-------|-------|-------|-------|

Thr Lys Leu Glu Leu Lys Arg Arg Pro Gln Val Arg Arg Cys Arg Ile
                245                 250                 255

Arg Ile Arg Trp Asn Arg Val Pro His
        260                 265

<210> SEQ ID NO 23
<211> LENGTH: 786
<212> TYPE: DNA
<213> ORGANISM: artificial
<220> FEATURE:
<223> OTHER INFORMATION: nucleic acid encoding scFv antibody 10A
<220> FEATURE:
<221> NAME/KEY: CDS
<222> LOCATION: (1)..(786)

<400> SEQUENCE: 23

| atg gcc cag gtg aag ctg cag cag tct gga cct gag ctg gta aag cct | 48 |
| Met Ala Gln Val Lys Leu Gln Gln Ser Gly Pro Glu Leu Val Lys Pro | |
| 1               5                   10                  15     | |

| ggg gct tca gtg aag atg tcc tgc aag gct tct gga tac aca ttc act | 96 |
| Gly Ala Ser Val Lys Met Ser Cys Lys Ala Ser Gly Tyr Thr Phe Thr | |
|             20                  25                  30         | |

| agc tat gtt atg cac tgg gtg aag cag agc aat gga aag agc ctt gag | 144 |
| Ser Tyr Val Met His Trp Val Lys Gln Ser Asn Gly Lys Ser Leu Glu | |
|         35                  40                  45             | |

| tgg att gga act att gat cct tac tat ggt ggt act agc tac aac cag | 192 |
| Trp Ile Gly Thr Ile Asp Pro Tyr Tyr Gly Gly Thr Ser Tyr Asn Gln | |
|     50                  55                  60                 | |

| aag ttc aag ggc aag gcc aca ttg act gta gac aaa tcc tcc acc acg | 240 |
| Lys Phe Lys Gly Lys Ala Thr Leu Thr Val Asp Lys Ser Ser Thr Thr | |
| 65                  70                  75                  80 | |

| gcc tac ata cag ctc aag agc ctg aca tct gag gac tct gca gtc tat | 288 |
| Ala Tyr Ile Gln Leu Lys Ser Leu Thr Ser Glu Asp Ser Ala Val Tyr | |
|                 85                  90                  95     | |

| tac tgt gca aga tgg gat ggt tac tac gga ggg ttt tct tac tgg ggc | 336 |
| Tyr Cys Ala Arg Trp Asp Gly Tyr Tyr Gly Gly Phe Ser Tyr Trp Gly | |
|             100                 105                 110        | |

| caa ggg acc atg gtc acc gtc tcc tca ggt gga ggc ggt tca ggc gga | 384 |
| Gln Gly Thr Met Val Thr Val Ser Ser Gly Gly Gly Gly Ser Gly Gly | |
|         115                 120                 125            | |

| ggt ggc tct ggc ggt ggc gga tcg gac att gag ctc acc cag tct cca | 432 |
| Gly Gly Ser Gly Gly Gly Gly Ser Asp Ile Glu Leu Thr Gln Ser Pro | |
|     130                 135                 140                | |

| gca atc atg tct gca act cta ggg gag aag gtc acc atg agc tgc agg | 480 |
| Ala Ile Met Ser Ala Thr Leu Gly Glu Lys Val Thr Met Ser Cys Arg | |
| 145                 150                 155                 160 | |

| gcc agc tca aat gta aag tac atg tac tgg tac cag cag aag tca ggt | 528 |
| Ala Ser Ser Asn Val Lys Tyr Met Tyr Trp Tyr Gln Gln Lys Ser Gly | |
|                 165                 170                 175    | |

| gcc tcc ccc aaa cta tgg att tat tac aca tcc aac ctg gct tct gga | 576 |
| Ala Ser Pro Lys Leu Trp Ile Tyr Tyr Thr Ser Asn Leu Ala Ser Gly | |
|             180                 185                 190        | |

| gtc cca gct cgc ttc agt ggc agt ggg tct ggg acc tct tat tct ctc | 624 |
| Val Pro Ala Arg Phe Ser Gly Ser Gly Ser Gly Thr Ser Tyr Ser Leu | |
|         195                 200                 205            | |

| aca atc agc agc gtg gag gct gaa gat gct gcc act tat tac tgc cag | 672 |
| Thr Ile Ser Ser Val Glu Ala Glu Asp Ala Ala Thr Tyr Tyr Cys Gln | |
|     210                 215                 220                | |

| cag ttt act agt tcc ccg tat acg ttc gga tcg ggc acc aag ctg gaa | 720 |
| Gln Phe Thr Ser Ser Pro Tyr Thr Phe Gly Ser Gly Thr Lys Leu Glu | |

```
                225                 230                 235                 240
atc aaa cgg gcg gcc gca ggt gcg ccg gtg ccg tat ccg gat ccg ctg              768
Ile Lys Arg Ala Ala Ala Gly Ala Pro Val Pro Tyr Pro Asp Pro Leu
                245                 250                 255 gaa ccg cgt gcc gca tag                                                      786
Glu Pro Arg Ala Ala
        260
```

<210> SEQ ID NO 24
<211> LENGTH: 261
<212> TYPE: PRT
<213> ORGANISM: artificial
<220> FEATURE:
<223> OTHER INFORMATION: nucleic acid encoding scFv antibody 10A

<400> SEQUENCE: 24

```
Met Ala Gln Val Lys Leu Gln Gln Ser Gly Pro Glu Leu Val Lys Pro
1               5                   10                  15

Gly Ala Ser Val Lys Met Ser Cys Lys Ala Ser Gly Tyr Thr Phe Thr
            20                  25                  30

Ser Tyr Val Met His Trp Val Lys Gln Ser Asn Gly Lys Ser Leu Glu
        35                  40                  45

Trp Ile Gly Thr Ile Asp Pro Tyr Tyr Gly Gly Thr Ser Tyr Asn Gln
    50                  55                  60

Lys Phe Lys Gly Lys Ala Thr Leu Thr Val Asp Lys Ser Ser Thr Thr
65                  70                  75                  80

Ala Tyr Ile Gln Leu Lys Ser Leu Thr Ser Glu Asp Ser Ala Val Tyr
                85                  90                  95

Tyr Cys Ala Arg Trp Asp Gly Tyr Tyr Gly Phe Ser Tyr Trp Gly
            100                 105                 110

Gln Gly Thr Met Val Thr Val Ser Ser Gly Gly Gly Ser Gly Gly
        115                 120                 125

Gly Gly Ser Gly Gly Gly Ser Asp Ile Glu Leu Thr Gln Ser Pro
    130                 135                 140

Ala Ile Met Ser Ala Thr Leu Gly Glu Lys Val Thr Met Ser Cys Arg
145                 150                 155                 160

Ala Ser Ser Asn Val Lys Tyr Met Tyr Trp Tyr Gln Gln Lys Ser Gly
                165                 170                 175

Ala Ser Pro Lys Leu Trp Ile Tyr Tyr Thr Ser Asn Leu Ala Ser Gly
            180                 185                 190

Val Pro Ala Arg Phe Ser Gly Ser Gly Ser Gly Thr Ser Tyr Ser Leu
        195                 200                 205

Thr Ile Ser Ser Val Glu Ala Glu Asp Ala Ala Thr Tyr Tyr Cys Gln
    210                 215                 220

Gln Phe Thr Ser Ser Pro Tyr Thr Phe Gly Ser Gly Thr Lys Leu Glu
225                 230                 235                 240

Ile Lys Arg Ala Ala Ala Gly Ala Pro Val Pro Tyr Pro Asp Pro Leu
                245                 250                 255

Glu Pro Arg Ala Ala
        260
```

<210> SEQ ID NO 25
<211> LENGTH: 13
<212> TYPE: PRT
<213> ORGANISM: Artificial
<220> FEATURE:
<223> OTHER INFORMATION: Amino acid sequence of the E-tag epitope tag

<400> SEQUENCE: 25

Gly Ala Pro Val Pro Tyr Pro Asp Pro Leu Glu Pro Arg
1               5                   10

<210> SEQ ID NO 26
<211> LENGTH: 17
<212> TYPE: PRT
<213> ORGANISM: Artificial
<220> FEATURE:
<223> OTHER INFORMATION: Artificial integrin-binding peptide with the
      linking peptide
      sequence SGSGS at the C-terminus

<400> SEQUENCE: 26

His His Leu Gly Gly Ala Lys Gln Ala Gly Asp Val Ser Gly Ser Gly
1               5                   10                  15

Ser

<210> SEQ ID NO 27
<211> LENGTH: 18
<212> TYPE: PRT
<213> ORGANISM: Artificial
<220> FEATURE:
<223> OTHER INFORMATION: Artificial integrin-binding peptide ligand
      containing the SGSGS
      linking peptide at the N-terminus

<400> SEQUENCE: 27

Ser Gly Ser Gly Ser His His Leu Gly Gly Ala Lys Gln Ala Gly Asp
1               5                   10                  15

Val Cys

<210> SEQ ID NO 28
<211> LENGTH: 22
<212> TYPE: PRT
<213> ORGANISM: Artificial
<220> FEATURE:
<223> OTHER INFORMATION: Artificial integrin-binding peptide with the
      SGSGS linking petide
      and the poly-tyrosine stretch for complexing with IODO-GEN

<400> SEQUENCE: 28

His His Leu Gly Gly Ala Lys Gln Ala Gly Asp Val Ser Gly Ser Gly
1               5                   10                  15

Ser Tyr Tyr Tyr Tyr Tyr
            20

<210> SEQ ID NO 29
<211> LENGTH: 18
<212> TYPE: PRT
<213> ORGANISM: Artificial
<220> FEATURE:
<223> OTHER INFORMATION: Artificial integrin-binding peptide with the
      linking peptide
      SGSGSC

<400> SEQUENCE: 29

His His Leu Gly Gly Ala Lys Gln Ala Gly Asp Val Ser Gly Ser Gly
1               5                   10                  15

Ser Cys

<210> SEQ ID NO 30
<211> LENGTH: 18
<212> TYPE: PRT
<213> ORGANISM: Artificial

```
<220> FEATURE:
<223> OTHER INFORMATION: Artificial integrin-binding peptide containing
      the linking
      peptide SGSGSK

<400> SEQUENCE: 30

His His Leu Gly Gly Ala Lys Gln Ala Gly Asp Val Ser Ser Gly
1               5                   10                  15

Ser Lys

<210> SEQ ID NO 31
<211> LENGTH: 5
<212> TYPE: PRT
<213> ORGANISM: Artificial
<220> FEATURE:
<223> OTHER INFORMATION: Serine-Glycine linking peptide

<400> SEQUENCE: 31

Ser Gly Ser Gly Ser
1               5

<210> SEQ ID NO 32
<211> LENGTH: 10
<212> TYPE: DNA
<213> ORGANISM: Artificial
<220> FEATURE:
<223> OTHER INFORMATION: Serine-glycine-poly-tyrosine linking peptide

<400> SEQUENCE: 32 sgsgsyyyyy                                                              10

<210> SEQ ID NO 33
<211> LENGTH: 22
<212> TYPE: PRT
<213> ORGANISM: Artificial
<220> FEATURE:
<223> OTHER INFORMATION: Poly-serine-glycine-poly-tyrosine negative
      control linking
      peptide

<400> SEQUENCE: 33

Ser Gly Ser Gly Ser Gly Ser Ser Gly Ser Gly Ser Ser Gly Ser Gly
1               5                   10                  15

Ser Tyr Tyr Tyr Tyr Tyr
            20

<210> SEQ ID NO 34
<211> LENGTH: 17
<212> TYPE: PRT
<213> ORGANISM: Artificial
<220> FEATURE:
<223> OTHER INFORMATION: Poly-serine-glycine negative control peptide

<400> SEQUENCE: 34

Ser Gly Ser Gly Ser Ser Gly Ser Gly Ser Gly Ser Ser Gly Ser Gly
1               5                   10                  15

Ser
```